United States Patent
Weber et al.

(10) Patent No.: US 9,863,935 B2
(45) Date of Patent: Jan. 9, 2018

(54) PREDICTIVE BIOMARKERS FOR CTLA-4 BLOCKADE THERAPY AND FOR PD-1 BLOCKADE THERAPY

(71) Applicant: H. Lee Moffitt Cancer Center and Research Institute, Inc., Tampa, FL (US)

(72) Inventors: Jeffrey S. Weber, Tampa, FL (US); Wenshi Wang, Tampa, FL (US); Bin Yu, Tampa, FL (US)

(73) Assignee: H. Lee Moffitt Cancer and Research Institute, Inc., Tampa, FL (US)

( * ) Notice: Subject to any disclaimer, the term of this patent is extended or adjusted under 35 U.S.C. 154(b) by 340 days.

(21) Appl. No.: 14/399,669

(22) PCT Filed: Mar. 15, 2013

(86) PCT No.: PCT/US2013/032254
§ 371 (c)(1),
(2) Date: Nov. 7, 2014

(87) PCT Pub. No.: WO2013/169388
PCT Pub. Date: Nov. 14, 2013

(65) Prior Publication Data
US 2015/0118245 A1    Apr. 30, 2015

Related U.S. Application Data

(60) Provisional application No. 61/644,004, filed on May 8, 2012, provisional application No. 61/644,988, filed on May 9, 2012.

(51) Int. Cl.
| | |
|---|---|
| C07K 16/00 | (2006.01) |
| G01N 33/50 | (2006.01) |
| G01N 33/569 | (2006.01) |
| G01N 33/574 | (2006.01) |
| C07K 16/28 | (2006.01) |
| C07K 16/30 | (2006.01) |
| A61K 39/00 | (2006.01) |

(52) U.S. Cl.
CPC ..... *G01N 33/5091* (2013.01); *C07K 16/2818* (2013.01); *C07K 16/3053* (2013.01); *G01N 33/56972* (2013.01); *G01N 33/5743* (2013.01); *A61K 2039/505* (2013.01); *C07K 2317/21* (2013.01); *G01N 2333/70517* (2013.01); *G01N 2800/52* (2013.01)

(58) Field of Classification Search
None
See application file for complete search history.

(56) References Cited

FOREIGN PATENT DOCUMENTS

| WO | 2010036959 | 4/2010 |
| WO | 2012018538 | 2/2012 |

OTHER PUBLICATIONS

Hegel et al (EJI, 39:883-893, 2009).*
Attia, et al., "Autoimmunity correlates with tumor regression in patients with metastatic melanoma treated with anti-cytotoxic T-lymphocyte antigen-4", J Clin Oncol., 23:6043-53 (2005).
Carthon, et al., "Preoperative CTLA-4 blockade: tolerability and immune monitoring in the setting of a presurgical clinical trial", Clin Cancer Res.16:2861-71 (2010).
Chambers , et al., "CTLA-4-mediated inhibition in regulation of T cell responses: mechanisms and manipulation in tumor immunotherapy", Annu Rev Immunol. 19:565-94 (2001).
Chen, et al., "Anti-CTLA-4 therapy resultS in higher CD4+ICOShi T cell frequency and IFN-gamma levels in both nonmalignant and malignant prostate tissues", PNAS, 106:2729-34 (2009).
Chen, et al., "Costimulation of antitumor immunity by the B7 counterreceptor for the T lymphocyte molecules CD28 and CTLA-4", Cell, 71:1093-102 (1992).
Comin-Anduix, et al., "Modulation of cell signaling networks after CTLA4 blockade in patients with metastatic melanoma", PLoS One, 5:e12711 (2010).
Curran, et al., "PD-1 and CTLA-4 combination blockade expands infiltrating T cells and reduces regulatory T and myeloid cells within B16 melanoma tumors", PNAS, 107(9):4275-80 (2010).
Dong , et al., "ICOS co-stimulatory receptor is essential for T-cell activation and function", Nature, 409:97-101 (2001).
Egen, et al., "Cytotoxic T lymphocyte antigen-4 accumulation in the immunological synapse is regulated by TCR signal strength", Immunity., 16:23-35 (2002).
Egen, et al., "CTLA-4: new insights into its biological function and use in tumor immunotherapy", Nat Immunol., 3:611-8 (2002b).
Fisher, et al., "Melanoma from bench to bedside: meeting report from the 6th international melanoma congress", Pigment Cell Melanoma Res., 23:14-26 (2009).
Fong, et al., "Anti-cytotoxic T-lymphocyte antigen-4 antibody: the first in an emerging class of immunomodulatory antibodies for cancer treatment", J Clin Oncol., 26:5275-83 (2008).
Greenwald, et al., "CTLA-4 regulates induction of anergy in vivo", Immunity., 14:145-55 (2001).
Hertoghs, et al., "Molecular profiling of cytomegalovirus-induced human CD8+ T cell differentiation", J Clin Invest., 120:4077-90 (2010).
Hodi, et al., "Improved survival with ipilimumab in patients with metastatic melanoma", N Engl J Med.,.363:711-23 (2010).
Huang, et al., "CTLA4 blockade induces frequent tumor infiltration by activated lymphocytes regardless of clinical responses in humans", Clin Cancer Res., 17:4101-9 (2011),Leach, et al., "Enhancement of antitumor immunity by CTLA-4 blockade", Science, 271:1734-6 (1996).

(Continued)

*Primary Examiner* — Brad Duffy
(74) *Attorney, Agent, or Firm* — Pabst Patent Group LLP

(57) ABSTRACT

Biomarkers are described for predicting the efficacy, risk of relapse, risk of an immune related adverse event (irAE), or combination thereof for a CTLA-4 blockade treatment, such as ipilimumab, in a subject with melanoma. Biomarkers are also described for predicting the efficacy and clinical benefit for a PD-1 blockade treatment, such as a PD-1 blocking antibody, in a subject with melanoma.

14 Claims, 23 Drawing Sheets

(56) References Cited

OTHER PUBLICATIONS

Maker, et al., "Analysis of the cellular mechanism of antitumor responses and autoimmunity in patients treated with CTLA-4 blockade", J Immunol., 175:7746-54 (2005).
McAdam, et al., "Mouse inducible costimulatory molecule (ICOS) expression is enhanced by CD28 costimulation and regulates differentiation of CD4+ T cells", J Immunol., 165:5035-40 (2000).
Melero, et al., "Immunostimulatory monoclonal antibodies for cancer therapy", Nat Rev Cancer, 7:95-106 (2007).
O'Day, et al., "Efficacy and safety of ipilimumab monotherapy in patients with pretreated advanced melanoma: a multicenter single-arm phase II study", Ann Oncol., 21:1712-7 (2010).
Pearce, et al., "Control of effector CD8+ T cell function by the transcription factor Eomesodermin", Science, 302:1041-3 (2003).
Phan, et al., "Cancer regression and autoimmunity induced by cytotoxic T lymphocyte-associated antigen 4 blockade in patients with metastatic melanoma", PNAS, 100:8372-7 (2003).
Quezada, et al., "CTLA4 blockade and GM-CSF combination immunotherapy alters the intratumor balance of effector and regulatory T cells", J Clin Invest., 116:1935-45 (2006).
Ribas, et al., "Intratumoral immune cell infiltrates, FoxP3, and indoleamine 2,3-dioxygenase in patients with melanoma undergoing CTLA4 blockade", Clin Cancer Res., 15:390-9 (2009).
Ribas, et al., "Imaging of CTLA4 blockade-induced cell replication with (18)F-FLT PET in patients with advanced melanoma treated with tremelimumab", J Nucl Med., 51:340-6 (2010).
Ribas, "Overcoming immunologic tolerance to melanoma: targeting CTLA-4 with tremelimumab (CP-675,206)", Oncologist., 13 Suppl 4:10-5 (2008).
Robert, et al., "Ipilimumab plus dacarbazine for previously untreated metastatic melanoma", N Engl.J Med.; 364:2517-26 (2011).
Sanderson, et al., "Autoimmunity in a phase I trial of a fully human anti-cytotoxic T-lymphocyte antigen-4 monoclonal antibody with multiple melanoma peptides and Montanide ISA 51 for patients with resected stages III and IV melanoma", J Clin Oncol., 23:741-50 (2005).
Sarnaik, et al., "Extended dose ipilimumab with a peptide vaccine: immune correlates associated with clinical benefit in patients with resected high-risk stage IIIc/IV melanoma", Clin Cancer Res., 17(4):896-906 (2010).
Schneider, et al., "CTLA-4 activation of phosphatidylinositol 3-kinase (PI 3-K) and protein kinase B (PKB/AKT) sustains T-cell anergy without cell death", PLoS One, 3:e3842 (2008).
Scholzen, et al., "The Ki-67 protein: from the known and the unknown", J Cell Physiol., 182:311-22 (2000).
Ueda, et al., "Association of the T-cell regulatory gene CTLA4 with susceptibility to autoimmune disease", Nature, 423:506-11 (2003).
van Elsas, et al., "Combination Immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation", J Exp Med., 190:355-66 (1999).
von Euw, et al., "CTLA4 blockade increases Th17 cells in patients with metastatic melanoma", J Transl Med. ,7:35 (2009).
Wang, et al., "Biomarkers on melanoma patient T cells associated with ipilimumab treatment.", J Trans Med., 10(148) (2012).
Waterhouse, et al., "Lymphoproliferative disorders with early lethality in mice deficient in Ctla-4", Science, 270:985-8 (1995).
Weber, et al., "A randomized, double-blind, placebo-controlled, phase II study comparing the tolerability and efficacy of ipilimumab administered with or without prophylactic budesonide in patients with unresectable stage III or IV melanoma", Clin Cancer Res., 16:5691-8 (2009).
Weber, "Ipilimumab: controversies in its development, utility and autoimmune adverse events", Cancer Immunol Immunother., 58:823-30 (2009b).
Wolchok, et al., "Ipilimumab monetherapy in patients with pretreated advanced melanoma: a randomised, double-blind, multicentre, phase 2, dose-ranging study", Lancet Oncol.,11:155-64 (2008).
Yuan, et al., "Correlation of clinical and immunological data in a metastatic melanoma patient with heterogeneous tumor responses to ipilimumab therapy", Cancer Immun., 10:1 (2010).
Yuan, et al., "Integrated NY-ESO-1 antibody and CD8+ T-cell responses correlate with clinical benefit in advanced melanoma patients treated with ipilimumab", PNAS, 108(40):16723-8 (2011).
International Search Report for PCT/US2013/032254, dated Jun. 28, 2014.

\* cited by examiner

| Probeset | Mean of Relapse | Mean of NED | Log Ratio | p-value | FDR | Gene Symbol |
|---|---|---|---|---|---|---|
| 200958_s_at | 2774.1409 | 1401.5442 | -0.9850238 | 3.757958e-08 | 0.0006982888 | SDCBP |
| 228555_at | 289.2532 | 164.5863 | -0.8134887 | 9.917260e-08 | 0.0015370495 | CAMK2D |
| 200732_s_at | 1323.8927 | 504.3519 | -1.3922836 | 2.531617e-07 | 0.0015370495 | PTP4A1 |
| 203685_at | 1697.8515 | 803.6199 | -1.0791251 | 3.703255e-07 | 0.0037322913 | BCL2 |
| 212131_at | 2387.5170 | 1526.8953 | -0.6449099 | 7.048912e-07 | 0.0037322913 | LSM14A |
| 212406_s_at | 1738.2088 | 992.4934 | -0.8084719 | 1.313029e-06 | 0.0037322913 | PCMTD2 |
| 202842_s_at | 1675.3961 | 844.0285 | -0.9891387 | 1.357953e-06 | 0.0042753665 | DNAJB9 |
| 222624_s_at | 559.8388 | 310.1315 | -0.8521315 | 2.494378e-06 | 0.0046347353 | ZNF639 |
| 202541_at | 639.6344 | 354.3786 | -0.8519559 | 3.057545e-06 | 0.0046347353 | SCYE1 |
| 200097_s_at | 4087.7205 | 2512.3388 | -0.7022655 | 3.676176e-06 | 0.0046347353 | HNRNPK |
| 225267_at | 713.2769 | 390.8508 | -0.8678443 | 3.711066e-06 | 0.0046347353 | KPNA4 |
| 202777_at | 1221.0957 | 701.9255 | -0.7987854 | 3.779114e-06 | 0.0161531379 | SHOC2 |
| 213153_at | 1355.1501 | 718.9146 | -0.9145603 | 6.448583e-06 | 0.0161531379 | SETD1B |
| 200662_s_at | 1731.5887 | 1051.8299 | -0.7191949 | 7.310420e-06 | 0.0161531379 | TOMM20 |
| 223598_at | 726.9852 | 378.4066 | -0.9419887 | 1.127202e-05 | 0.0161531379 | RAD23B |
| 207957_s_at | 997.7070 | 531.1010 | -0.9096239 | 1.382739e-05 | 0.0161531379 | PRKCB |

FIG. 11

| | | | | |
|---|---|---|---|---|
| 212243_at | 445.2878 | 250.8329 | -0.8280118 | 1.4450077e-05 | 0.0161531379 | GCOM1 |
| 225198_at | 853.3875 | 405.7908 | -1.0724648 | 1.7739066e-05 | 0.0161531379 | VAPA |
| 227521_at | 805.7755 | 457.4011 | -0.8169180 | 1.7987789e-05 | 0.0161531379 | FBXO33 |
| 1569136_at | 645.6064 | 299.4819 | -1.1081859 | 1.8027099e-05 | 0.0215210516 | MGAT4A |
| 220306_at | 2008.4180 | 1101.1604 | -0.8670349 | 2.4310930e-05 | 0.0215210516 | FAM46C |
| 227373_at | 741.6876 | 388.8808 | -0.9314836 | 2.4473000e-05 | 0.0215210516 | ATXN1L |
| 226199_at | 388.7042 | 212.3011 | -0.8725613 | 2.7789070e-05 | 0.0215210516 | UPRT |
| 243259_at | 439.3332 | 203.6301 | -1.1093642 | 3.0380470e-05 | 0.0215210516 | ATXN7 |
| 224847_at | 739.5718 | 292.5311 | -1.3381003 | 3.5648840e-05 | 0.0215210516 | CDK6 |
| 209989_s_at | 576.0771 | 345.2136 | -0.7387728 | 3.7473320e-05 | 0.0215210516 | KDM2A |
| 244871_s_at | 138.2489 | 277.0193 | 1.0027185 | 3.9344490e-05 | 0.0215210516 | USP32 |
| 212195_at | 2894.1129 | 1835.5402 | -0.6569165 | 4.1300830e-05 | 0.0215210516 | IL6ST |
| 230511_at | 271.4390 | 113.0340 | -1.2638716 | 4.2725340e-05 | 0.0215210516 | CREM |
| 218603_at | 3506.9739 | 2692.6922 | -0.3811774 | 4.3266910e-05 | 0.0215210516 | HECA |
| 218528_s_at | 898.2200 | 564.9392 | -0.6689733 | 4.5913140e-05 | 0.0215210516 | RNF38 |
| 238633_at | 417.8006 | 214.7981 | -0.9598335 | 4.9298660e-05 | 0.0215210516 | EPC1 |
| 202720_at | 1799.1219 | 1127.2304 | -0.6745105 | 5.0754100e-05 | 0.0215210516 | TES |

FIG. 11 Continued

| | | | | |
|---|---|---|---|---|
| 239247_at | 59.3585 | 108.6497 | -0.8721574 | 5.115812e-05 | 0.0215210516 | LOC401577 |
| 226406_at | 503.9888 | 241.8912 | -1.0590336 | 5.350956e-05 | 0.0215210516 | C18orf25 |
| 202505_at | 970.2144 | 619.4133 | -0.8474013 | 5.384169e-05 | 0.0215210516 | SNRPB2 |
| 201074_at | 1208.7310 | 749.8088 | -0.6888985 | 5.747244e-05 | 0.0215210516 | SMARCC1 |
| 201574_at | 372.5346 | 212.6082 | -0.8091771 | 6.119734e-05 | 0.0215210516 | ETF1 |
| 202032_s_at | 435.4207 | 646.4488 | 0.5701261 | 6.122080e-05 | 0.0215210516 | MAN2A2 |
| 220999_s_at | 764.8459 | 393.9759 | -0.9570617 | 6.145519e-05 | 0.0215210516 | CYFIP2 |
| 200009_at | 2340.9310 | 1629.1607 | -0.5229535 | 6.386932e-05 | 0.0215210516 | GDI2 |
| 219343_at | 312.9659 | 176.9121 | -0.8229723 | 6.521633e-05 | 0.0215210516 | CDC37L1 |
| 220748_s_at | 323.9112 | 187.7416 | -0.7868498 | 6.647780e-05 | 0.0215210516 | ZNF580 |
| 201225_s_at | 2599.5135 | 1447.9589 | -0.8442210 | 6.738233e-05 | 0.0215210516 | SRRM1 |
| 225125_at | 1005.6899 | 630.9462 | -0.6725366 | 7.820719e-05 | 0.0229450996 | MMGT1 |
| 235230_at | 239.5831 | 107.0905 | -1.1616961 | 8.011832e-05 | 0.0229450996 | PLCXD2 |
| 213850_s_at | 804.2766 | 1552.2589 | 0.9486055 | 8.258174e-05 | 0.0229450996 | SFRS2IP |
| 209447_at | 646.9925 | 1051.1485 | 0.7001455 | 8.341078e-05 | 0.0229450996 | SYNE1 |
| 226527_at | 285.8785 | 175.4237 | -0.7045579 | 8.451261e-05 | 0.0229450996 | RPRD2 |
| 201524_x_at | 1628.7396 | 1029.1989 | -0.6622342 | 8.619393e-05 | 0.0229450996 | UBE2N |

FIG. 11 Continued

| Probeset | Mean of Relapse | Mean of NED | Log Ratio | p-value | FDR | Gene Symbol |
|---|---|---|---|---|---|---|
| 200732_s_at | 1107.03190 | 456.31762 | -1.2785865 | 7.648351e-07 | 0.005884624 | PTP4A1 |
| 204749_at | 182.44785 | 66.30482 | -1.4602985 | 1.018909e-06 | 0.014663586 | NAP1L3 |
| 225198_at | 788.97526 | 403.19902 | -0.9684880 | 2.288911e-06 | 0.020321774 | VAPA |
| 201515_s_at | 911.99201 | 502.33518 | -0.8603709 | 9.011908e-06 | 0.033045263 | TSN |
| 223598_at | 863.87842 | 490.45319 | -0.8167128 | 1.118505e-05 | 0.033045263 | RAD23B |
| 227708_at | 624.28726 | 376.79396 | -0.7284342 | 1.781554e-05 | 0.033045263 | EEF1A1 |
| 213153_at | 1308.62685 | 734.97758 | -0.8322816 | 1.860593e-05 | 0.033045263 | SETD1B |
| 212434_at | 692.37511 | 429.98496 | -0.6872677 | 1.997574e-05 | 0.033045263 | GRPEL1 |
| 212131_at | 2532.20450 | 1650.41108 | -0.6175685 | 2.121337e-05 | 0.045009748 | LSM14A |
| 222624_s_at | 542.78854 | 319.83745 | -0.7630514 | 2.920238e-05 | 0.045009748 | ZNF639 |
| 202541_at | 577.18604 | 346.32802 | -0.7368973 | 3.213690e-05 | 0.045009748 | SCYE1 |
| 204622_x_at | 2123.12625 | 853.88828 | -1.31140709 | 3.758653e-05 | 0.045009748 | NR4A2 |
| 202842_s_at | 1459.24925 | 792.69035 | -0.8803970 | 5.221003e-05 | 0.045009748 | DNAJB9 |
| 212168_at | 523.46361 | 363.64558 | -0.5255562 | 5.479845e-05 | 0.045009748 | RBM12 |
| 221637_s_at | 335.31039 | 490.36295 | 0.5483528 | 5.805252e-05 | 0.045009748 | C11orf48 |
| 202720_at | 2003.51938 | 1286.69484 | -0.6388665 | 5.628337e-05 | 0.058460282 | TES |

FIG. 12

| | | | | |
|---|---|---|---|---|
| 205573_s_at | 438.48205 | 280.39082 | -0.6450787 | 9.057181e-05 | 0.0584460282 | ETF1 |
| 243259_at | 364.32600 | 202.20014 | -0.8494460 | 9.233560e-05 | 0.0584460282 | ATXN7 |
| 205281_s_at | 296.41626 | 129.46820 | -1.1950268 | 1.015251e-04 | 0.0584460282 | PIGA |
| 212787_at | 716.90729 | 491.47077 | -0.5446809 | 1.116737e-04 | 0.0584460282 | YLPM1 |
| 202777_at | 1217.83223 | 820.14353 | -0.5703671 | 1.118008e-04 | 0.0584460282 | SHOC2 |
| 225267_at | 789.63199 | 427.37308 | -0.8856844 | 1.122117e-04 | 0.0584460282 | KPNA4 |
| 226527_at | 239.20541 | 162.31643 | -0.5594410 | 1.212620e-04 | 0.0584460282 | RPRD2 |
| 229083_at | 262.29076 | 132.95199 | -0.9802616 | 1.297400e-04 | 0.0584460282 | HNRNPA0 |
| 209733_at | 127.90204 | 68.74016 | -0.8958141 | 1.368075e-04 | 0.0584460282 | MID2 |
| 227146_at | 199.45381 | 152.23571 | -0.3897479 | 1.420122e-04 | 0.0584460282 | QSOX2 |
| 238633_at | 398.93192 | 203.47586 | -0.9712849 | 1.420368e-04 | 0.0584460282 | EPC1 |
| 213850_s_at | 783.69719 | 1550.01642 | 0.9839153 | 1.478819e-04 | 0.0584460282 | SFRS2IP |
| 219678_x_at | 311.26524 | 483.28723 | 0.6347364 | 1.500610e-04 | 0.0584460282 | DCLRE1C |
| 224976_at | 81.68481 | 52.19372 | -0.6461915 | 1.530888e-04 | 0.0584460282 | NFIA |
| 218544_s_at | 315.71474 | 178.26862 | -0.8245688 | 1.670466e-04 | 0.0584460282 | RCL1 |
| 227228_s_at | 1879.00800 | 1206.03532 | -0.6396990 | 1.728235e-04 | 0.0584460282 | CCDC88C |
| 226005_at | 710.54815 | 368.60544 | -0.9468351 | 1.854631e-04 | 0.0584460282 | UBE2G1 |

FIG. 12 Continued

| | | | | |
|---|---|---|---|---|
| 217833_at | 642.68619 | 350.38363 | -0.8751791 | 1.865547e-04 | 0.0584460282 | SYNCRIP |
| 225125_at | 958.86122 | 557.61201 | -0.7820604 | 1.922641e-04 | 0.0584460282 | MMGT1 |
| 225607_at | 237.91395 | 168.61643 | -0.4966947 | 2.199963e-04 | 0.0584460282 | CCDC43 |
| 200958_s_at | 2163.86050 | 1329.39295 | -0.7028399 | 2.253652e-04 | 0.0584460282 | SDCBP |
| 203620_s_at | 244.38864 | 132.94374 | -0.8783613 | 2.312092e-04 | 0.0584460282 | FCHSD2 |
| 232240_at | 86.36829 | 146.42032 | 0.7615756 | 2.320537e-04 | 0.0584460282 | DNHD1 |
| 203053_at | 1600.21925 | 1114.02295 | -0.5224906 | 2.335610e-04 | 0.0584460282 | BCAS2 |
| 229587_at | 130.83720 | 88.70885 | -0.5606228 | 2.382419e-04 | 0.0584460282 | UBA2 |
| 209442_x_at | 100.68873 | 176.99264 | 0.8137872 | 2.466418e-04 | 0.0584460282 | ANK3 |
| 223218_s_at | 2603.54362 | 1364.33402 | -0.9322797 | 2.539211e-04 | 0.0584460282 | NFKBIZ |
| 221699_s_at | 1144.49762 | 855.48528 | -0.4198995 | 2.572736e-04 | 0.0584460282 | DDX50 |
| 226945_at | 65.10115 | 113.11800 | 0.7970735 | 2.622337e-04 | 0.0584460282 | RHBDD1 |
| 202864_s_at | 631.46660 | 1147.68370 | 0.8619468 | 2.658674e-04 | 0.0584460282 | SP100 |
| 200740_s_at | 1222.83406 | 714.07386 | -0.7780834 | 2.659308e-04 | 0.0584460282 | SUMO3 |
| 229393_at | 282.82281 | 189.14367 | -0.5804160 | 2.684926e-04 | 0.0584460282 | L3MBTL3 |
| 223124_s_at | 1043.58504 | 662.10895 | -0.6564076 | 2.700172e-04 | 0.0584460282 | C1orf128 |
| 209376_x_at | 613.41380 | 1110.58444 | 0.8563866 | 2.789731e-04 | 0.0801148698 | SFRS21P |

FIG. 12 Continued

| Probeset | Mean of irAE | Mean of non-irAE | Log Ratio | p-value | FDR | Gene Symbol |
|---|---|---|---|---|---|---|
| 219394_at | 265.53037 | 199.61017 | -0.4116917 | 0.0001730405 | 0.744656 | PGS1 |
| 203277_at | 201.63647 | 135.06811 | -0.5780696 | 0.0002010688 | 0.744656 | DFFA |
| 208319_s_at | 1351.99631 | 2190.07323 | 0.6958879 | 0.0005154323 | 0.744656 | RBM3 |
| 217741_s_at | 1613.41275 | 2836.08192 | 0.8137836 | 0.0006594805 | 0.744656 | ZFAND5 |
| 205301_s_at | 75.73083 | 57.26210 | -0.4033004 | 0.0007768762 | 0.744656 | OGG1 |
| 219389_at | 105.01838 | 212.80938 | 1.0189199 | 0.0008510478 | 0.744656 | SUSD4 |
| 201464_x_at | 4814.56138 | 6643.44862 | 0.4645280 | 0.0008937450 | 0.744656 | JUN |
| 218973_at | 254.19890 | 195.06249 | -0.3820214 | 0.0013211551 | 0.744656 | EFTUD1 |
| 215670_s_at | 138.32966 | 86.75103 | -0.6731577 | 0.0017152289 | 0.744656 | SCAND2 |
| 219133_at | 143.70695 | 90.23563 | -0.6713607 | 0.0020174399 | 0.744656 | OXSM |
| 206571_s_at | 508.23840 | 717.15975 | 0.4967891 | 0.0020475546 | 0.744656 | MAP4K4 |
| 216027_at | 65.16729 | 175.73529 | 1.4311841 | 0.0020504723 | 0.744656 | TMX4 |
| 226713_at | 73.51571 | 140.79680 | 0.9374901 | 0.0024346397 | 0.744656 | CCDC50 |
| 209765_at | 352.50578 | 677.12802 | 0.9417817 | 0.0024992764 | 0.744656 | ADAM19 |
| 219348_at | 363.76641 | 263.30162 | -0.4662960 | 0.0025655565 | 0.744656 | USE1 |
| 207735_at | 326.29985 | 545.90050 | 0.7424397 | 0.0025817193 | 0.744656 | RNF125 |

FIG. 13

| | | | | |
|---|---|---|---|---|
| 209949_at | 142.84500 | 353.47769 | 1.3071686 | 0.0027128290 | 0.744656 | NCF2 |
| 224836_at | 148.21994 | 259.33370 | 0.8070702 | 0.0030234046 | 0.744656 | TP53INP2 |
| 207332_s_at | 640.85934 | 1071.76818 | 0.7419132 | 0.0030653199 | 0.744656 | TFRC |
| 229312_s_at | 275.08915 | 189.92979 | -0.5344330 | 0.0031405023 | 0.744656 | GKAP1 |
| 224750_at | 134.56207 | 89.91387 | -0.5816562 | 0.0031640571 | 0.744656 | RNF185 |
| 235851_s_at | 67.38955 | 124.46602 | 0.8851551 | 0.0031757582 | 0.744656 | GNAS |
| 208706_s_at | 1127.74990 | 1614.59239 | 0.5177228 | 0.0031989354 | 0.744656 | EIF5 |
| 225372_at | 584.71165 | 889.66806 | 0.6055418 | 0.0032520992 | 0.744656 | C10orf54 |
| 204834_at | 86.40856 | 210.48487 | 1.2844703 | 0.0032537882 | 0.744656 | FGL2 |
| 208881_x_at | 1309.10497 | 1813.68314 | 0.4703416 | 0.0033925472 | 0.744656 | ID1 |
| 201811_x_at | 1614.66661 | 2423.95462 | 0.5861264 | 0.0034069350 | 0.744656 | SH3BP5 |
| 1554822_at | 167.36392 | 302.46978 | 0.8538024 | 0.0035520756 | 0.744656 | PHTF2 |
| 203684_s_at | 188.32245 | 338.09582 | 0.8442272 | 0.0036962936 | 0.744656 | BCL2 |
| 207761_s_at | 54.74979 | 164.01114 | 1.5828884 | 0.0037608364 | 0.744656 | METTL7A |
| 213116_at | 111.65532 | 208.69768 | 0.9023625 | 0.0038630588 | 0.744656 | NEK3 |
| 203912_s_at | 241.41262 | 319.70799 | 0.4052537 | 0.0040568052 | 0.744656 | DNASE1L1 |
| 224862_at | 325.24555 | 501.36378 | 0.6243285 | 0.0041520117 | 0.744656 | GNAQ |

FIG. 13 Continued

| | | | | |
|---|---|---|---|---|
| 213531_s_at | 878.50450 | 611.10045 | -0.5236401 | 0.0044935679 | RAB3GAP1 | 0.744656 |
| 222893_s_at | 131.54876 | 89.02655 | -0.5632901 | 0.0046476355 | RPAP2 | 0.744656 |
| 214364_at | 243.27980 | 151.56590 | -0.6826713 | 0.0047299493 | MTERFD2 | 0.744656 |
| 235353_at | 100.33734 | 133.97110 | 0.4170631 | 0.0048836724 | KIAA0746 | 0.744656 |
| 243601_at | 127.66408 | 229.49820 | 0.8461301 | 0.0049572547 | LOC285957 | 0.744656 |
| 212515_s_at | 971.16546 | 1253.78842 | 0.3685049 | 0.0050110966 | DDX3X | 0.744656 |
| 225622_at | 455.43243 | 698.52268 | 0.6170699 | 0.0050465726 | PAG1 | 0.744656 |
| 201912_s_at | 633.20573 | 832.56395 | 0.3948868 | 0.0051666162 | GSPT1 | 0.744656 |
| 209620_s_at | 319.22579 | 268.77345 | -0.2481866 | 0.0051833894 | ABCB7 | 0.744656 |
| 202768_at | 796.19366 | 1751.36584 | 1.1372892 | 0.0052857940 | FOSB | 0.744656 |
| 230296_at | 292.82936 | 188.31407 | -0.6369194 | 0.0055551247 | C16orf52 | 0.744656 |
| 1556126_s_at | 120.84274 | 178.45812 | 0.5624548 | 0.0056217169 | GPATCH2 | 0.744656 |
| 215286_s_at | 158.65051 | 287.25256 | 0.8564676 | 0.0056930674 | PHTF2 | 0.744656 |
| 236609_at | 73.43312 | 135.94038 | 0.8884713 | 0.0059030664 | LOC100129592 | 0.744656 |
| 229257_at | 98.99386 | 139.08736 | 0.4905804 | 0.0059149518 | TNRC18 | 0.744656 |
| 208896_at | 405.00205 | 510.27662 | 0.3333503 | 0.0059362392 | DDX18 | 0.744656 |
| 205186_s_at | 1451.76924 | 2080.52054 | 0.5191324 | 0.0064333215 | SFPQ | 0.744656 |

FIG. 13 Continued

| Probeset | Mean of irAE | Mean of non-irAE | Log Ratio | p-value | FDR | Gene Symbol |
|---|---|---|---|---|---|---|
| 228857_at | 102.23955 | 169.39587 | 0.7284452 | 0.0002844686 | 1 | GNL1 |
| 225446_at | 317.62690 | 459.96796 | 0.5342003 | 0.0004581926 | 1 | BRWD1 |
| 225372_at | 548.29599 | 812.85667 | 0.5680461 | 0.0006049582 | 1 | C10orf54 |
| 1559975_at | 406.63676 | 702.89043 | 0.7895592 | 0.0006755935 | 1 | BTG1 |
| 201464_x_at | 4880.45038 | 6798.61123 | 0.4782258 | 0.0008262628 | 1 | JUN |
| 201586_s_at | 1336.84904 | 2121.07838 | 0.6659614 | 0.0009265189 | 1 | SFPQ |
| 223766_at | 200.52410 | 313.43074 | 0.6443710 | 0.0009683080 | 1 | LOC100133130 |
| 203912_s_at | 204.79396 | 285.59652 | 0.4798052 | 0.0009844611 | 1 | DNASE1L1 |
| 232044_at | 642.91435 | 922.42509 | 0.5208052 | 0.0011894623 | 1 | RBBP6 |
| 204959_at | 61.11106 | 174.14225 | 1.5107610 | 0.0012314537 | 1 | MNDA |
| 217741_s_at | 1611.17487 | 2864.91608 | 0.8303798 | 0.0013690752 | 1 | ZFAND5 |
| 209334_s_at | 63.20498 | 93.18786 | 0.5601038 | 0.0014427809 | 1 | PSMD9 |
| 217672_x_at | 82.14066 | 123.35008 | 0.5865902 | 0.0014622382 | 1 | EIF1 |
| 202147_s_at | 346.90664 | 550.07112 | 0.6650707 | 0.0015990987 | 1 | IFRD1 |
| 216027_at | 76.47126 | 207.83963 | 1.4424811 | 0.0017377342 | 1 | TMX4 |
| 208706_s_at | 1019.39408 | 1551.03395 | 0.6055184 | 0.0020840885 | 1 | EIF5 |

FIG. 14

| | | | | |
|---|---|---|---|---|
| 213758_at | 172.27603 | 366.59746 | 1.0894749 | 0.0023461452 | 1 | COX4I1 |
| 228304_at | 92.14672 | 154.80789 | 0.7484743 | 0.0023461511 | 1 | RBM43 |
| 208248_x_at | 751.94830 | 1191.13206 | 0.6636280 | 0.0023504732 | 1 | APLP2 |
| 1555745_a_at | 188.11886 | 836.70658 | 2.1530773 | 0.0025829309 | 1 | LYZ |
| 203684_s_at | 117.03744 | 252.23548 | 1.1078011 | 0.0026102452 | 1 | BCL2 |
| 1555996_s_at | 205.99600 | 465.46451 | 1.1760548 | 0.0026528681 | 1 | EIF4A2 |
| 219094_at | 233.09504 | 416.80866 | 0.8384670 | 0.0028702782 | 1 | ARMC8 |
| 235851_s_at | 67.05925 | 113.50556 | 0.7592547 | 0.0029809204 | 1 | GNAS |
| 206571_s_at | 388.69770 | 575.54951 | 0.5662915 | 0.0031271739 | 1 | MAP4K4 |
| 1554248_at | 220.76778 | 316.47746 | 0.5195732 | 0.0032363502 | 1 | ZNF638 |
| 209092_s_at | 704.28122 | 930.63924 | 0.4020704 | 0.0032780407 | 1 | GLOD4 |
| 202646_s_at | 1741.92612 | 2358.66662 | 0.4372881 | 0.0034420748 | 1 | CSDE1 |
| 1554906_a_at | 85.34310 | 164.83163 | 0.9496468 | 0.0035491006 | 1 | MPHOSPH6 |
| 211207_s_at | 154.82960 | 280.38225 | 0.8567137 | 0.0036184299 | 1 | ACSL6 |
| 208881_x_at | 1386.49325 | 1981.03992 | 0.5148174 | 0.0036362506 | 1 | IDI1 |
| 211324_s_at | 54.26408 | 133.56376 | 1.2994591 | 0.0039075045 | 1 | RGPD5 |
| 212225_at | 727.46359 | 1588.03922 | 1.1262996 | 0.0040266556 | 1 | EIF1 |

FIG. 14 Continued

| | | | | |
|---|---|---|---|---|
| 204615_x_at | 1490.21450 | 2031.24331 | 0.4468431 | 0.0041829386 | 1 | ID1 |
| 215286_s_at | 93.10606 | 154.05892 | 0.7265353 | 0.0044637490 | 1 | PHTF2 |
| 238509_at | 433.52090 | 755.75244 | 0.8018122 | 0.0047605806 | 1 | CUL1 |
| 1560770_at | 135.38018 | 406.98270 | 1.5879509 | 0.0052443177 | 1 | PABPC1 |
| 208704_x_at | 637.69097 | 1005.63008 | 0.6571703 | 0.0053115956 | 1 | APLP2 |
| 227768_at | 262.77738 | 350.17357 | 0.4142291 | 0.0053150073 | 1 | ZNF407 |
| 207735_at | 347.32970 | 558.64515 | 0.6856264 | 0.0054149869 | 1 | RNF125 |
| 212875_s_at | 88.52207 | 122.26653 | 0.4659203 | 0.0056062924 | 1 | C2CD2 |
| 200731_s_at | 359.62301 | 702.92366 | 0.9668827 | 0.0056635688 | 1 | PTP4A1 |
| 219133_at | 138.75661 | 100.22795 | -0.4692716 | 0.0059549424 | 1 | OXSM |
| 227622_at | 389.95721 | 588.41578 | 0.5935201 | 0.0059679954 | 1 | PCF11 |
| 204565_at | 255.47465 | 196.27183 | -0.3803270 | 0.0064091905 | 1 | ACOT13 |
| 224164_at | 55.67101 | 86.50407 | 0.6358416 | 0.0065143854 | 1 | TPM3 |
| 213524_s_at | 81.48644 | 224.59582 | 1.4626993 | 0.0067588977 | 1 | G0S2 |
| 1553736_at | 99.83547 | 154.57247 | 0.6306591 | 0.0068695000 | 1 | ZFC3H1 |
| 222021_x_at | 838.21744 | 692.44354 | -0.2756281 | 0.0069969419 | 1 | SDHALP1 |
| 200892_s_at | 1730.30887 | 2500.87946 | 0.5314059 | 0.0071100288 | 1 | TRA2B |

*FIG. 14 Continued*

PREDICTIVE BIOMARKERS FOR CTLA-4 BLOCKADE THERAPY AND FOR PD-1 BLOCKADE THERAPY

CROSS-REFERENCE TO RELATED APPLICATIONS

This application is a 371 application of International Application No. PCT/US2013/032254, filed Mar. 15, 2013, which claims benefit of U.S. Provisional Application No. 61/644,004, filed May 8, 2012, and U.S. Provisional Application No. 61/644,988, filed May 9, 2012.

STATEMENT REGARDING FEDERALLY SPONSORED RESEARCH OR DEVELOPMENT

This invention was made with Government Support under Grant No. R01 CA 109307 and Grant No. CA 129594 awarded by the National Institutes of Health (NIH). The Government has certain rights in the invention.

FIELD OF THE INVENTION

The invention is generally related to the field of predictive biomarkers, more particularly to biomarkers predictive for CTLA-4 blockade treatment and to biomarkers predictive for PD-1 blockade treatment.

BACKGROUND OF THE INVENTION

T cells play a pivotal role in anti-tumor responses, in the development of immune tolerance to self, and in autoimmunity. Cytotoxic T Lymphocyte-Associated antigen 4 (CTLA-4) is a surface receptor on T lymphocytes that down-regulates pathways of T-cell activation (Melero I, et al. *Nat Rev Cancer.* 7:95-106 (2007)), serving as an immune check point molecule. It is expressed intracellularly in resting T cells, transported to the T cell surface after activation of the T cell receptor (TCR). TCR engagement leads to tyrosine phosphorylation of CTLA-4 via the SRC kinase and releases it from AP50, resulting in its surface expression within 48 hours of T cell activation, leading to T cell tolerance and anergy. CTLA-4 expression is associated with decreased proliferation with cell cycle arrest at the $G_1$-S interface and diminished cytokine secretion (Chambers C A, et al. *Annu Rev Immunol.* 19:565-94 (2001); Greenwald R J, et al. *Immunity.* 14:145-55 (2001)). It decreases cell proliferation through the inhibition of mitogen-activated (MAP) kinases but promotes T cell survival through the binding of phosphoinositol-3 kinase and activating protein kinase B (PKB/AKT) resulting in T cell anergy and tolerance without T cell death (Schneider H, et al. *PLoS One.* 3:e3842 (2008)). CTLA-4 signals suppress both $CD4^+$ and $CD8^+$ T cell responses via a tyrosine-based inhibitory motif (Egen J G, et al. *Immunity.* 16:23-35 (2002); Egen J G, et al. *Nat Immunol.* 3:611-8 (2002)).

CTLA-4 blockade has antitumor activity in mice, and important effects on breaking tolerance (Egen J G, et al. *Nat Immunol.* 3:611-8 (2002); Leach D R, et al. *Science.* 271: 1734-6 (1996); Quezada S A, et al. *J Clin Invest.* 116:1935-45 (2006); Chen L, et al. *Cell.* 71:1093-102 (1992); van Elsas A, et al. *J Exp Med.* 190:355-66 (1999)). In experiments with B16 melanoma, a therapeutic effect induced by CTLA-4 blockade with a vaccine was associated with development of autoimmune vitiligo, suggesting that expansion of T cells recognizing melanocyte lineage antigens was associated with the therapeutic effect. Several autoimmune diseases were associated with single nucleotide polymorphisms in the CTLA-4 gene, including hypothyroidism and type 1 diabetes (Ueda H, et al. *Nature.* 423:506-11 (2003)). In $CTLA-4^{-/-}$ knock-out mice, expansion of lymphocytes with diffuse lymphadenopathy and lymphoid infiltration of different organs occurs, consistent with a generalized expansion of T cells (Waterhouse P, et al. *Science.* 270:985-8 (1995)). Similarly, both preclinical and clinical data indicate that CTLA-4 blockade results in activation and expansion of total $CD4^+$ and $CD8^+$ effector T cells (Wolchok J D, et al. *Oncologist.* 13 Suppl 4:2-9 (2008)), and breaking of self-tolerance has been shown in patients, as evidenced by the occurrence of immune-related adverse events (irAEs) observed with two different CTLA-4 antibodies, ipilimumab (Bristol Myers Squibb, Princeton, N.J., USA) (Maker A V, et al. *J Immunol.* 175:7746-54 (2005)) and tremelimumab (Pfizer, New York, N.Y., USA) (Ribas A, et al. *Oncologist.* 13 Suppl 4:10-5 (2008)).

Ipilimumab, a fully human, CTLA-4 blocking $IgG_1$ monoclonal antibody induces long-lasting clinical responses in a minority of patients with metastatic melanoma (Wolchok J D, et al. *Lancet Oncol.* 11:155-64 (2008); Weber J, et al. *Clin Cancer Res.* 15:5591-8 (2009); Weber J. *Cancer Immunol Immunother.* 58:823-30 (2009); Fong L, et al. *J Clin Oncol.* 26:5275-83 (2008); Phan G Q, et al. *Proc Natl Acad Sci USA.* 100:8372-7 (2003); O'Day S J, et al. *Ann Oncol.* 21:1712-7 (2010)). Ipilimumab, with or without a gp100 peptide vaccine, compared with gp100 vaccine alone, improved overall survival (OS) in patients with previously treated metastatic melanoma (Hodi F S, et al. *N Engl J Med.* 363:711-23 (2010)). Ipilimumab combined with dacarbazine improved overall survival in previously untreated patients compared to dacarbazine alone (Robert C, et al. *N Engl J Med.* 364:2517-26 (2011)). These were the first randomized Phase III trials to demonstrate a significant survival impact for patients with metastatic melanoma, yet few studies have documented pharmacodynamic markers of the impact of ipilimumab. An increase in the absolute lymphocyte count (ALC) after 2 or 3 doses of the drug at weeks 4 and 7 has been documented (Yuan J, et al. *Cancer Immun.* 10:1 (2010)), and may correlate with an improved outcome; increased $CD4^+$ $HLA-DR^+$ T cells have been shown in several studies to occur after ipilimumab therapy (Sanderson K, et al. *J Clin Oncol.* 23:741-50 (2005); Sarnaik A A, et al. *Clin Cancer Res.* 17(4):896-906 (2010)); in several small cohort studies of brief duration, ipilimumab treatment increased the frequency of $CD4^+ICOS^{hi}$ T cells in tumors and in the circulation, and also induced antibody reactivity against the cancer-testis antigen NY-ESO-1 Carthon B C, et al. *Clin Cancer Res.* 16:2861-71 (2010); Chen H, et al. *Proc Natl Acad Sci USA.* 106:2729-34 (2009)). CTLA-4 abrogating antibodies do not alter vaccine specific immune responses (Attia P, et al. *J Clin Oncol.* 23:6043-53 (2005)) and even when administered with a peptide vaccine, tumor antigen specific responses were only modestly increased (Attia P, et al. *J Clin Oncol.* 23:6043-53 (2005); Ribas A, et al. *Clin Cancer Res.* 15:390-9 (2009)). Recall responses to viral and other antigens were not altered by ipilimumab. In patients receiving another CTLA-4 abrogating antibody, tremelimumab, the ratio of intratumoral T cells to FoxP3 positive T regulatory cells was increased after treatment only in regressing lesions (Ribas A, et al. *Clin Cancer Res.* 15:390-9 (2009)), suggesting a therapeutic impact of CTLA-4 abrogation on T cells infiltrating the tumor. The same investigators also demonstrated that peripheral blood Th17 cells were induced by tremelimumab (von Euw E, et al. *J Transl Med.* 7:35 (2009)), and that certain signaling pathways downstream of the TCR and cytokine receptor were also influenced by CTLA-4 blockade, such as increased pp38, pSTAT1 and pSTAT3, and decreased pLck, pERK1/2 and pSTAT5 levels (Comin-Anduix B, et al. *PLoS One.* 5:e12711 (2010)). CTLA-4 blockade also induced cell proliferation in the spleen, a secondary lymphoid organ, shown by molecular imaging with the PET probe 18F-FLT (Ribas A, et al. *J Nucl Med.* 51:340-6 (2010)). They also reported significantly increased intratumoral CD8$^+$ T cell infiltration and CD4$^+$ T cells infiltration, demonstrated the activation of lymphocytes within tumor sites, as increase of HLA-DR and CD45RO double positive cells in post tremelimumab biopsies (Huang R R, et al. *Clin Cancer Res.* 17:4101-9 (2011)) and increased expression of FoxP3.

To date, the precise molecular basis and mechanisms of action of ipilimumab have not been documented systematically in vivo. There is a critical need for biomarkers of the effects of ipilimumab as well as predictive biomarkers for clinical outcome and induction of irAE.

PD-1 blocking antibody (BMS-936558) therapy has shown antitumor activity and clinical benefit in melanoma patients. The precise molecular basis and mechanisms of PD-1 blockade in vivo have not been documented and there are few biomarker associated with clinical benefit. There is a critical need for biomarkers of the effects of PD-1 blockade treatment as well as predictive biomarkers for clinical outcome.

SUMMARY OF THE INVENTION

Biomarkers have been identified for predicting the efficacy, risk of relapse, risk of an immune related adverse event (irAE), or combination thereof for a CTLA-4 blockade treatment, such as ipilimumab, in a subject with a cancer, such as melanoma. Methods are therefore disclosed that involve assaying peripheral blood mononuclear cells (PBMCs) from a subject diagnosed with a cancer, such as a melanoma, for expression of one or more of the following biomarkers: CD8, Ki67, eomesodermin (EOMES), transforming growth factor beta receptor III (TGFβR3), C—C chemokine receptor type 7 (CCR7), CD4, CD71, and CD109. For example, expression can be assayed for one or more of the following biomarkers: CD8, Ki67, eomesodermin (EOMES), transforming growth factor beta receptor III (TGFβR3), and C—C chemokine receptor type 7 (CCR7). For example, the method can involve assaying the PBMCs for the presence of (a) CD8, Ki67, and EOMES; (b) CD8 and EOMES; (c) CD8 and TGFβR3; (d) CD4 and CCR7; (e) CD4, Ki67, and EOMES; (f) CD4 and CD71; or (g) CD8 and CD109. For example, the method can involve assaying the PBMCs for the presence of (a) CD8, Ki67, and EOMES; (b) CD8 and EOMES; (c) CD8 and TGFβR3; (d) CD4 and CCR7; or (e) CD4, Ki67, and EOMES.

Also disclosed are methods of treating a subject diagnosed with melanoma with a CTLA-4 blockade treatment if the expression level of one or more of the biomarkers listed in FIGS. 11, 12, 13, and 14 are at or beyond a threshold level, such as a level that is greater than or less than (depending on the marker) a reference level. For example, the ratio of responder (NED or non-irAE) to nonresponder (Relapse or irAE) can be used as, or to define a threshold level or a reference level.

Also disclosed are methods of not treating a subject with a CTLA-4 blockade treatment if the expression level of one or more of the biomarkers listed in Tables 10, 11, 12, and 13 are at or beyond a threshold level, such as a level that is greater than or less than (depending on the marker) a reference level. For example, the ratio of responder (NED or non-irAE) to nonresponder (Relapse or irAE) can be used as, or to define a threshold level or a reference level.

In some embodiments, the frequency of Ki67$^+$EOMES$^+$CD8$^+$ T cells in CD8$^+$ T cells in the PBMCs is inversely associated with the risk of relapse after CTLA-4 blockade treatment. For example, a frequency of Ki67$^+$EOMES$^+$CD8$^+$ T cells in CD8$^+$ T cells in the PBMCs less than about 2.11%, preferably less than about 2.0%, more preferably less than about 1.8%, most preferably less than about 1.6%, is an indication that the subject is at risk of relapse after CTLA-4 blockade treatment. Likewise, a frequency of Ki67$^+$EOMES$^+$CD8$^+$ T cells in CD8$^+$ T cells in the PBMCs greater than about 2.2%, preferably greater than about 2.3%, more preferably greater than about 2.4%, most preferably greater than about 2.5%, is an indication that the subject will have relapse free survival after CTLA-4 blockade treatment.

In some embodiments, the frequency of EOMES$^+$CD8$^+$ T cells in CD8$^+$ T cells in the PBMCs is inversely associated with the risk of relapse after CTLA-4 blockade treatment. For example, a frequency of EOMES$^+$CD8$^+$ T cells in CD8$^+$ T cells in the PBMCs less than about 55.6%, preferably less than about 50%, more preferably less than about 45%, most preferably less than about 40%, is an indication that the subject is at risk of relapse after CTLA-4 blockade treatment. Likewise, a frequency of EOMES$^+$CD8$^+$ T cells in CD8$^+$ T cells in the PBMCs greater than about 56%, preferably greater than about 57%, more preferably greater than about 59%, most preferably greater than about 61% is an indication that the subject will have relapse free survival after CTLA-4 blockade treatment.

In some embodiments, the expression level of CCR7 on CD4$^+$ T cells in the PBMCs is directly associated with the risk of relapse after CTLA-4 blockade treatment. For example, an expression level of CCR7 on CD4$^+$ T cells in the PBMCs greater than about 2402, preferably greater than about 2500, more preferably greater than about 2700, most preferably greater than about 2900, is an indication that the subject is at risk of relapse after CTLA-4 blockade treatment. Likewise, an expression level of CCR7 on CD4$^+$ T cells in the PBMCs less than about 2400, preferably less than about 2300, more preferably less than about 2100, most preferably less than about 1900, is an indication that the subject will have relapse free survival after CTLA-4 blockade treatment.

In some embodiments, the frequency of Ki67$^+$EOMES$^+$CD4$^+$ T cells in CD4$^+$ T cells in the PBMCs is inversely associated with the risk of an immune related adverse event (irAE) after CTLA-4 blockade treatment. For example, a frequency of Ki67$^+$EOMES$^+$CD4$^+$ T cells in CD4$^+$ T cells in the PBMCs less than about 0.446%, preferably less than about 0.4%, more preferably less than about 0.35%, most preferably less than about 0.3%, is an indication that the subject is at risk of an immune related adverse event (irAE) after CTLA-4 blockade treatment. Likewise, a frequency of Ki67$^+$EOMES$^+$CD4$^+$ T cells in CD4$^+$ T cells in the PBMCs greater than about 0.45%, preferably greater than about 0.5%, more preferably greater than about 0.6%, most preferably greater than about 0.7%, is an indication that the subject will not have an irAE after CTLA-4 blockade treatment.

In some embodiments, the expression level of TGFβR3 on CD8$^+$ T cells in the PBMCs is directly associated with risk of an immune related adverse event (irAE) after CTLA-4 blockade treatment. For example, an expression level of TGFβR3 on CD8$^+$ T cells in the PBMCs greater than about 527, preferably greater than about 600, more preferably greater than about 700, most preferably greater than about 1000, is an indication that the subject is at risk of an immune related adverse event (irAE) after CTLA-4 blockade treatment. Likewise, an expression level of TGFβR3 on $CD8^+$ T cells in the PBMCs less than about 525, preferably less than about 500, more preferably less than about 450, most preferably less than about 400, is an indication that the subject will not have an immune related adverse event (irAE) after CTLA-4 blockade treatment.

In some embodiments, the expression level of CD71 on $CD4^+$ T cells in the PBMCs is inversely associated with risk of an immune related adverse event (irAE) after CTLA-4 blockade treatment.

In some embodiments, the frequency of $CD109^+CD8^+$ T cells in $CD8^+$ T cells in the PBMCs is directly associated with the risk of relapse after CTLA-4 blockade treatment. For example, a frequency of $CD109^+CD8^+$ T cells in $CD8^+$ T cells in the PBMCs greater than about 0.7315%, preferably greater than about 0.8%, more preferably greater than about 1.0%, most preferably greater than about 2.0%, is an indication that the subject is at risk of relapse after CTLA-4 blockade treatment. Likewise, a frequency of $CD109^+CD8^+$ T cells in $CD8^+$ T cells in the PBMCs less than about 0.7316%, preferably less than about 0.7%, more preferably less than about 0.6%, most preferably less than about 0.5% is an indication that the subject will have relapse free survival after CTLA-4 blockade treatment.

In some embodiments, the frequency of $CD71^+CD4^+$ T cells in $CD4^+$ T cells in the PBMCs is inversely associated with the risk of an immune related adverse event (irAE) after CTLA-4 blockade treatment. For example, a frequency of $CD71^+CD4^+$ T cells in $CD4^+$ T cells in the PBMCs less than about 2.80%, preferably less than about 2.5%, more preferably less than about 2.0%, most preferably less than about 1.5%, is an indication that the subject is at risk of an immune related adverse event (irAE) after CTLA-4 blockade treatment. Likewise, a frequency of $CD71^+CD4^+$ T cells in $CD4^+$ T cells in the PBMCs greater than about 2.8%, preferably greater than about 3.0%, more preferably greater than about 3.5%, most preferably greater than about 4%, is an indication that the subject will not have an irAE after CTLA-4 blockade treatment.

The disclosed method can further involve using the biomarkers to select subjects suitable for treatment with a CTLA-4 blockade agent, such as ipilimumab or tremelimumab, or a treatment other than a CTLA-4 blockade treatment, such as a neoplastic agent, or a combination of CTLA-4 blockade agent and another treatment.

For example, in some embodiments, the method involves selecting a subject for CTLA-4 blockade treatment, another treatment, or a combination thereof if (a) if the frequency of $Ki67^+EOMES^+CD8^+$ T cells in the subject's $CD8^+$ T cells is at least about 2.2%, preferably at least about 2.3%, more preferably at least about 2.4%, most preferably at least about 2.5%; (b) if the frequency of $EOMES^+CD8^+$ T cells in the subject's $CD8^+$ T cells is at least 56%, preferably at least about 57%, more preferably at least about 59%, most preferably at least about 61%; (c) if the expression level of CCR7 on $CD4^+$ T cells in the subject is lower than about 2400, preferably lower than about 2300, more preferably lower than about 2100, most preferably lower than about 1900; (d) if the frequency of $Ki67^+EOMES^+CD4^+$ T cells in the subject's $CD4^+$ T cells is at least about 0.45%, preferably at least about 0.5%, more preferably at least about 0.6%, most preferably at least about 0.7%; (e) if the expression level of TGFβR3 on $CD8^+$ T cells in the subject is lower than about 525; preferably lower than about 500, more preferably lower than about 450, most preferably lower than about 400; (f) the expression level of CD109 on $CD8^+$ T cells is less than 0.7316%, preferably less than about 0.7%, more preferably less than about 0.6%, most preferably less than about 0.5%; (g) the frequency of $CD71^+CD4^+$ T cells in $CD4^+$ T cells in the PBMCs is at least 2.80%, preferably greater than about 3.0%, more preferably greater than about 3.5%, most preferably greater than about 4%; or any combination thereof.

Therefore, in these embodiments, the subject is not treated with CTLA-4 blockade treatment, is treated with another treatment, or a combination thereof if (a) the frequency of $Ki67^+EOMES^+CD8^+$ T cells is less than about 2.11%, preferably less than about 2.0%, more preferably less than about 1.8%, most preferably less than about 1.6%; (b) the frequency of $EOMES^+CD8^+$ T cells is less than about 55.6%, preferably less than about 50%, more preferably less than about 45%, most preferably less than about 40%; (c) the expression level of CCR7 on $CD4^+$ T cells is greater than about 2402, preferably greater than about 2500, more preferably greater than about 2700, most preferably greater than about 2900; (d) the frequency of $Ki67^+EOMES^+CD4^+$ T cells is less than about 0.446%, preferably less than about 0.4%, more preferably less than about 0.35%, most preferably less than about 0.3%; (e) the expression level of TGFβR3 on $CD8^+$ T cells is greater than about 527, preferably greater than about 600, more preferably greater than about 700, most preferably greater than about 1000; (f) the frequency of $CD109^+CD8^+$ T cells in $CD8^+$ T cells is greater than about 0.7315%, preferably greater than about 0.8%, more preferably greater than about 1.0%, most preferably greater than about 2.0%; (g) the frequency of $CD71^+CD4^+$ T cells in $CD4^+$ T cells is less than about 2.80%, preferably less than about 2.5%, more preferably less than about 2.0%, most preferably less than about 1.5% or any combination thereof.

Methods of treating subjects diagnosed with melanoma are also disclosed that involve treating the subject with a CTLA-4 blockade treatment, another treatment, or a combination thereof (a) if the frequency of $Ki67^+EOMES^+CD8^+$ T cells in the subject's $CD8^+$ T cells is at least about 2.2%, preferably at least about 2.3%, more preferably at least about 2.4%, most preferably at least about 2.5%; (b) if the frequency of $EOMES^+CD8^+$ T cells in the subject's $CD8^+$ T cells is at least 56%, preferably at least about 57%, more preferably at least about 59%; (c) if the expression level of CCR7 on $CD4^+$ T cells in the subject is lower than about 2400, preferably lower than about 2300, more preferably lower than about 2100, most preferably lower than about 1900; (d) if the frequency of $Ki67^+EOMES^+CD4^+$ T cells in the subject's $CD4^+$ T cells is at least about 0.45%, preferably at least about 0.5%, more preferably at least about 0.6%, most preferably at least about 0.7%; (e) if the expression level of TGFβR3 on $CD8^+$ T cells in the subject is lower than about 525; preferably lower than about 500, more preferably lower than about 450, most preferably lower than about 400; (f) the expression level of CD109 on $CD8^+$ T cells is less than 0.7316%, preferably less than about 0.7%, more preferably less than about 0.6%, most preferably less than about 0.5%; (g) the frequency of $CD71^+CD4^+$ T cells in $CD4^+$ T cells in the PBMCs is at least 2.80%, preferably greater than about 3.0%, more preferably greater than about 3.5%, most preferably greater than about 4%; or any combination thereof.

Biomarkers have been identified for predicting the efficacy and clinical benefit for a PD-1 blockade treatment, such as a PD-1 blocking antibody, in a subject with a cancer, such as melanoma. Methods are therefore disclosed that involve assaying peripheral blood mononuclear cells (PBMCs) from a subject diagnosed with a cancer, such as a melanoma, for expression of one or more of the biomarkers listed in Tables 8 and 9.

Disclosed are methods comprising assaying peripheral blood mononuclear cells (PBMCs) from a subject diagnosed with melanoma for expression of CD8 and one or a combination of markers in Tables 8 and 9, where, depending on the marker, the level of expression of certain markers on $CD8^+$ T cells in the PBMCs of the subject prior to PD-1 blockade treatment or a change in the expression level of certain markers on $CD8^+$ T cells in the PBMCs following PD-1 blockade treatment indicate the expected clinical benefit of PD-1 blockade treatment of the subject.

Also disclosed are methods of treating a subject diagnosed with melanoma with a PD-1 blockade treatment if the expression level of one or more of the biomarkers listed in Tables 8 and 9 are at or beyond a threshold level, such as a level that is greater than or less than (depending on the marker) a reference level.

Also disclosed are methods of treating a subject diagnosed with melanoma with a treatment other than a PD-1 blockade treatment, or with both a PD-1 blockade treatment and a different treatment, if the expression level of one or more of the biomarkers listed in Tables 8 and 9 are at or beyond a threshold level, such as a level that is greater than or less than (depending on the marker) a reference level.

In some forms of the methods, the PBMCs can be assayed prior to PD-1 blockade treatment of the subject. Expression levels measured prior to PD-1 blockade treatment can be referred to as baseline expression. In some forms of the methods, the expression prior the PD-1 blockade treatment is compared to a reference level of expression.

In some forms of the methods, the PBMCs can also be assayed following PD-1 blockade treatment of the subject. Expression following the PD-1 blockade treatment can be compared to the expression prior to the PD-1 blockade treatment. Depending on the marker, a change in the expression level of certain markers on $CD8^+$ T cells in the PBMCs following PD-1 blockade treatment indicate the expected clinical benefit of PD-1 blockade treatment of the subject. In some forms, a change in expression level can indicate that PD-1 blockade treatment should be continued with the subject.

Also disclosed are methods of selecting a subject for PD-1 blockade treatment if the expression level of one or more of the biomarkers listed in Tables 8 and 9 are at or beyond a threshold level, such as a level that is greater than or less than (depending on the marker) a reference level.

Also disclosed are methods of not treating a subject with a PD-1 blockade treatment if the expression level of one or more of the biomarkers listed in Tables 8 and 9 are at or beyond a threshold level, such as a level that is greater than or less than (depending on the marker) a reference level.

In some forms of the methods, the PD-1 blockade treatment can be treatment with a PD-1 blocking antibody. In some forms of the methods, the PD-1 blockade treatment can be treatment with PD-1 blocking antibody BMS-936558 or BMS-936559.

For example, expression of one or a combination of Phosphatase and tensin homolog (PTEN), GATA zinc finger domain containing 1 (GATAD1), Natural killer-tumor recognition sequence (NKTR), CD276 molecule (B7-H3) (CD276), NOL1/NOP2/Sun domain family, member 6 (NSUN6), Cell division cycle and apoptosis regulator 1 (CCAR1), SET and MYND domain containing 2 (SMYD2), F-box protein 9 (FBXO9), Non-protein coding RNA 153 (NCRNA00153), Neutral sphingomyelinase activation associated factor (NSMAF), Pyrimidinergic receptor P2Y, G-protein coupled, 4 (P2RY4), REST corepressor 2 (RCOR2), Negative regulator of ubiquitin-like proteins 1 (NUB1), Fc receptor-like 2 (FCRL2), Nuclear casein kinase, cyclin-dependent kinase substrate 1 (NUCKS1), SHC transforming protein 2 (SHC2), Stearoyl-CoA desaturase 5 (SCD5), Ubiquitin specific peptidase 9, Y-linked (USP9Y), Heat shock 60 kDa protein 1 (chaperonin) (HSPD1), Cytokine inducible SH2-containing protein (CISH), Kruppel-like factor 12 (KLF12), Neutrophil cytosolic factor 4, 40 kDa (NCF4), Splicing factor, arginine/serine-rich 7, 35 kDa (SFRS7), CDC14 cell division cycle 14 homolog A (*S. cerevisiae*) (CDC14A), Mitogen-activated protein kinase kinase 5 (MAP2K5), Interleukin 11 receptor, alpha (IL11RA), Myeloid/lymphoid or mixed-lineage leukemia (MLL), HSPB (heat shock 27 kDa) associated protein 1 (HSPBAP1), Mitogen-activated protein kinase kinase kinase 4 (MAP4K4), Helicase, lymphoid-specific (HELLS), C1q and tumor necrosis factor related protein 3 (C1QTNF3), Ubiquitin-conjugating enzyme E2D 1 (UBE2D1), Fas apoptotic inhibitory molecule 3 (FAIM3), Interferon-induced protein 44 (IF144), H2B histone family, member M (H2BFM), GATA zinc finger domain containing 1 (GATAD1), Caspase 8, apoptosis-related cysteine peptidase (CASP8), Suppressor of cytokine signaling 1 (SOCS1), Programmed cell death 6 (PDCD6), LAG1 homolog, ceramide synthase 6 (LASS6), Growth arrest DNA-damage-inducible, beta (GADD45B), Early growth response 2 (EGR2), Early growth response 1 (EGR1), Growth arrest, DNA-damage-inducible, g (GADD45G), CDC28 protein kinase regulatory subunit 2 (CKS2), Cyclin-dependent kinase inhibitor 1C (CDKN1C), Immediate early response 5 (IER5), Inhibitor of growth family, member 1 (ING1), Interferon induced with helicase C domain 1 (IFIH1), Interferon, gamma (IFNG), Immediate early response 5-like (IER5L), Cancer/testis antigen 1 (NY-ESO-1), and Melanoma antigen recognized by T-cells 1 (MART-1) can be detected, measured, assayed, assessed, etc.

The levels of expression of the markers can indicate the efficacy, predicted efficacy, likelihood of clinical benefit, prognosis, etc., of a subject treated with a PD-1 blockade treatment. For example, the expression level of PTEN on $CD8^+$ T cells in the PBMCs is positively associated with the expected clinical benefit of PD-1 blockade treatment of the subject; the expression level of GATAD1 on $CD8^+$ T cells in the PBMCs is positively associated with the expected clinical benefit of PD-1 blockade treatment of the subject; the expression level of NKTR on $CD8^+$ T cells in the PBMCs is positively associated with the expected clinical benefit of PD-1 blockade treatment of the subject; the expression level of CD276 on $CD8^+$ T cells in the PBMCs is negatively associated with the expected clinical benefit of PD-1 blockade treatment of the subject; the expression level of NSUN6 on $CD8^+$ T cells in the PBMCs is positively associated with the expected clinical benefit of PD-1 blockade treatment of the subject; the expression level of CCAR1 on $CD8^+$ T cells in the PBMCs is positively associated with the expected clinical benefit of PD-1 blockade treatment of the subject; the expression level of SMYD2 on $CD8^+$ T cells in the PBMCs is positively associated with the expected clinical benefit of PD-1 blockade treatment of the subject; the expression level of FBXO9 on $CD8^+$ T cells in the PBMCs is positively associated with the expected clinical benefit of PD-1 blockade treatment of the subject; the expression level of NCRNA00153 on $CD8^+$ T cells in the PBMCs is positively associated with the expected clinical benefit of PD-1 blockade treatment of the subject; the expression level of NSMAF on CD8+ T cells in the PBMCs is positively associated with the expected clinical benefit of PD-1 blockade treatment of the subject; the expression level of P2RY4 on CD8+ T cells in the PBMCs is negatively associated with the expected clinical benefit of PD-1 blockade treatment of the subject; the expression level of RCOR2 on CD8+ T cells in the PBMCs is negatively associated with the expected clinical benefit of PD-1 blockade treatment of the subject; the expression level of NUB1 on CD8+ T cells in the PBMCs is negatively associated with the expected clinical benefit of PD-1 blockade treatment of the subject; the expression level of FCRL2 on CD8+ T cells in the PBMCs is negatively associated with the expected clinical benefit of PD-1 blockade treatment of the subject; the expression level of NUCKS1 on CD8+ T cells in the PBMCs is negatively associated with the expected clinical benefit of PD-1 blockade treatment of the subject; the expression level of SHC2 on CD8+ T cells in the PBMCs is negatively associated with the expected clinical benefit of PD-1 blockade treatment of the subject; the expression level of SCD5 on CD8+ T cells in the PBMCs is negatively associated with the expected clinical benefit of PD-1 blockade treatment of the subject; the expression level of USP9Y on CD8+ T cells in the PBMCs is positively associated with the expected clinical benefit of PD-1 blockade treatment of the subject; the expression level of HSPD1 on CD8+ T cells in the PBMCs is positively associated with the expected clinical benefit of PD-1 blockade treatment of the subject; the expression level of CISH on CD8+ T cells in the PBMCs is positively associated with the expected clinical benefit of PD-1 blockade treatment of the subject; the expression level of KLF12 on CD8+ T cells in the PBMCs is positively associated with the expected clinical benefit of PD-1 blockade treatment of the subject; the expression level of NCF4 on CD8+ T cells in the PBMCs is positively associated with the expected clinical benefit of PD-1 blockade treatment of the subject; the expression level of SFRS7 on CD8+ T cells in the PBMCs is positively associated with the expected clinical benefit of PD-1 blockade treatment of the subject; the expression level of CDC14A on CD8+ T cells in the PBMCs is positively associated with the expected clinical benefit of PD-1 blockade treatment of the subject; the expression level of MAP2K5 on CD8+ T cells in the PBMCs is positively associated with the expected clinical benefit of PD-1 blockade treatment of the subject; the expression level of IL11RA on CD8+ T cells in the PBMCs is positively associated with the expected clinical benefit of PD-1 blockade treatment of the subject; the expression level of MLL on CD8+ T cells in the PBMCs is positively associated with the expected clinical benefit of PD-1 blockade treatment of the subject; the expression level of HSPBAP1 on CD8+ T cells in the PBMCs is positively associated with the expected clinical benefit of PD-1 blockade treatment of the subject; the expression level of MAP4K4 on CD8+ T cells in the PBMCs is positively associated with the expected clinical benefit of PD-1 blockade treatment of the subject; the expression level of HELLS on CD8+ T cells in the PBMCs is positively associated with the expected clinical benefit of PD-1 blockade treatment of the subject; the expression level of C1QTNF3 on CD8+ T cells in the PBMCs is positively associated with the expected clinical benefit of PD-1 blockade treatment of the subject; the expression level of UBE2D1 on CD8+ T cells in the PBMCs is positively associated with the expected clinical benefit of PD-1 blockade treatment of the subject; the expression level of FAIM3 on CD8+ T cells in the PBMCs is positively associated with the expected clinical benefit of PD-1 blockade treatment of the subject; the expression level of IF144 on CD8+ T cells in the PBMCs is positively associated with the expected clinical benefit of PD-1 blockade treatment of the subject; the expression level of H2BFM on CD8+ T cells in the PBMCs is positively associated with the expected clinical benefit of PD-1 blockade treatment of the subject; the expression level of GATAD1 on CD8+ T cells in the PBMCs is positively associated with the expected clinical benefit of PD-1 blockade treatment of the subject; the expression level of CASP8 on CD8+ T cells in the PBMCs is positively associated with the expected clinical benefit of PD-1 blockade treatment of the subject; the expression level of SOCS1 on CD8+ T cells in the PBMCs is negatively associated with the expected clinical benefit of PD-1 blockade treatment of the subject; the expression level of PDCD6 on CD8+ T cells in the PBMCs is negatively associated with the expected clinical benefit of PD-1 blockade treatment of the subject; the expression level of NY-ESO-1 on CD8+ T cells in the PBMCs is positively associated with the expected clinical benefit of PD-1 blockade treatment of the subject; the expression level of MART-1 on CD8+ T cells in the PBMCs is positively associated with the expected clinical benefit of PD-1 blockade treatment of the subject; an increase in the expression level of LASS6 on CD8+ T cells in the PBMCs following PD-1 blockade treatment is positively associated with the expected clinical benefit of PD-1 blockade treatment of the subject; a decrease in the expression level of GADD45B on CD8+ T cells in the PBMCs following PD-1 blockade treatment is positively associated with the expected clinical benefit of PD-1 blockade treatment of the subject; a decrease in the expression level of EGR2 on CD8+ T cells in the PBMCs following PD-1 blockade treatment is positively associated with the expected clinical benefit of PD-1 blockade treatment of the subject; a decrease in the expression level of EGR1 on CD8+ T cells in the PBMCs following PD-1 blockade treatment is positively associated with the expected clinical benefit of PD-1 blockade treatment of the subject; a decrease in the expression level of GADD45G on CD8+ T cells in the PBMCs following PD-1 blockade treatment is positively associated with the expected clinical benefit of PD-1 blockade treatment of the subject; a decrease in the expression level of CKS2 on CD8+ T cells in the PBMCs following PD-1 blockade treatment is positively associated with the expected clinical benefit of PD-1 blockade treatment of the subject; a decrease in the expression level of CDKN1C on CD8+ T cells in the PBMCs following PD-1 blockade treatment is positively associated with the expected clinical benefit of PD-1 blockade treatment of the subject; a decrease in the expression level of IER5 on CD8+ T cells in the PBMCs following PD-1 blockade treatment is positively associated with the expected clinical benefit of PD-1 blockade treatment of the subject; a decrease in the expression level of ING1 on CD8+ T cells in the PBMCs following PD-1 blockade treatment is positively associated with the expected clinical benefit of PD-1 blockade treatment of the subject; a decrease in the expression level of IFIH1 on CD8+ T cells in the PBMCs following PD-1 blockade treatment is positively associated with the expected clinical benefit of PD-1 blockade treatment of the subject; a decrease in the expression level of IFNG on CD8+ T cells in the PBMCs following PD-1 blockade treatment is positively associated with the expected clinical benefit of PD-1 blockade treatment of the subject; a decrease in the expression level of IER5L on CD8+ T cells in the PBMCs following PD-1 blockade treatment is positively associated with the expected clinical benefit of PD-1 blockade treatment of the subject; an increase in the expression level of NY-ESO-1 on CD8+ T cells in the PBMCs following PD-1 blockade treatment is positively associated with the expected clinical benefit of PD-1 blockade treatment of the subject; an increase in the expression level of MART-1 on CD8+ T cells in the PBMCs following PD-1 blockade treatment is positively associated with the expected clinical benefit of PD-1 blockade treatment of the subject; a decrease in the number or frequency of T regulatory cells (Tregs; characterized as FoxP3+CD127$^{Low}$CD25+CD4+) in CD4+ T cells in PBMCs following PD-1 blockade treatment is positively associated with the expected clinical benefit of PD-1 blockade treatment of the subject; an increase in the number or frequency of T regulatory cells (Tregs; characterized as FoxP3+CD127$^{Low}$CD25+CD4+) in CD4+ T cells in PBMCs following PD-1 blockade treatment is negatively associated with the expected clinical benefit of PD-1 blockade treatment of the subject; a decrease in the number or frequency of CTLA-4+CD4+ cells in CD4+ T cells in PBMCs following PD-1 blockade treatment is positively associated with the expected clinical benefit of PD-1 blockade treatment of the subject; an increase in the number or frequency of CTLA-4+CD4+ cells in CD4+ T cells in PBMCs following PD-1 blockade treatment is negatively associated with the expected clinical benefit of PD-1 blockade treatment of the subject; a decrease in the number or frequency of CTLA-4+CD8+ cells in CD8+ T cells in PBMCs following PD-1 blockade treatment is positively associated with the expected clinical benefit of PD-1 blockade treatment of the subject; an increase in the number or frequency of CTLA-4+CD8+ cells in CD8+ T cells in PBMCs following PD-1 blockade treatment is negatively associated with the expected clinical benefit of PD-1 blockade treatment of the subject.

As another example, disclosed are methods of treating a subject diagnosed with melanoma with a PD-1 blockade treatment if the expression level of PTEN on CD8+ T cells in the PBMCs prior to PD-1 blockade treatment is more than 1.2 times, preferably more than 1.3 times, most preferably more than 1.4 times the reference level of PTEN; the expression level of GATAD1 on CD8+ T cells in the PBMCs prior to PD-1 blockade is more than 1.1 times, preferably more than 1.3 times, most preferably more than 1.4 times the reference level of GATAD1; the expression level of NKTR on CD8+ T cells in the PBMCs prior to PD-1 blockade is more than 1.1 times, preferably more than 1.3 times, most preferably more than 1.4 times the reference level of NKTR; the expression level of CD276 on CD8+ T cells in the PBMCs prior to PD-1 blockade is less than 0.9 times, preferably less than 0.8 times, most preferably less than 0.7 times the reference level of CD276; the expression level of NSUN6 on CD8+ T cells in the PBMCs prior to PD-1 blockade is more than 1.4 times, preferably more than 1.7 times, most preferably more than 1.9 times the reference level of NSUN6; the expression level of CCAR1 on CD8+ T cells in the PBMCs prior to PD-1 blockade is more than 1.2 times, preferably more than 1.5 times, most preferably more than 1.7 times the reference level of CCAR1; the expression level of SMYD2 on CD8+ T cells in the PBMCs prior to PD-1 blockade is more than 1.2 times, preferably more than 1.4 times, most preferably more than 1.6 times the reference level of SMYD2; the expression level of FBXO9 on CD8+ T cells in the PBMCs prior to PD-1 blockade is more than 1.2 times, preferably more than 1.3 times, preferably more than 1.4 times the reference level of FBXO9; the expression level of NCRNA00153 on CD8+ T cells in the PBMCs prior to PD-1 blockade is more than 1.2 times, preferably more than 1.3 times, most preferably more than 1.4 times the reference level of NCRNA00153; the expression level of NSMAF on CD8+ T cells in the PBMCs prior to PD-1 blockade is more than 1.2 times, preferably more than 1.3 times, most preferably more than 1.4 times the reference level of NSMAF; the expression level of P2RY4 on CD8+ T cells in the PBMCs prior to PD-1 blockade is less than 0.9 times, preferably less than 0.8 times, most preferably less than 0.7 times the reference level of P2RY4; the expression level of RCOR2 on CD8+ T cells in the PBMCs prior to PD-1 blockade is less than 0.9 times, preferably less than 0.8 times, most preferably less than 0.7 times the reference level of RCOR2; the expression level of NUB1 on CD8+ T cells in the PBMCs prior to PD-1 blockade is less than 0.9 times, preferably less than 0.8 times, most preferably less than 0.7 times the reference level of NUB1; the expression level of FCRL2 on CD8+ T cells in the PBMCs prior to PD-1 blockade is less than 0.9 times, preferably less than 0.7 times, most preferably less than 0.5 times the reference level of FCRL2; the expression level of NUCKS1 on CD8+ T cells in the PBMCs prior to PD-1 blockade is less than 0.8 times, preferably less than 0.7 times, most preferably less than 0.6 times the reference level of NUCKS1; the expression level of SHC2 on CD8+ T cells in the PBMCs prior to PD-1 blockade is less than 0.8 times, preferably less than 0.7 times, most preferably less than 0.6 times the reference level of SHC2; the expression level of SCD5 on CD8+ T cells in the PBMCs prior to PD-1 blockade is less than 0.8 times, preferably less than 0.6 times, most preferably less than 0.4 times the reference level of SCD5; the frequency of NY-ESO-1+CD8+ cells in CD8+ T cells in the PBMCs prior to PD-1 blockade treatment is less than 0.5%, preferably less than 0.4%, most preferably less than 0.3%; the frequency of MART-1+CD8+ cells in CD8+ T cells in the PBMCs prior to PD-1 blockade treatment is less than 0.5%, preferably less than 0.4%, most preferably less than 0.3%; or a combination. The subject can also expect a clinical benefit from PD-1 blockade treatment at these levels of expression.

As another example, disclosed are methods of treating a subject diagnosed with melanoma with a PD-1 blockade treatment if the expression level of LASS6 on CD8+ T cells in the PBMCs following the PD-1 blockade treatment is more than 1.2 times, preferably more than 1.3 times, most preferably more than 1.4 times the expression level prior to the PD-1 blockade treatment; the expression level of GADD45B on CD8+ T cells in the PBMCs following the PD-1 blockade treatment is less than 0.8 times, preferably less than 0.7 times, most preferably less than 0.6 times the expression level prior to the PD-1 blockade treatment; the expression level of EGR2 on CD8+ T cells in the PBMCs following the PD-1 blockade treatment is less than 0.8 times, preferably less than 0.7 times, most preferably less than 0.6 times the expression level prior to the PD-1 blockade treatment; the expression level of EGR1 on CD8+ T cells in the PBMCs following the PD-1 blockade treatment is less than 0.7 times, preferably less than 0.4 times, most preferably less than 0.2 times the expression level prior to the PD-1 blockade treatment; the expression level of GADD45G on CD8+ T cells in the PBMCs following the PD-1 blockade treatment is less than 0.9 times, preferably less than 0.8 times, most preferably less than 0.7 times the expression level prior to the PD-1 blockade treatment; the expression level of CKS2 on CD8+ T cells in the PBMCs following the PD-1 blockade treatment is less than 0.9 times, preferably less than 0.8 times, most preferably less than 0.7 times the expression level prior to the PD-1 blockade treatment; the expression level of CDKN1C on CD8+ T cells in the PBMCs following the PD-1 blockade treatment is less than 0.9 times, preferably less than 0.8 times, most preferably less than 0.7 times the expression level prior to the PD-1 blockade treatment; the expression level of IER5 on CD8+ T cells in the PBMCs following the PD-1 blockade treatment is less than 0.9 times, preferably less than 0.8 times, most preferably less than 0.7 times the expression level prior to the PD-1 blockade treatment; the frequency of NY-ESO-1+CD8+ cells in CD8+ T cells in the PBMCs following the PD-1 blockade treatment is less than 0.7 times, preferably less than 0.6 times, most preferably less than 0.5 times the frequency prior to the PD-1 blockade treatment; the frequency of MART-1+CD8+ cells in CD8+ T cells in the PBMCs following the PD-1 blockade treatment is less than 0.7 times, preferably less than 0.6 times, most preferably less than 0.5 times the frequency prior to the PD-1 blockade treatment; the number or frequency of T regulatory cells (Tregs; characterized as FoxP3+CD127$^{Low}$CD25+CD4+) in CD4+ T cells in PBMCs following the PD-1 blockade treatment is less than 1.0 times, preferably less than 0.9 times, most preferably less than 0.8 times the number or frequency of Tregs in CD4+ T cells in PBMCs prior to the PD-1 blockade treatment; the number or frequency of CTLA-4+CD4+ cells in CD4+ T cells in PBMCs following the PD-1 blockade treatment is less than 1.0 times, preferably less than 0.9 times, most preferably less than 0.8 times the number or frequency of CTLA-4+CD4+ cells in CD4+ T cells in PBMCs prior to the PD-1 blockade treatment; the number or frequency of CTLA-4+CD8+ cells in CD8+ T cells in PBMCs following the PD-1 blockade treatment is less than 1.0 times, preferably less than 0.9 times, most preferably less than 0.8 times the number or frequency of CTLA-4+CD8+ cells in CD8+ T cells in PBMCs prior to the PD-1 blockade treatment; or a combination.

As another example, disclosed are methods of treating a subject diagnosed with melanoma with a treatment other than a PD-1 blockade treatment, or with both a PD-1 blockade treatment and a different treatment, if the expression level of PTEN on CD8+ T cells in the PBMCs prior to PD-1 blockade treatment is less than 1.1 times, preferably less than 1.0 times, most preferably less than 0.9 times the reference level of PTEN; the expression level of GATAD1 on CD8+ T cells in the PBMCs prior to PD-1 blockade is less than 1.0 times, preferably less than 0.9 times, most preferably less than 0.8 times the reference level of GATAD1; the expression level of NKTR on CD8+ T cells in the PBMCs prior to PD-1 blockade is less than 1.0 times, preferably less than 0.9 times, most preferably less than 0.8 times the reference level of NKTR; the expression level of CD276 on CD8+ T cells in the PBMCs prior to PD-1 blockade is more than 1.0 times, preferably more than 1.1 times, most preferably more than 1.2 times the reference level of CD276; the expression level of NSUN6 on CD8+ T cells in the PBMCs prior to PD-1 blockade is less than 1.2 times, preferably less than 1.0 times, most preferably less than 0.8 times the reference level of NSUN6; the expression level of CCAR1 on CD8+ T cells in the PBMCs prior to PD-1 blockade is less than 1.1 times, preferably less than 1.0 times, most preferably less than 0.9 times the reference level of CCAR1; the expression level of SMYD2 on CD8+ T cells in the PBMCs prior to PD-1 blockade is less than 1.1 times, preferably less than 1.0 times, most preferably less than 0.9 times the reference level of SMYD2; the expression level of FBXO9 on CD8+ T cells in the PBMCs prior to PD-1 blockade is less than 1.1 times, preferably less than 1.0 times, most preferably less than 0.9 times the reference level of FBXO9; the expression level of NCRNA00153 on CD8+ T cells in the PBMCs prior to PD-1 blockade is less than 1.1 times, preferably less than 1.0 times, most preferably less than 0.9 times the reference level of NCRNA00153; the expression level of NSMAF on CD8+ T cells in the PBMCs prior to PD-1 blockade is less than 1.1 times, preferably less than 1.0 times, most preferably less than 0.9 times the reference level of NSMAF; the expression level of P2RY4 on CD8+ T cells in the PBMCs prior to PD-1 blockade is more than 1.0 times, preferably more than 1.1 times, most preferably more than 1.2 times the reference level of P2RY4; the expression level of RCOR2 on CD8+ T cells in the PBMCs prior to PD-1 blockade is more than 1.0 times, preferably more than 1.1 times, most preferably more than 1.2 times the reference level of RCOR2; the expression level of NUB1 on CD8+ T cells in the PBMCs prior to PD-1 blockade is more than 1.0 times, preferably more than 1.1 times, most preferably more than 1.2 times the reference level of NUB1; the expression level of FCRL2 on CD8+ T cells in the PBMCs prior to PD-1 blockade is more than 1.0 times, preferably more than 1.1 times, most preferably more than 1.2 times the reference level of FCRL2; the expression level of NUCKS1 on CD8+ T cells in the PBMCs prior to PD-1 blockade is more than 0.9 times, preferably more than 1.0 times, most preferably more than 1.1 times the reference level of NUCKS1; the expression level of SHC2 on CD8+ T cells in the PBMCs prior to PD-1 blockade is more than 0.9 times, preferably more than 1.0 times, most preferably more than 1.1 times the reference level of SHC2; the expression level of SCD5 on CD8+ T cells in the PBMCs prior to PD-1 blockade is more than 0.9 times, preferably more than 1.0 times, most preferably more than 1.1 times the reference level of SCD5; the frequency of NY-ESO-1+CD8+ cells in CD8+ T cells in the PBMCs prior to PD-1 blockade treatment is more than 0.5%, preferably more than 0.7%, most preferably more than 0.8%; the frequency of MART-1+CD8+ cells in CD8+ T cells in the PBMCs prior to PD-1 blockade treatment is more than 0.5%, preferably more than 0.7%, most preferably more than 0.8%; the number or frequency of Tregs in CD4+ T cells in PBMCs following PD-1 blockade treatment is more than 1.0 times, preferably more than 1.1 times, most preferably more than 1.2 times the number or frequency of Tregs in CD4+ T cells in PBMCs prior to the PD-1 blockade treatment; the number or frequency of CTLA-4+CD4+ cells in CD4+ T cells in PBMCs following the PD-1 blockade treatment is more than 1.0 times, preferably more than 1.1 times, most preferably more than 1.2 times the number or frequency of CTLA-4+ CD4+ cells in CD4+ T cells in PBMCs prior to the PD-1 blockade treatment; the number or frequency of CTLA-4+ CD8+ cells in CD8+ T cells in PBMCs following the PD-1 blockade treatment is more than 1.0 times, preferably more than 1.1 times, most preferably more than 1.2 times the number or frequency of CTLA-4+CD8+ cells in CD8+ T cells in PBMCs prior to the PD-1 blockade treatment; or a combination. The subject can also expect a clinical benefit from PD-1 blockade treatment at these levels of expression.

As another example, disclosed are methods of treating a subject diagnosed with melanoma with a treatment other than a PD-1 blockade treatment, or with both a PD-1 blockade treatment and a different treatment, if the expression level of LASS6 on CD8+ T cells in the PBMCs following the PD-1 blockade treatment is less than 1.1 times, preferably less than 1.0 times, most preferably less than 0.9 times the expression level prior to the PD-1 blockade treatment; the expression level of GADD45B on CD8+ T cells in the PBMCs following the PD-1 blockade treatment is more than 0.9 times, preferably more than 1.0 times, most preferably more than 1.1 times the expression level prior to the PD-1 blockade treatment; the expression level of EGR2 on CD8+ T cells in the PBMCs following the PD-1 blockade treatment is more than 0.9 times, preferably more than 1.0 times, most preferably more than 1.1 times the expression level prior to the PD-1 blockade treatment; the expression level of EGR1 on CD8+ T cells in the PBMCs following the PD-1 blockade treatment is more than 0.8 times, preferably more than 0.9 times, most preferably more than 1.0 times the expression level prior to the PD-1 blockade treatment; the expression level of GADD45G on CD8+ T cells in the PBMCs following the PD-1 blockade treatment is more than 1.0 times, preferably more than 1.1 times, most preferably more than 1.2 times the expression level prior to the PD-1 blockade treatment; the expression level of CKS2 on CD8+ T cells in the PBMCs following the PD-1 blockade treatment is more than 1.0 times, preferably more than 1.1 times, most preferably more than 1.2 times the expression level prior to the PD-1 blockade treatment; the expression level of CDKN1C on CD8+ T cells in the PBMCs following the PD-1 blockade treatment is more than 1.0 times, preferably more than 1.1 times, most preferably more than 1.2 times the expression level prior to the PD-1 blockade treatment; the expression level of IER5 on CD8+ T cells in the PBMCs following the PD-1 blockade treatment is more than 1.0 times, preferably more than 1.1 times, most preferably more than 1.2 times the expression level prior to the PD-1 blockade treatment; the number or frequency of Tregs in CD4+ T cells in PBMCs following PD-1 blockade treatment is more than 1.0 times, preferably more than 1.1 times, most preferably more than 1.2 times the number or frequency of Tregs in CD4+ T cells in PBMCs prior to the PD-1 blockade treatment; the number or frequency of CTLA-4+CD4+ cells in CD4+ T cells in PBMCs following the PD-1 blockade treatment is more than 1.0 times, preferably more than 1.1 times, most preferably more than 1.2 times the number or frequency of CTLA-4+CD4+ cells in CD4+ T cells in PBMCs prior to the PD-1 blockade treatment; the number or frequency of CTLA-4+CD8+ cells in CD8+ T cells in PBMCs following the PD-1 blockade treatment is more than 1.0 times, preferably more than 1.1 times, most preferably more than 1.2 times the number or frequency of CTLA-4+CD8+ cells in CD8+ T cells in PBMCs prior to the PD-1 blockade treatment; or a combination. The subject would not expect a clinical benefit from PD-1 blockade treatment at these levels of expression.

In some forms of the method, the expression level of PTEN on CD8+ T cells in the PBMCs prior to PD-1 blockade treatment is positively associated with the expected clinical benefit of PD-1 blockade treatment of the subject; the expression level of GATAD1 on CD8+ T cells in the PBMCs prior to PD-1 blockade treatment is positively associated with the expected clinical benefit of PD-1 blockade treatment of the subject; the expression level of NKTR on CD8+ T cells in the PBMCs prior to PD-1 blockade treatment is positively associated with the expected clinical benefit of PD-1 blockade treatment of the subject; the expression level of CD276 on CD8+ T cells in the PBMCs prior to PD-1 blockade treatment is negatively associated with the expected clinical benefit of PD-1 blockade treatment of the subject; the expression level of NSUN6 on CD8+ T cells in the PBMCs prior to PD-1 blockade treatment is positively associated with the expected clinical benefit of PD-1 blockade treatment of the subject; the expression level of CCAR1 on CD8+ T cells in the PBMCs prior to PD-1 blockade treatment is positively associated with the expected clinical benefit of PD-1 blockade treatment of the subject; the expression level of SMYD2 on CD8+ T cells in the PBMCs prior to PD-1 blockade treatment is positively associated with the expected clinical benefit of PD-1 blockade treatment of the subject; the expression level of FBXO9 on CD8+ T cells in the PBMCs prior to PD-1 blockade treatment is positively associated with the expected clinical benefit of PD-1 blockade treatment of the subject; the expression level of NCRNA00153 on CD8+ T cells in the PBMCs prior to PD-1 blockade treatment is positively associated with the expected clinical benefit of PD-1 blockade treatment of the subject; the expression level of NSMAF on CD8+ T cells in the PBMCs prior to PD-1 blockade treatment is positively associated with the expected clinical benefit of PD-1 blockade treatment of the subject; the expression level of P2RY4 on CD8+ T cells in the PBMCs prior to PD-1 blockade treatment is negatively associated with the expected clinical benefit of PD-1 blockade treatment of the subject; the expression level of RCOR2 on CD8+ T cells in the PBMCs prior to PD-1 blockade treatment is negatively associated with the expected clinical benefit of PD-1 blockade treatment of the subject; the expression level of NUB1 on CD8+ T cells in the PBMCs prior to PD-1 blockade treatment is negatively associated with the expected clinical benefit of PD-1 blockade treatment of the subject; the expression level of FCRL2 on CD8+ T cells in the PBMCs prior to PD-1 blockade treatment is negatively associated with the expected clinical benefit of PD-1 blockade treatment of the subject; the expression level of NUCKS1 on CD8+ T cells in the PBMCs prior to PD-1 blockade treatment is negatively associated with the expected clinical benefit of PD-1 blockade treatment of the subject; the expression level of SHC2 on CD8+ T cells in the PBMCs prior to PD-1 blockade treatment is negatively associated with the expected clinical benefit of PD-1 blockade treatment of the subject; the expression level of SCD5 on CD8+ T cells in the PBMCs prior to PD-1 blockade treatment is negatively associated with the expected clinical benefit of PD-1 blockade treatment of the subject; the expression level of USP9Y on CD8+ T cells in the PBMCs prior to PD-1 blockade treatment is positively associated with the expected clinical benefit of PD-1 blockade treatment of the subject; the expression level of HSPD1 on CD8+ T cells in the PBMCs prior to PD-1 blockade treatment is positively associated with the expected clinical benefit of PD-1 blockade treatment of the subject; the expression level of CISH on CD8+ T cells in the PBMCs prior to PD-1 blockade treatment is positively associated with the expected clinical benefit of PD-1 blockade treatment of the subject; the expression level of KLF12 on CD8+ T cells in the PBMCs prior to PD-1 blockade treatment is positively associated with the expected clinical benefit of PD-1 blockade treatment of the subject; the expression level of NCF4 on CD8+ T cells in the PBMCs prior to PD-1 blockade treatment is positively associated with the expected clinical benefit of PD-1 blockade treatment of the subject; the expression level of SFRS7 on CD8+ T cells in the PBMCs prior to PD-1 blockade treatment is positively associated with the expected clinical benefit of PD-1 blockade treatment of the subject; the expression level of CDC14A on CD8+ T cells in the PBMCs prior to PD-1 blockade treatment is positively associated with the expected clinical benefit of PD-1 blockade treatment of the subject; the expression level of MAP2K5 on CD8+ T cells in the PBMCs prior to PD-1 blockade treatment is positively associated with the expected clinical benefit of PD-1 blockade treatment of the subject; the expression level of IL11RA on CD8+

T cells in the PBMCs prior to PD-1 blockade treatment is positively associated with the expected clinical benefit of PD-1 blockade treatment of the subject; the expression level of MLL on CD8+ T cells in the PBMCs prior to PD-1 blockade treatment is positively associated with the expected clinical benefit of PD-1 blockade treatment of the subject; the expression level of HSPBAP1 on CD8+ T cells in the PBMCs prior to PD-1 blockade treatment is positively associated with the expected clinical benefit of PD-1 blockade treatment of the subject; the expression level of MAP4K4 on CD8+ T cells in the PBMCs prior to PD-1 blockade treatment is positively associated with the expected clinical benefit of PD-1 blockade treatment of the subject; the expression level of HELLS on CD8+ T cells in the PBMCs prior to PD-1 blockade treatment is positively associated with the expected clinical benefit of PD-1 blockade treatment of the subject; the expression level of C1QTNF3 on CD8+ T cells in the PBMCs prior to PD-1 blockade treatment is positively associated with the expected clinical benefit of PD-1 blockade treatment of the subject; the expression level of UBE2D1 on CD8+ T cells in the PBMCs prior to PD-1 blockade treatment is positively associated with the expected clinical benefit of PD-1 blockade treatment of the subject; the expression level of FAIM3 on CD8+ T cells in the PBMCs prior to PD-1 blockade treatment is positively associated with the expected clinical benefit of PD-1 blockade treatment of the subject; the expression level of IF144 on CD8+ T cells in the PBMCs prior to PD-1 blockade treatment is positively associated with the expected clinical benefit of PD-1 blockade treatment of the subject; the expression level of H2BFM on CD8+ T cells in the PBMCs prior to PD-1 blockade treatment is positively associated with the expected clinical benefit of PD-1 blockade treatment of the subject; the expression level of GATAD1 on CD8+ T cells in the PBMCs prior to PD-1 blockade treatment is positively associated with the expected clinical benefit of PD-1 blockade treatment of the subject; the expression level of CASP8 on CD8+ T cells in the PBMCs prior to PD-1 blockade treatment is positively associated with the expected clinical benefit of PD-1 blockade treatment of the subject; the expression level of SOCS1 on CD8+ T cells in the PBMCs prior to PD-1 blockade treatment is negatively associated with the expected clinical benefit of PD-1 blockade treatment of the subject; the expression level of PDCD6 on CD8+ T cells in the PBMCs prior to PD-1 blockade treatment is negatively associated with the expected clinical benefit of PD-1 blockade treatment of the subject; the expression level of NY-ESO-1 on CD8+ T cells in the PBMCs prior to PD-1 blockade treatment is negatively associated with the expected clinical benefit of PD-1 blockade treatment of the subject; and the expression level of MART-1 on CD8+ T cells in the PBMCs prior to PD-1 blockade treatment is negatively associated with the expected clinical benefit of PD-1 blockade treatment of the subject.

In some forms of the method, the expression prior the PD-1 blockade treatment is compared to a reference level of expression and an expression level of PTEN on CD8+ T cells in the PBMCs prior to PD-1 blockade treatment greater than the reference level of PTEN indicates that the subject can expect a clinical benefit from PD-1 blockade treatment; an expression level of GATAD1 on CD8+ T cells in the PBMCs prior to PD-1 blockade greater than the reference level of GATAD1 indicates that the subject can expect a clinical benefit from PD-1 blockade treatment; an expression level of NKTR on CD8+ T cells in the PBMCs prior to PD-1 blockade greater than the reference level of NKTR indicates that the subject can expect a clinical benefit from PD-1 blockade treatment; an expression level of CD276 on CD8+ T cells in the PBMCs prior to PD-1 blockade lower than the reference level of CD276 indicates that the subject can expect a clinical benefit from PD-1 blockade treatment; an expression level of NSUN6 on CD8+ T cells in the PBMCs prior to PD-1 blockade greater than the reference level of NSUN6 indicates that the subject can expect a clinical benefit from PD-1 blockade treatment; an expression level of CCAR1 on CD8+ T cells in the PBMCs prior to PD-1 blockade greater than the reference level of CCAR1 indicates that the subject can expect a clinical benefit from PD-1 blockade treatment; an expression level of SMYD2 on CD8+ T cells in the PBMCs prior to PD-1 blockade greater than the reference level of SMYD2 indicates that the subject can expect a clinical benefit from PD-1 blockade treatment; an expression level of FBXO9 on CD8+ T cells in the PBMCs prior to PD-1 blockade greater than the reference level of FBXO9 indicates that the subject can expect a clinical benefit from PD-1 blockade treatment; an expression level of NCRNA00153 on CD8+ T cells in the PBMCs prior to PD-1 blockade greater than the reference level of NCRNA00153 indicates that the subject can expect a clinical benefit from PD-1 blockade treatment; an expression level of NSMAF on CD8+ T cells in the PBMCs prior to PD-1 blockade greater than the reference level of NSMAF indicates that the subject can expect a clinical benefit from PD-1 blockade treatment; an expression level of P2RY4 on CD8+ T cells in the PBMCs prior to PD-1 blockade lower than the reference level of P2RY4 indicates that the subject can expect a clinical benefit from PD-1 blockade treatment; an expression level of RCOR2 on CD8+ T cells in the PBMCs prior to PD-1 blockade lower than the reference level of RCOR2 indicates that the subject can expect a clinical benefit from PD-1 blockade treatment; an expression level of NUB1 on CD8+ T cells in the PBMCs prior to PD-1 blockade lower than the reference level of NUB1 indicates that the subject can expect a clinical benefit from PD-1 blockade treatment; an expression level of FCRL2 on CD8+ T cells in the PBMCs prior to PD-1 blockade lower than the reference level of FCRL2 indicates that the subject can expect a clinical benefit from PD-1 blockade treatment; an expression level of NUCKS1 on CD8+ T cells in the PBMCs prior to PD-1 blockade lower than the reference level of NUCKS1 indicates that the subject can expect a clinical benefit from PD-1 blockade treatment; an expression level of SHC2 on CD8+ T cells in the PBMCs prior to PD-1 blockade lower than the reference level of SHC2 indicates that the subject can expect a clinical benefit from PD-1 blockade treatment; an expression level of SCD5 on CD8+ T cells in the PBMCs prior to PD-1 blockade lower than the reference level of SCD5 indicates that the subject can expect a clinical benefit from PD-1 blockade treatment; an expression level of USP9Y on CD8+ T cells in the PBMCs prior to PD-1 blockade greater than the reference level of USP9Y indicates that the subject can expect a clinical benefit from PD-1 blockade treatment; an expression level of HSPD1 on CD8+ T cells in the PBMCs prior to PD-1 blockade greater than the reference level of HSPD1 indicates that the subject can expect a clinical benefit from PD-1 blockade treatment; an expression level of CISH on CD8+ T cells in the PBMCs prior to PD-1 blockade greater than the reference level of CISH indicates that the subject can expect a clinical benefit from PD-1 blockade treatment; an expression level of KLF12 on CD8+ T cells in the PBMCs prior to PD-1 blockade greater than the reference level of KLF12 indicates that the subject can expect a clinical benefit from PD-1 blockade treatment; an expression level of NCF4 on CD8$^+$ T cells in the PBMCs prior to PD-1 blockade greater than the reference level of NCF4 indicates that the subject can expect a clinical benefit from PD-1 blockade treatment; an expression level of SFRS7 on CD8$^+$ T cells in the PBMCs prior to PD-1 blockade greater than the reference level of SFRS7 indicates that the subject can expect a clinical benefit from PD-1 blockade treatment; an expression level of CDC14A on CD8$^+$ T cells in the PBMCs prior to PD-1 blockade greater than the reference level of CDC14A indicates that the subject can expect a clinical benefit from PD-1 blockade treatment; an expression level of MAP2K5 on CD8$^+$ T cells in the PBMCs prior to PD-1 blockade greater than the reference level of MAP2K5 indicates that the subject can expect a clinical benefit from PD-1 blockade treatment; an expression level of IL11RA on CD8$^+$ T cells in the PBMCs prior to PD-1 blockade greater than the reference level of IL11RA indicates that the subject can expect a clinical benefit from PD-1 blockade treatment; an expression level of MLL on CD8$^+$ T cells in the PBMCs prior to PD-1 blockade greater than the reference level of MLL indicates that the subject can expect a clinical benefit from PD-1 blockade treatment; an expression level of HSPBAP1 on CD8$^+$ T cells in the PBMCs prior to PD-1 blockade greater than the reference level of HSPBAP1 indicates that the subject can expect a clinical benefit from PD-1 blockade treatment; an expression level of MAP4K4 on CD8$^+$ T cells in the PBMCs prior to PD-1 blockade greater than the reference level of MAP4K4 indicates that the subject can expect a clinical benefit from PD-1 blockade treatment; an expression level of HELLS on CD8$^+$ T cells in the PBMCs prior to PD-1 blockade greater than the reference level of HELLS indicates that the subject can expect a clinical benefit from PD-1 blockade treatment; an expression level of C1QTNF3 on CD8$^+$ T cells in the PBMCs prior to PD-1 blockade greater than the reference level of C1QTNF3 indicates that the subject can expect a clinical benefit from PD-1 blockade treatment; an expression level of UBE2D1 on CD8$^+$ T cells in the PBMCs prior to PD-1 blockade greater than the reference level of UBE2D1 indicates that the subject can expect a clinical benefit from PD-1 blockade treatment; an expression level of FAIM3 on CD8$^+$ T cells in the PBMCs prior to PD-1 blockade greater than the reference level of FAIM3 indicates that the subject can expect a clinical benefit from PD-1 blockade treatment; an expression level of IF144 on CD8$^+$ T cells in the PBMCs prior to PD-1 blockade greater than the reference level of IF144 indicates that the subject can expect a clinical benefit from PD-1 blockade treatment; an expression level of H2BFM on CD8$^+$ T cells in the PBMCs prior to PD-1 blockade greater than the reference level of H2BFM indicates that the subject can expect a clinical benefit from PD-1 blockade treatment; an expression level of GATAD1 on CD8$^+$ T cells in the PBMCs prior to PD-1 blockade greater than the reference level of GATAD1 indicates that the subject can expect a clinical benefit from PD-1 blockade treatment; an expression level of CASP8 on CD8$^+$ T cells in the PBMCs prior to PD-1 blockade greater than the reference level of CASP8 indicates that the subject can expect a clinical benefit from PD-1 blockade treatment; an expression level of SOCS1 on CD8$^+$ T cells in the PBMCs prior to PD-1 blockade lower than the reference level of SOCS1 indicates that the subject can expect a clinical benefit from PD-1 blockade treatment; and an expression level of PDCD6 on CD8$^+$ T cells in the PBMCs prior to PD-1 blockade lower than the reference level of PDCD6 indicates that the subject can expect a clinical benefit from PD-1 blockade treatment.

BRIEF DESCRIPTION OF THE DRAWINGS

FIG. 7A is a graph of the percent of Tregs in CD4$^+$ T cells measured in responders and nonresponders pre and post treatment with BMS-936558. FIG. 7B is a graph of the percent change in Tregs for responders (Yes) and nonresponders (No). Tregs (phenotype as FoxP3+CD127LowCD25+CD4+) decreased in responders and increased in non-responders significantly. The change between two groups is significant, too. FIG. 7C is a graph of the percent change in CD4$^+$/CLTA-4$^+$ T cells for responders (Yes) and nonresponders (No). FIG. 7D is a graph of the percent change in CD8$^+$/CLTA-4$^+$ T cells for responders (Yes) and nonresponders (No). CTLA-4+ in CD4 and CD8+ has significant change between responders and non-responders.

FIG. 8A is a graph of the percent of NY-ESO-1 Tetramer$^+$ CD8$^+$ T cells measured in responders and nonresponders before treatment with BMS-936558. FIG. 8B is a graph of the percent of MART-1 Tetramer$^+$ CD8$^+$ T cells measured in responders and nonresponders before treatment with BMS-936558. Both NY-ESO-1 and MART-1 specific CD8+ T cells had higher baseline. Level in non-responders was compared to responders. FIG. 8C is a graph of the percent of NY-ESO-1 Tetramer$^+$ CD8$^+$ T cells measured in responders and nonresponders after treatment with BMS-936558. FIG. 8D is a graph of the percent of MART-1 Tetramer$^+$ CD8$^+$ T cells measured in responders and nonresponders after treatment with BMS-936558. Responders had significant increase in both NY-ESO-1 and MART-1 specific CD8+ T cells at 12 weeks after BMS-936558 treatment.

FIG. 11 is a list of identified baseline biomarkers in CD4+ T cells associated with outcome (Relapse vs. NED).

FIG. 12 is a list of identified baseline biomarkers in CD8+ T cells associated with outcome (Relapse vs. NED).

FIG. 13 is a list of identified baseline biomarkers in CD4+ T cells associated with the induction of irAE (Yes vs. No).

FIG. 14 is a list of identified baseline biomarkers in CD8+ T cells associated with the induction of irAE (Yes vs. No).

DETAILED DESCRIPTION OF THE INVENTION

I. Definitions

Figure 1A:
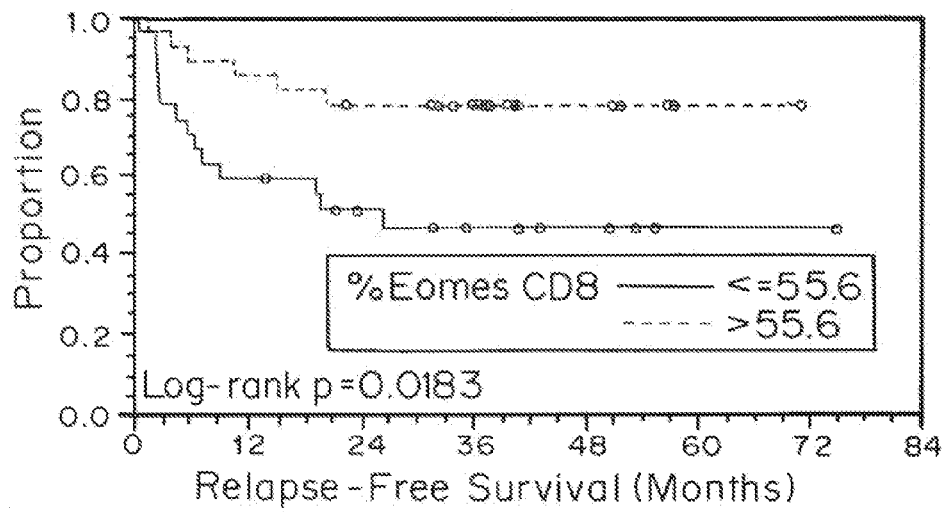
FIGS. 1A, 1B, and 1C are Kaplan-Meier relapse-free survival curves showing the proportion of patients with high baseline EOMES$^+$/CD8$^+$ (FIG. 1A, dashed line), low EOMES$^+$/CD8$^+$ (FIG. 1A, solid line), high baseline Ki67$^+$ EOMES$^+$/CD8$^+$ (FIG. 1B, dashed line), low Ki67$^+$ EOMES$^+$/CD8$^+$ (FIG. 1B, solid line), high level of CCR7 on CD4$^+$ cells (FIG. 1C, dashed line), or low level of CCR7 on CD4$^+$ cells (FIG. 1C, solid line) as a function of relapse-free survival (months).

The term "individual," "host," "subject," and "patient" are used interchangeably to refer to any individual who is the target of administration or treatment. The subject can be a vertebrate, for example, a mammal Thus, the subject can be a human or veterinary patient.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "cancer" or "malignant neoplasm" refers to a cell that displays uncontrolled growth, invasion upon adjacent tissues, and often metastasis to other locations of the body.

The term "metastasis" refers to the spread of malignant tumor cells from one organ or part to another non-adjacent organ or part. Cancer cells can "break away," "leak," or "spill" from a primary tumor, enter lymphatic and blood vessels, circulate through the bloodstream, and settle down to grow within normal tissues elsewhere in the body. When tumor cells metastasize, the new tumor is called a secondary or metastatic cancer or tumor.

The term "biomarker" as used herein refers to a peptide, protein, or nucleic acid in or on a cell of a subject whose presence and/or level is indicative of a biological process, pathogenic process, or pharmacologic response to therapeutic intervention. In preferred embodiments, detection of the biomarker may be used to predict therapeutic outcome.

The term "relapse" as used herein refers to the return of a cancer after a period of improvement, e.g., remission.

The term "immune related adverse event" or "irAE" refers to side effects from CTLA-4 blockade therapy that are inflammatory in nature, including rash, colitis, and hepatitis.

The term "frequency" as used herein and in the context of the disclosed methods refers to the percentage of PBMCs expressing a particular biomarker or combination of biomarkers at threshold levels. These levels may be determined empirically using standards and controls.

The term "expression level" as used herein refers to quantitative or relative amounts of biomarker in or on a cell that is detected by an assay.

The level of expression measured for the disclosed biomarkers can be compared to any suitable control or standard level of expression. For example, a normal level (such as the level of the biomarker in a subject or subjects without cancer), a control level (such as the level of the biomarker in a subject or subjects that do not respond and/or do not get clinical benefit from PD-1 blockade treatment), etc. can be used as a comparison to measured levels of expression of the biomarkers. Such levels used for comparison to measured expression levels of the biomarkers can be referred to as reference levels.

The term "response," in the context of CTLA-4 and PD-1 blockade treatment, refers to a positive clinical response to the treatment. Related to this, the term "responder," in the context of CTLA-4 and PD-1 blockade treatment, refers to a subject that exhibits a response to the treatment. Similarly, the term "non-response," in the context of CTLA-4 and PD-1 blockade treatment, refers to a lack of clinical response or a negative clinical response to the treatment; and the term "non-responder," in the context of CTLA-4 and PD-1 blockade treatment, refers to a subject that exhibits a non-response to the treatment.

II. Biomarkers

A. CD8

In some embodiments, the biomarker is cluster of differentiation 8 (CD8). CD8 is a transmembrane glycoprotein that serves as a co-receptor for the T cell receptor (TCR). Like the TCR, CD8 binds to a major histocompatibility complex (MHC) molecule, but is specific for the class I MHC protein. There are two isoforms of the protein, alpha and beta, each encoded by a different gene. In humans, both genes are located on chromosome 2 in position 2p12. The CD8 co-receptor is predominantly expressed on the surface of cytotoxic T cells, but can also be found on natural killer cells, cortical thymocytes, and dendritic cells. It is expressed in T cell lymphoblastic lymphoma and hypo-pigmented mycosis fungoides, but is frequently lost in other T-cell neoplasms.

Antibodies that specifically bind human CD8 are commercially available and include clone 3B5 (Life Technologies), clone SK1 (Stemcell Technologies), clone SP16 (Spring Biosciences), and OKT8 (eBioscience).

B. CD4

Cluster of differentiation 4 (CD4) is a glycoprotein expressed on the surface of T helper cells, monocytes, macrophages, and dendritic cells. CD4 is a co-receptor that assists the T cell receptor (TCR) with an antigen-presenting cell. Using its portion that resides inside the T cell, CD4 amplifies the signal generated by the TCR by recruiting an enzyme, known as the tyrosine kinase lck, which is essential for activating many molecules involved in the signaling cascade of an activated T cell. CD4 also interacts directly with MHC class II molecules on the surface of the antigen-presenting cell using its extracellular domain.

CD4 continues to be expressed in most neoplasms derived from T helper cells. It is therefore possible to use CD4 immunohistochemistry on tissue biopsy samples to identify most forms of peripheral T cell lymphoma and related malignant conditions. The antigen has also been associated with a number of autoimmune diseases such as vitiligo and type I diabetes mellitus.

Antibodies that specifically bind human CD4 are commercially available and include clone L120 (Stemcell Technologies), clone SK3 (Stemcell Technologies), clone RPA-T4 (Imgenex), clone Q4120 (Sigma-Aldrich), and clone SP35 (Spring Biosciences).

C. EOMES

Eomesodermin homolog (EOMES) is a key transcription factor of cytotoxic lymphocyte lineages. Antibodies that specifically bind human EOMES are commercially available and include clone 1A8 (Abnova), clone 2C7 (Abnova), and clone 3E7 (MPBio). The nucleic acid sequence for human EOMES is set forth in Accession No. NP_005433.

D. Ki67

The Ki-67 protein (also known as MKI67) is nuclear protein that is associated with and may be necessary for cellular proliferation. During interphase, Ki-67 can be exclusively detected within the cell nucleus, whereas in mitosis most of the protein is relocated to the surface of the chromosomes. Ki-67 protein is present during all active phases of the cell cycle (G1, S, G2, and mitosis), but is absent from resting cells (G0).

Ki-67 is an excellent marker to determine the growth fraction of a given cell population. The fraction of Ki-67-positive tumor cells (the Ki-67 labeling index) is often correlated with the clinical course of cancer. The best-studied examples in this context are carcinomas of the prostate, brain and the breast. For these types of tumors, the prognostic value for survival and tumor recurrence have repeatedly been proven in uni- and multivariate analysis.

MIB1 is a commonly used monoclonal antibody that detects the Ki-67 antigen. It is used in clinical applications to determine the Ki-67 labeling index. One of its primary advantages over the original Ki-67 antibody (and the reason why it has essentially supplanted the original antibody for clinical use) is that it can be used on formalin-fixed paraffin-embedded sections, after heat-mediated antigen retrieval (see section Original Ki-67 antibody).

E. TGFβR3

TGFβ receptors are single pass serine/threonine kinase receptors. They exist in several different isoforms that can be homo- or heterodimeric. The number of characterized ligands in the TGFβ superfamily far exceeds the number of known receptors, suggesting the promiscuity that exists between the ligand and receptor interactions. Three TGF-β receptor types can be distinguished by their structural and functional properties. Receptor types I and II have similar ligand-binding affinities and can be distinguished from each other only by peptide mapping. Both receptor types I and II have a high affinity for TGF-β1 and low affinity for TGF-β2. TGF-β receptor type III (TGFβR3) has a high affinity for both TGF-β1 and TGF-β2.

Antibodies that specifically bind human TGFβR3 are commercially available and include clone ZT001 (Invitrogen), clone D11G10 (Cell Signaling Technologies), and clone 20724 (R&D Systems). The nucleic acid sequence for human TGFβR3 is set forth in Accession No. NM_003243.

F. CCR7

C—C chemokine receptor type 7 (CCR7) is expressed in various lymphoid tissues and activates B and T lymphocytes. It has been shown to control the migration of memory T cells home to lymph nodes, as well as stimulate dendritic cell maturation. CCR7 signaling is also known to play a role in lymph node metastasis. The chemokine (C—C motif) ligand 19 (CCL19/ELC) has been reported to be a specific ligand of this receptor.

Antibodies that specifically bind human CCR7 are commercially available and include clone 150503 (R&D Systems), clone FR11-11E8 (Miltenyi Biotec), and clone 3D12 (eBioscience). The nucleic acid sequence for human CCR7 is set forth in Accession No. NM_001838.2.

G. CD71

CD71, also known as transferrin receptor protein 1 (TfR1), is a protein encoded by the TFRC gene. CD71 is required for iron delivery from transferrin to cells.

Antibodies that specifically bind human CD71 are commercially available and include GR08K-100UG, GR09L-100UG, CBL47 (available from EMD Millipore); and clone 29806 (available from R&D Systems). The nucleic acid sequence for human CD71 is set forth in Accession No. NM_001128148.

H. CD109

CD109 is a GPI-linked cell surface antigen expressed by CD34+ acute myeloid leukemia cell lines, T-cell lines, activated T lymphoblasts, endothelial cells, and activated platelets (Lin et al., *Blood* 99(5):1683-91 (2002)). CD109 binds to and negatively regulates signaling of transforming growth factor beta (TGF-β).

Antibodies that specifically bind human ICOS are commercially available and include clone 496920 (available from R&D Systems) and clone NBP1-84393 (available from Novus Biologicals). The nucleic acid sequence for human CD109 is set forth in Accession No. NM_001159587.

I. MART-1

Melanoma antigen recognized by T-cells 1 (MART-1), also known as melan-A, is encoded by the MLANA gene. A fragment of the protein, usually consisting of the nine amino acids 27 to 35, is bound by MHC class I complexes which present it to T cells of the immune system. These complexes can be found on the surface of melanoma cells. Decameric peptides (26-35) are being investigated as cancer vaccines.

Antibodies that specifically bind human MART-1 are commercially available and include clone EP1422Y (available from Novus Biologicals) and clone A103 (available from EMD Millipore). The nucleic acid sequence for human MART-1 is set forth in Accession No. NM_005511.

J. NY-ESO-1

Cancer/testis antigen 1 (NY-ESO-1) is a protein expressed in testis and various cancers. Antibodies that specifically bind human NY-ESO-1 are commercially available and include clone 3F10 (available from OriGene) and clone 2B6 (available from Novus Biologicals). The nucleic acid sequence for human NY-ESO-1 is set forth in Accession No. NM_001327.

III. Methods

Methods are disclosed for predicting the efficacy, potential for relapse, and irAE in a subject diagnosed with cancer and undergoing treatment. Methods are also disclosed for predicting the efficacy, potential for relapse, and irAE in a subject diagnosed with cancer and undergoing treatment based on the levels of specific biomarkers measured in the subject. Methods are also disclosed for treating subjects diagnosed with cancer based on the predicted efficacy, potential for relapse, and irAE in the subject. Methods are also disclosed for treating specific subjects selected from subjects diagnosed with cancer based on the predicted efficacy, potential for relapse, and irAE in the subject. Methods are also disclosed for treating subjects diagnosed with cancer based on the levels of specific biomarkers measured in the subject. Methods are also disclosed for treating specific subjects selected from subjects diagnosed with cancer based on the levels of specific biomarkers measured in the subject.

Methods are also disclosed for not treating subjects diagnosed with cancer with specific therapies based on the predicted efficacy, potential for relapse, and irAE in the subject. Methods are also disclosed for not treating specific subjects selected from subjects diagnosed with cancer with specific therapies based on the predicted efficacy, potential for relapse, and irAE in the subject. Methods are also disclosed for not treating subjects diagnosed with cancer with specific therapies based on the levels of specific biomarkers measured in the subject. Methods are also disclosed for not treating specific subjects selected from subjects diagnosed with cancer with specific therapies based on the levels of specific biomarkers measured in the subject.

Methods are disclosed for predicting the efficacy and clinical benefit in a subject diagnosed with cancer and undergoing treatment. Methods are also disclosed for predicting the efficacy and clinical benefit in a subject diagnosed with cancer and undergoing treatment based on the levels of specific biomarkers measured in the subject. Methods are also disclosed for treating subjects diagnosed with cancer based on the predicted efficacy and clinical benefit in the subject. Methods are also disclosed for treating specific subjects selected from subjects diagnosed with cancer based on the predicted efficacy and clinical benefit in the subject. Methods are also disclosed for treating subjects diagnosed with cancer based on the levels of specific biomarkers measured in the subject. Methods are also disclosed for treating specific subjects selected from subjects diagnosed with cancer based on the levels of specific biomarkers measured in the subject.

Methods are also disclosed for not treating subjects diagnosed with cancer with specific therapies based on the predicted efficacy and clinical benefit in the subject. Methods are also disclosed for not treating specific subjects selected from subjects diagnosed with cancer with specific therapies based on the predicted efficacy and clinical benefit in the subject. Methods are also disclosed for not treating subjects diagnosed with cancer with specific therapies based on the levels of specific biomarkers measured in the subject. Methods are also disclosed for not treating specific subjects selected from subjects diagnosed with cancer with specific therapies based on the levels of specific biomarkers measured in the subject.

The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In preferred embodiments, the cancer is a melanoma. In these embodiments, the method may be used to predict efficacy of CTLA-4 blockade therapy, treatment with other neoplastic drugs, or treatment with a combination of CTLA-4 blockade therapy and other neoplastic drugs.

In preferred embodiments, the cancer is a melanoma. In these embodiments, the method may be used to predict efficacy and clinical benefit of PD-1 blockade therapy, treatment with other neoplastic drugs, or treatment with a combination of PD-1 blockade therapy and other neoplastic drugs.

The disclosed methods involve detecting one or more biomarkers in or on cells in the subject. In preferred embodiments, the one or more biomarkers can be detected in or on PBMCs in the subject, T cells in the subject, T cells in the subject's PBMCs, CD8$^+$ T cells in the subject, CD4$^+$ T cells in the subject, CD8$^+$ T cells in the subject's PBMCs, CD4$^+$ T cells in the subject's PBMCs, or a combination. In most preferred embodiments the one or more biomarkers can be detected in or on PBMCs in the subject. Biomarkers can be detected using standard methods, such as immunoassays to detect proteins in or on the cells, or nucleic acid detection methods to detect gene expression within the cells.

A. Immunoassays

In some aspects, one or more biomarkers are detected using an immunoassay. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, flow cytometry, protein arrays, multiplexed bead arrays, magnetic capture, in vivo imaging, fluorescence resonance energy transfer (FRET), and fluorescence recovery/localization after photobleaching (FRAP/FLAP).

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time long enough for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

A modifier unit such as a radionuclide can be incorporated into or attached directly to any of the compounds described herein by halogenation. In another aspect, the radionuclide can be attached to a linking group or bound by a chelating group, which is then attached to the compound directly or by means of a linker. Radiolabeling techniques such as these are routinely used in the radiopharmaceutical industry.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two-step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Flow cytometry is a well-known technique for counting and/or otherwise examining microscopic particles, such as cells and the like, by passing a stream of fluid in which the particles are suspended through a detection apparatus. The detection apparatus typically relies on detecting the optical response produced as the particles pass through an illuminated region of the device. In some forms, for example, individual particles pass through an illumination zone, typically at a rate on the order of 1,000 cells per second, and detectors, gated electronically, measure the magnitude of a pulse representing the light scattered by the cells. The pulse magnitudes (or other properties) may then be processed to characterize the cells by a particular parameter of interest. For example, the angular dependence of scattered light may provide information on the nature of the scattering particles. More importantly, the fluorescent properties of the particles (which may be caused by appropriate fluorophores being added to the suspension) may provide desired parametric information. Exemplary flow cytometry systems are disclosed in U.S. Pat. No. 5,760,900 and U.S. Patent Publication No. 2008/0186479, which are hereby incorporated by reference herein in their entirety. Those of skill in the art are aware of other systems and techniques for flow cytometry, any of which can be adapted for use with the disclosed methods.

B. Nucleic Acid Detection

In some aspects, one or more biomarkers are nucleic acids, such as mRNA. A number of widely used procedures exist for detecting and determining the abundance of a particular mRNA in a total or poly(A) RNA sample. For example, specific mRNAs can be detected using Northern blot analysis, nuclease protection assays (NPA), in situ hybridization, or reverse transcription-polymerase chain reaction (RT-PCR).

In theory, each of these techniques can be used to detect specific RNAs and to precisely determine their expression level. In general, Northern analysis is the only method that provides information about transcript size, whereas NPAs are the easiest way to simultaneously examine multiple messages. In situ hybridization is used to localize expression of a particular gene within a tissue or cell type, and RT-PCR is the most sensitive method for detecting and quantitating gene expression.

Northern analysis presents several advantages over the other techniques. The most compelling of these is that it is the easiest method for determining transcript size, and for identifying alternatively spliced transcripts and multigene family members. It can also be used to directly compare the relative abundance of a given message between all the samples on a blot. The Northern blotting procedure is straightforward and provides opportunities to evaluate progress at various points (e.g., intactness of the RNA sample and how efficiently it has transferred to the membrane). RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes.

The Nuclease Protection Assay (NPA) (including both ribonuclease protection assays and S1 nuclease assays) is an extremely sensitive method for the detection and quantitation of specific mRNAs. The basis of the NPA is solution hybridization of an antisense probe (radiolabeled or nonisotopic) to an RNA sample. After hybridization, single-stranded, unhybridized probe and RNA are degraded by nucleases. The remaining protected fragments are separated on an acrylamide gel. Solution hybridization is typically more efficient than membrane-based hybridization, and it can accommodate up to 100 µg of sample RNA, compared with the 20-30 µg maximum of blot hybridizations. NPAs are also less sensitive to RNA sample degradation than Northern analysis since cleavage is only detected in the region of overlap with the probe (probes are usually about 100-400 bases in length). NPAs are the method of choice for the simultaneous detection of several RNA species. During solution hybridization and subsequent analysis, individual probe/target interactions are completely independent of one another. Thus, several RNA targets and appropriate controls can be assayed simultaneously (up to twelve have been used in the same reaction), provided that the individual probes are of different lengths. NPAs are also commonly used to precisely map mRNA termini and intron/exon junctions.

In situ hybridization (ISH) is a powerful and versatile tool for the localization of specific mRNAs in cells or tissues. Unlike Northern analysis and nuclease protection assays, ISH does not require the isolation or electrophoretic separation of RNA. Hybridization of the probe takes place within the cell or tissue. Since cellular structure is maintained throughout the procedure, ISH provides information about the location of mRNA within the tissue sample. The procedure begins by fixing samples in neutral-buffered formalin, and embedding the tissue in paraffin. The samples are then sliced into thin sections and mounted onto microscope slides. (Alternatively, tissue can be sectioned frozen and post-fixed in paraformaldehyde.) After a series of washes to dewax and rehydrate the sections, a Proteinase K digestion is performed to increase probe accessibility, and a labeled probe is then hybridized to the sample sections. Radiolabeled probes are visualized with liquid film dried onto the slides, while nonisotopically labeled probes are conveniently detected with colorimetric or fluorescent reagents.

RT-PCR has revolutionized the study of gene expression. It is now theoretically possible to detect the RNA transcript of any gene, regardless of the scarcity of the starting material or relative abundance of the specific mRNA. In RT-PCR, an RNA template is copied into a complementary DNA (cDNA) using a retroviral reverse transcriptase. The cDNA is then amplified exponentially by PCR. As with NPAs, RT-PCR is somewhat tolerant of degraded RNA. As long as the RNA is intact within the region spanned by the primers, the target will be amplified.

Relative quantitative RT-PCR involves amplifying an internal control simultaneously with the gene of interest. The internal control is used to normalize the samples. Once normalized, direct comparisons of relative abundance of a specific mRNA can be made across the samples. It is crucial to choose an internal control with a constant level of expression across all experimental samples (i.e., not affected by experimental treatment). Commonly used internal controls (e.g., GAPDH, β-actin, cyclophilin) often vary in expression and, therefore, may not be appropriate internal controls. Additionally, most common internal controls are expressed at much higher levels than the mRNA being studied. For relative RT-PCR results to be meaningful, all products of the PCR reaction must be analyzed in the linear range of amplification. This becomes difficult for transcripts of widely different levels of abundance.

Competitive RT-PCR is used for absolute quantitation. This technique involves designing, synthesizing, and accurately quantitating a competitor RNA that can be distinguished from the endogenous target by a small difference in size or sequence. Known amounts of the competitor RNA are added to experimental samples and RT-PCR is performed. Signals from the endogenous target are compared with signals from the competitor to determine the amount of target present in the sample.

C. CTLA-4 Blockade Therapies

CTLA-4 (cytotoxic T lymphocyte-associated antigen 4) is a molecule on cytotoxic T lymphocytes that is believed to play a critical role in regulating natural immune responses. The absence or presence of CTLA-4 can augment or suppress the immune system's T-cell response in fighting disease. Antibodies designed to block the activity of CTLA-4 are effective in sustaining an active immune response in its attack on cancer cells. CTLA-4 blockade therapy can, for example, target CTLA-4. The composition or compound used can block the function of the CTLA-4.

For example, Ipilimumab is a fully human antibody that binds to CTLA-4. Ipilimumab was approved by the FDA in March 2011 to treat patients with late-stage melanoma that has spread or cannot be removed by surgery. Additionally, ipilimumab is undergoing clinical trials for the treatment of non-small cell lung carcinoma (NSCLC), small cell lung cancer (SCLC) and metastatic hormone-refractory prostate cancer. Tremelimumab is a fully human IgG2 monoclonal antibody that binds to CTLA-4.

D. Non CTLA-4 Anti-Neoplastic Therapies

Numerous anti-cancer (antineoplastic) drugs are available for treating subjects with cancer. In some embodiments, the disclosed biomarkers may also be used to predict efficacy, relapse, and irAE in a subject treated with one or more of these anti-neoplastic drugs, alone or in combination with CTLA-4 blockade therapy.

E. PD-1 Blockade Therapies

Programmed Death-1 (PD-1) is a negative regulator of T cell activation and proliferation that mediates suppressive action by binding to its ligands PD-L1 and PD-L2. T cell exhaustion is a state of T cell dysfunction that arises during many chronic infections and cancer. Over the last few years, it has been established that PD-1 plays an active and reversible role in T cell exhaustion. Under physiological conditions, PD-1 is induced after T cell activation and serves as an inhibitory feedback to dampen the TCR signaling cascade and prevent excessive T cell activation. PD-1 plays also an important role in the tolerance to self antigens. Anti-PD-1 antibodies, such as BMS-936558 and BMS-936559, have been identified as potential cancer therapeutic. BMS-936558 is an antibody against PD-1 and is currently in clinical trials. PD-1 blockade therapy can target either or both the PD-1 receptor or the ligand of the PD-1 receptor. The composition or compound used can block the function of the PD-1 receptor.

F. Non PD-1 Anti-Neoplastic Therapies

Numerous anti-cancer (antineoplastic) drugs are available for treating subjects with cancer. In some embodiments, the disclosed biomarkers may also be used to predict efficacy and clinical benefit in a subject treated with one or more of these anti-neoplastic drugs, alone or in combination with PD-1 blockade therapy.

Antineoplastic drugs include Acivicin, Aclarubicin, Acodazole Hydrochloride, AcrQnine, Adozelesin, Aldesleukin, Altretamine, Ambomycin, Ametantrone Acetate, Aminoglutethimide, Amsacrine, Anastrozole, Anthramycin, Asparaginase, Asperlin, Azacitidine, Azetepa, Azotomycin, Batimastat, Benzodepa, Bicalutamide, Bisantrene Hydrochloride, Bisnafide Dimesylate, Bizelesin, Bleomycin Sulfate, Brequinar Sodium, Bropirimine, Busulfan, Cactinomycin, Calusterone, Caracemide, Carbetimer, Carboplatin, Carmustine, Carubicin Hydrochloride, Carzelesin, Cedefingol, Chlorambucil, Cirolemycin, Cisplatin, Cladribine, Crisnatol Mesylate, Cyclophosphamide, Cytarabine, Dacarbazine, Dactinomycin, Daunorubicin Hydrochloride, Decitabine, Dexormaplatin, Dezaguanine, Dezaguanine Mesylate, Diaziquone, Docetaxel, Doxorubicin, Doxorubicin Hydrochloride, Droloxifene, Droloxifene Citrate, Dromostanolone Propionate, Duazomycin, Edatrexate, Eflomithine Hydrochloride, Elsamitrucin, Enloplatin, Enpromate, Epipropidine, Epirubicin Hydrochloride, Erbulozole, Esorubicin Hydrochloride, Estramustine, Estramustine Phosphate Sodium, Etanidazole, Ethiodized Oil I 131, Etoposide, Etoposide Phosphate, Etoprine, Fadrozole Hydrochloride, Fazarabine, Fenretinide, Floxuridine, Fludarabine Phosphate, Fluorouracil, Flurocitabine, Fosquidone, Fostriecin Sodium, Gemcitabine, Gemcitabine Hydrochloride, Gold Au 198, Hydroxyurea, Idarubicin Hydrochloride, Ifosfamide, Ilmofosine, Interferon Alfa-2a, Interferon Alfa-2b, Interferon Alfa-n1, Interferon Alfa-n3, Interferon Beta-Ia, Interferon Gamma-Ib, Iproplatin, Irinotecan Hydrochloride, Lanreotide Acetate, Letrozole, Leuprolide Acetate, Liarozole Hydrochloride, Lometrexol Sodium, Lomustine, Losoxantrone Hydrochloride, Masoprocol, Maytansine, Mechlorethamine Hydrochloride, Megestrol Acetate, Melengestrol Acetate, Melphalan, Menogaril, Mercaptopurine, Methotrexate, Methotrexate Sodium, Metoprine, Meturedepa, Mitindomide, Mitocarcin, Mitocromin, Mitogillin, Mitomalcin, Mitomycin, Mitosper, Mitotane, Mitoxantrone Hydrochloride, Mycophenolic Acid, Nocodazole, Nogalamycin, Ormaplatin, Oxisuran, Paclitaxel, Pegaspargase, Peliomycin, Pentamustine, Peplomycin Sulfate, Perfosfamide, Pipobroman, Piposulfan, Piroxantrone Hydrochloride, Plicamycin, Plomestane, Porfimer Sodium, Porfiromycin, Prednimustine, Procarbazine Hydrochloride, Puromycin, Puromycin Hydrochloride, Pyrazofurin, Riboprine, Rogletimide, Safmgol, Safingol Hydrochloride, Semustine, Simtrazene, Sparfosate Sodium, Sparsomycin, Spirogermanium Hydrochloride, Spiromustine, Spiroplatin, Streptonigrin, Streptozocin, Strontium Chloride Sr 89, Sulofenur, Talisomycin, Taxane, Taxoid, Tecogalan Sodium, Tegafur, Teloxantrone Hydrochloride, Temoporfin, Teniposide, Teroxirone, Testolactone, Thiamiprine, Thioguanine, Thiotepa, Tiazofurin, Tirapazamine, Topotecan Hydrochloride, Toremifene Citrate, Trestolone Acetate, Triciribine Phosphate, Trimetrexate, Trimetrexate Glucuronate, Triptorelin, Tubulozole Hydrochloride, Uracil Mustard, Uredepa, Vapreotide, Verteporfin, Vinblastine Sulfate, Vincristine Sulfate, Vindesine, Vindesine Sulfate, Vinepidine Sulfate, Vinglycinate Sulfate, Vinleurosine Sulfate, Vinorelbine Tartrate, Vinrosidine Sulfate, Vinzolidine Sulfate, Vorozole, Zeniplatin, Zinostatin, Zorubicin Hydrochloride.

G. Monitoring Treatment

Biomarkers have also been discovered that can be used to monitor subjects following treatment to determine the effectiveness of the treatment and/or the prognosis for the subject. For example, certain biomarkers are associated with patients less likely to relapse or an irAE following CTLA-4 blockade therapy. As another example, certain biomarkers are associated with patients more likely to respond to treatment following PD-1 blockade therapy.

A decrease of $Ki67^+EOMES^+CD4^+$ cells in CD4+ T cells, a decrease in expression of CCR7 on $CD8^+$ T cells, a decrease in the frequency of $CCR7^+CD8^+$, cells in $CD8^+$ T cells, an increase in expression of TGFβR3 on $CD8^+$ T cells, an increase in expression of EOMES in CD8+ cells, an increase in frequency of $EOMES^+CD8^+$ cells in $CD8^+$ T cells, an increase in the frequency of $GranzymeB^+EOMES^+CD8^+$ cells in $CD8^+$ T cells, an increase in the frequency of $Perforin^+EOMES^+CD8^+$ cells in $CD8^+$ T cells, an increase in the frequency of $CTLA-4^+CD4^+$ cells in $CD4^+$ T cells, or a combination indicates a higher risk of relapse (that is, a poorer prognosis or an indication that therapy is not successful) in subjects with cancer that have been treated with CTLA-4 blockade therapy. A decrease of $Ki67^+CD8^+$ cells in $CD8^+$ T cells, a decrease of $CD71^+CD8^+$ cells in $CD8^+$ T cells, a decrease of $ICOS^+CD8^+$ cells in $CD8^+$ T cells, a decrease of $PD-1^+CD8^+$ cells in $CD8^+$ T cells, or a combination indicates a higher risk of developing irAE (that is, a poorer prognosis or an indication that therapy is not successful) in subjects with cancer that have been treated with CTLA-4 blockade therapy. Thus, these biomarkers can be used to assess the progress and effectiveness of CTLA-4 blockade treatment.

Figure 8A:
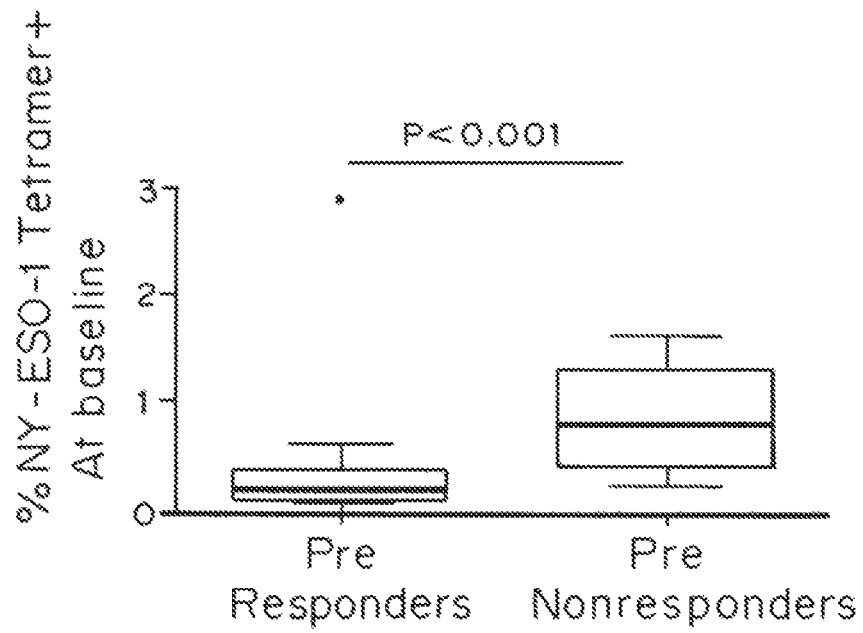
FIGS. 8A, 8B, 8C, and 8D are graphs of marker differences in responders and nonresponders to treatment with BMS-936558. 33 patients were measured with baseline of the tetramers; 25 with 12 weeks measurement; 13 responders and 12 non-responders. 8 patients only have baseline who are non-responders.
Figure 8B:
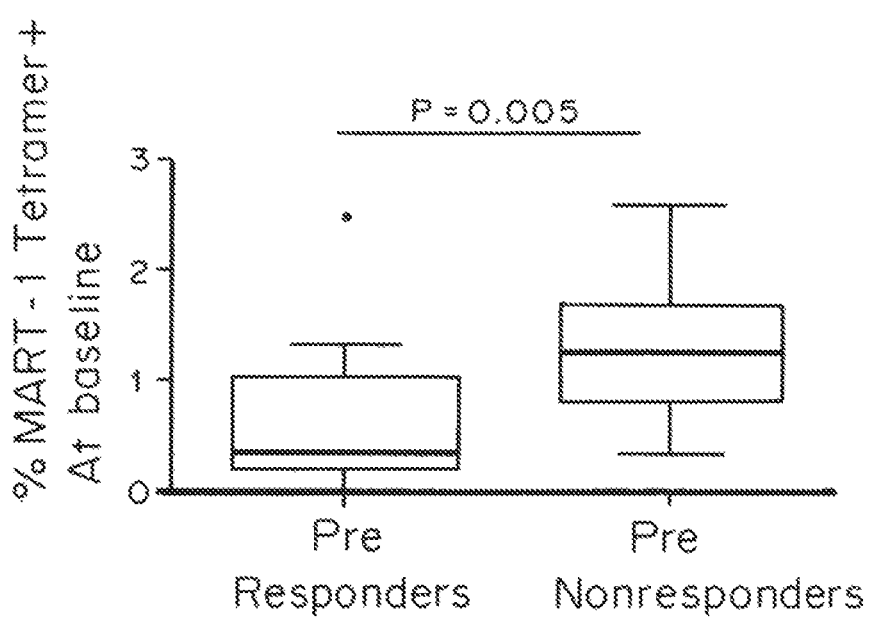
Figure 8C:
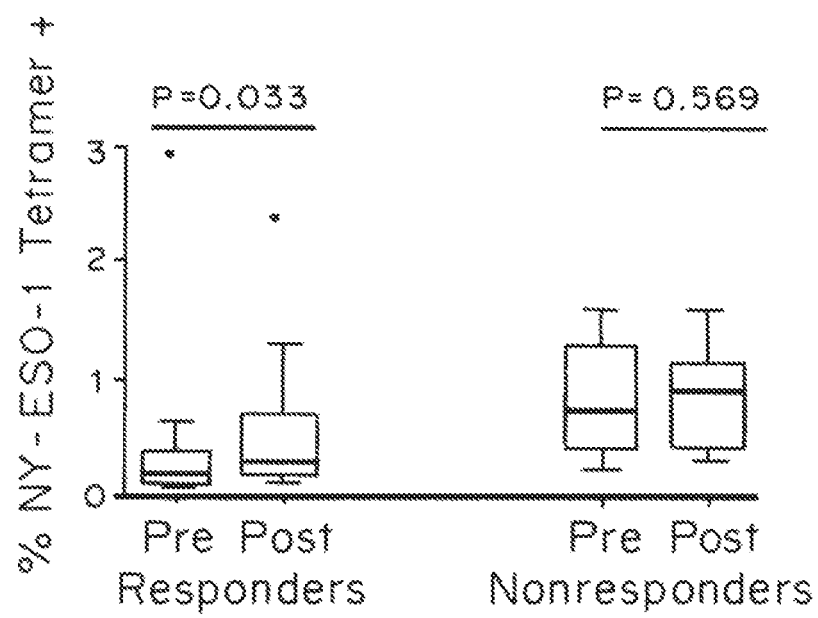
Figure 8D:
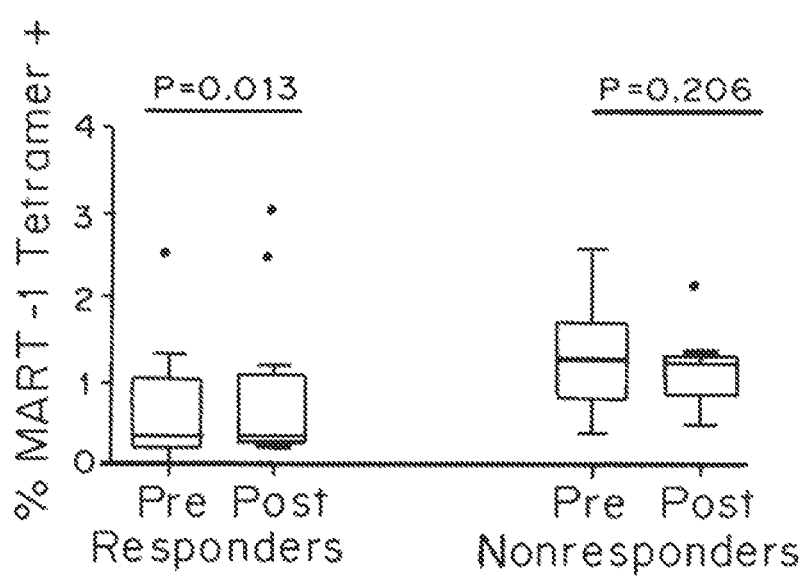
Figure 9A:
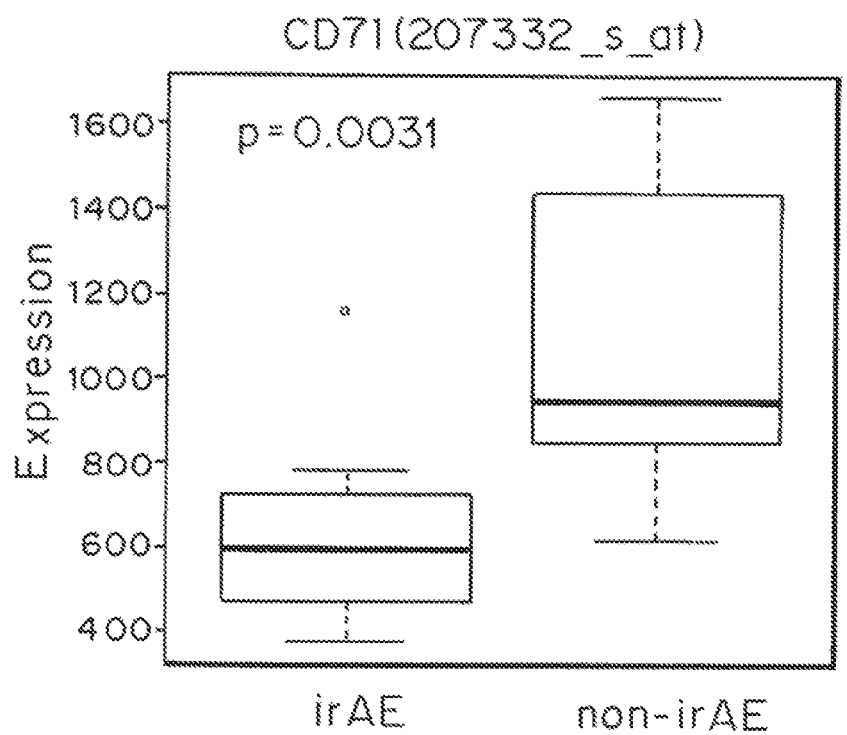
FIGS. 9A and 9B are Box plots of CD71 baseline expression in irAE group and non-irAE group of the patients. The line inside the rectangle indicated the median of the baseline CD71 expression distribution. The upper and lower boundaries of the rectangle indicated the upper quartile and the lower quartile, respectively. Two lines (the whiskers) are drawn from the rectangle to the extreme values (highest and lowest expression level of baseline CD71 expression in CD4+ T cells).
Figure 9B:
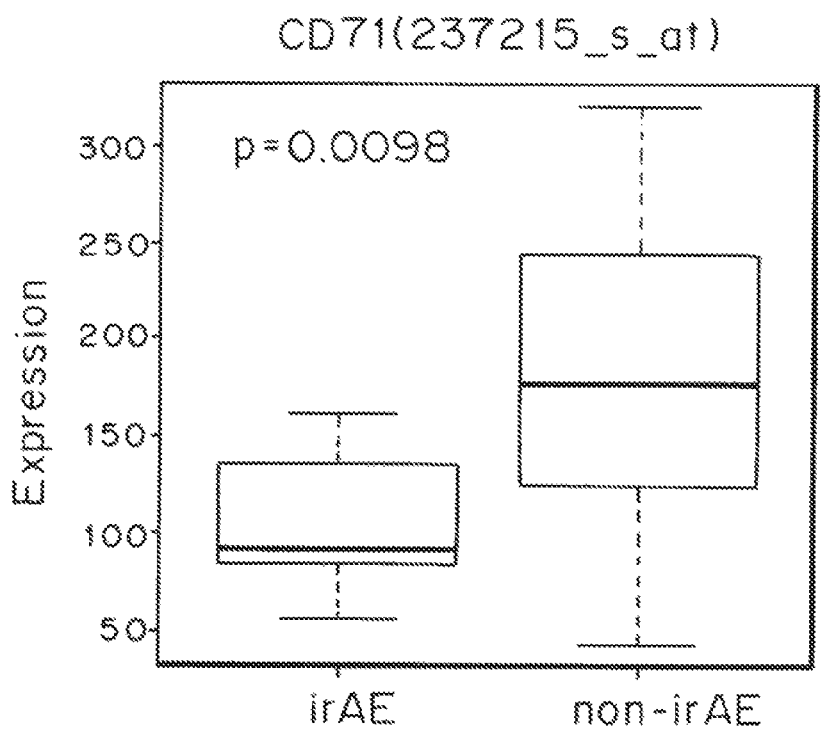
Figure 10:
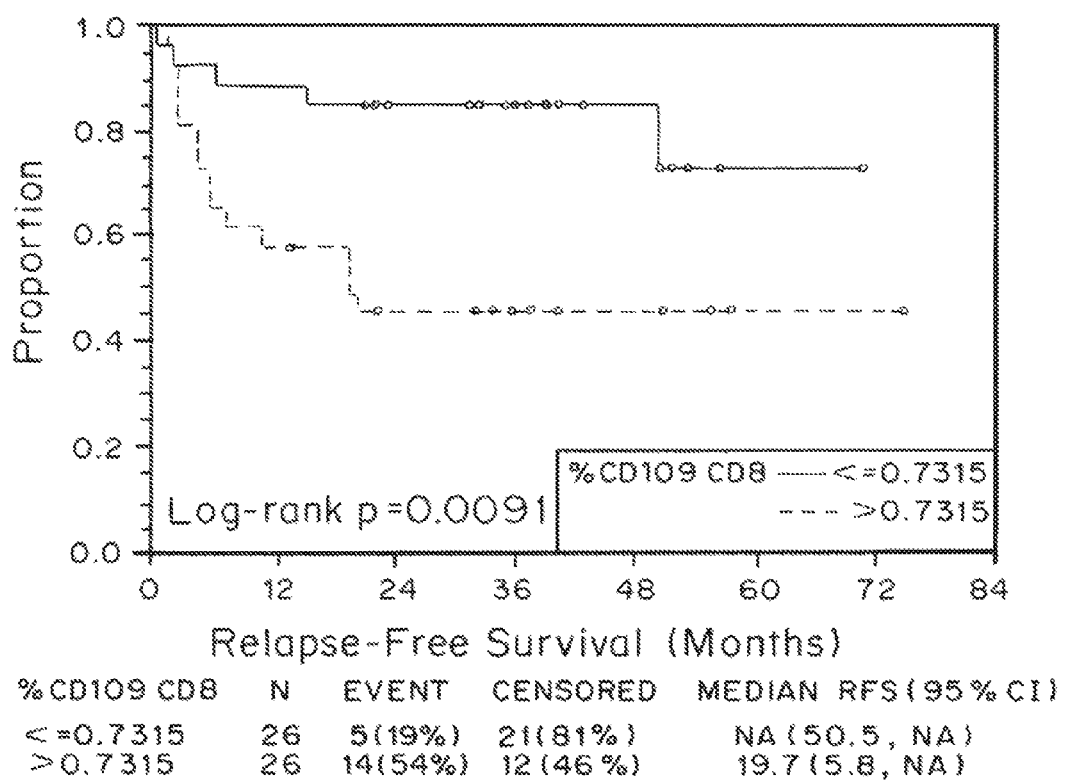
FIG. 10 is a graph of Kaplan-Meier curves for association of baseline biomarkers (percentage of $CD8^+$ T cells that are $CD109^+$) with relapse free survival.

An increase in $NY-ESO-1^+CD8^+$ cells in $CD8^+$ T cells or an increase in $MART-1^+CD8^+$ cells in CD8+ T cells, or a combination indicates a lower risk of relapse (that is, a better prognosis or an indication that therapy is successful) in subjects with cancer that have been treated with PD-1 blockade therapy (see FIGS. 8C and 8D).

The disclosed methods include the determination, identification, indication, correlation, diagnosis, prognosis, etc. (which can be referred to collectively as "identifications") of subjects, diseases, conditions, states, etc. based on measurements, detections, comparisons, analyses, assays, screenings, etc. For example, subjects diagnosed with cancer can be identified for specific treatments (or avoidance of specific treatments) based on the levels of specific biomarkers measured in the subject. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc., a subject identified in any of the disclosed methods. Also disclosed are methods comprising treating, monitoring, following-up with, advising, etc., a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

EXAMPLES

Example 1: Biomarkers on Melanoma Patient T Cells Associated with Ipilimumab Therapy Materials and Methods Patients Between June 2004 and December 2008, 75 patients (39 at the University of Southern California, Norris Cancer Center and 36 at the Moffitt Cancer Center) with resected stage IIIC/IV melanoma received ipilimumab with or without a peptide vaccine. The demographic and clinic outcomes of the patients for this study were shown in Table 1, which have been reported previously (Sarnaik A A, et al. *Clin Cancer Res.* 17(4):896-906 (2010)) with updated follow-up: three patients died (R DOD); one patient relapsed and was resected with no evidence of disease (R NED) instead of no evidence of disease (NED). Toxicity was assessed by National Cancer Institute Common Terminology Criteria for Adverse Events, version 3.0. The protocol was approved by the University of Southern California/Los Angeles County and University of South Florida Institutional Review Boards, and all patients provided written informed consent.

TABLE 1

Demographic data for the total 55 patients

| Variable | Level | n (%) |
| --- | --- | --- |
| dosage | 10 mg/kg | 40 (72.7) |
|  | 3 mg/kg | 15 (27.3) |
| gender | F | 21 (38.2) |
|  | M | 34 (61.8) |

TABLE 1-continued

Demographic data for the total 55 patients

| Variable | Level | n (%) |
|---|---|---|
| stage | III | 24 (43.6) |
| | IV | 31 (56.4) |
| HLA_A2 | A2+ | 34 (61.8) |
| | A2− | 21 (38.2) |
| irAE | N | 31 (56.4) |
| | Y | 24 (43.6) |
| Outcome | NED | 35 (63.6) |
| | Relapse | 20 (36.4) |

PBMC Collection, Preparation and T Cells Purification

Apheresis with exchange of 5 to 7 liters was performed within 1 week before and 6 months after the initiation of therapy, after four doses of ipilimumab. Heparinized blood samples were collected after 2 doses of ipilimumab, 3 months after the initiation of therapy. PBMC were isolated from pre-, 3-month and 6-month post-ipilimumab treatment specimens by Lymphoprep (Greiner Bio-One, Longwood, Fla.) density gradient centrifugation. PBMC were counted, then frozen in 90% heat inactivated human AB serum (HS, Omega Scientific, Tarzana, Calif.) and 10% dimethyl sulfoxide (DMSO) (Sigma, St Louis, Mo.) and stored in secured liquid nitrogen freezers at −168° C. until use.

Cryopreserved pre- and 6-month post-treatment PBMC of each patient were thawed immediately into pre-warmed AIM-V media (Invitrogen Corporation, Grand Island, N.Y.) supplemented with 5% HS. For microarray analysis, PBMCs were sorted as follows: cells were stained with CD3-FITC (BD Bioscience, San Diego, Calif.), CD4-PE (BD Bioscience), CD8-APC (BD Bioscience) and CD19-PECy7 (BD Bioscience) for 30 min at 4° C. After extensive wash, PBMCs were stained with DAPI nucleic acid dye (Invitrogen) to exclude dead and dying cells. After washes with staining buffer (PBS+0.5% HS), PBMC were re-suspended in staining buffer for flow cytometry sorting. $CD3^+CD4^+CD8^-$, $CD3^+CD8^+CD4^-$ T cells and $CD3^-CD19^+$ B cell populations were collected by Aria (BD Bioscience, San Jose). The purity of the sorted specific cell populations were consistently ≥99%.

Microarray Analysis

The sorted cells were pelleted and re-suspended in a RLT lysis buffer (Qiagen Science, Valencia, Calif.), and delivered to the Microarray Core (Moffitt Cancer Center, Tampa, Fla.) for expression array analysis. RNA from the sorted cell populations were DNase-treated and extracted using the Qiagen RNeasy mini-prep according to the manufacturer's protocol (Qiagen). The Nugen Message Amp Premier kit was used to amplify 100 nanograms of total RNA (Nugen Technologies, San Carlos, Calif.). Briefly, the extracted poly-(A) RNA was specifically converted to cDNA, amplified and labeled with biotin following the procedure initially described by Van Gelder et al. (Van Gelder R N, et al. *Proc Natl Acad Sci USA*. 87:1663-7 (1990)). Biotin-labeled cDNA was hybridized onto Affymetrix U133 Plus 2.0 microarrays. The hybridization, staining, and scanning of the chips followed the procedures outlined in the Affymetrix technical manual (Liu W M, et al. *Bioinformatics*. 18:1593-9 (2002)). Scanned output files were visually inspected for hybridization artifacts and then analyzed by using Affymetrix GeneChip Operating Software (GCOS). Arrays were scaled to an average intensity of 500 and analyzed independently. The GCOS software used a statistical algorithm to determine the signal intensity of a transcript from the behavior of 11 different oligonucleotide probes designed to detect the same gene. Probe sets that yielded a p-value less than 0.002 were identified as changed. Alternatively, signal intensity was calculated by the robust multi-array analysis method (RMA) developed by Irizarry et al (Irizarry R A, et al. *Nucleic Acids Res*. 31:e15 (2003)). Gene changes were then selected using the fold-change cut-off available in RMA or using the Significance Analysis of Microarrays (SAM) technique of Tusher et al. (Tusher V G, et al. *Proc Natl Acad Sci USA*. 98:5116-21 (2001)).

Surface and Intracellular Staining

For cell surface staining, $1-2\times10^6$ PBMC in 100 µl PBS were stained with the Aqua-live/dead fixable dye (Invitrogen) at 4° C. for 30 min. After washing, PBMC were stained with fluorochrome-conjugated antibodies against cell surface markers prepared as a master-mix-solution for 30 min at 4° C. The antibodies for surface markers were purchased from BD Bioscience unless otherwise specified: CD3-AlexFluor 700, CD4-PECy7, CD8-PERCPCy5.5, ICOS-PE, CCR7-FITC (R&D Systems, Minneapolis, Minn.), CCR7-PE (R &D Systems), CXCR3-FITC (R & D Systems), CD109-PE, CD45RA-FITC, CD28-APC (eBioscience, San Diego, Calif.), IL-7R-APC (R&D system), CD25-FITC, TGFβR3-PE (R&D Systems) and MIC-A-APC (R&D Systems). The fluorescent minus one and isotype control was included in each experiment in order to appropriately set the gates. A total of 300,000 live single lymphocytes were acquired on a LSR II flow cytometer (BD Bioscience). Analysis gates were set on single live lymphocytes defined by scatter characteristics and Aqua negative staining. First, the lymphocytes were gated by the forward and sideward scatters, then the single cells were gated by forward and sideward width and height. The single live lymphocytes were observed by gating on aqua negative stained single lymphocytes. In the whole study, we observed the biomarkers on CD4 and $CD8^+$ T cells.

For intracellular staining, $2-3\times10^6$ PBMC in 100 µl staining buffer were treated as above, then fixed with a freshly prepared Fixation/Permeabilization working solution (eBioscience) at 4° C. for 30 min. After wash with permeabilization buffer (eBioscience), the cells were stained with intracellular markers: Ki67-FITC (Abcam, Cambridge, Mass.), EOMESodermin (EOMES)-Alex Fluor 647 (eBioscience), granzyme B-FITC, perforin-PE, FoxP3-APC (eBioscience), GATA 3-Alex Fluor 647 (eBioscience), cleaved caspase III-PE for 30 min at 4° C. Cells were then washed in the permeabilization buffer and resuspended in staining buffer for flow cytometry acquisition.

For the standardization of flow cytometry assays and the consistency of daily performance, a normal PBMC sample was stained and run on flow cytometry in parallel with the subject samples and Spherotech rainbow fluorescent particles (Spherotech, Inc, Lake Forest, Ill.) were run before running samples for alignment of the optical system of the flow cytometer in each channel.

Flow Cytometry Analysis

Flow cytometry data were analyzed using Flowjo software (Version 9.0.2, Tree Star, Inc., Asland, Oreg.). The mean fluorescence intensity (MFI) and frequency (%) of each marker was measured for $CD4^+$ and $CD8^+$ T cells.

Statistical Analysis

Descriptive summary statistics, that is, frequency and percentage for discrete variables and mean (standard deviation: STD), interquartiles and median (range) for continuous variables, were reported. Both point estimates and their confidence intervals (CIs) were provided for parameters of interest, e.g., mean change or odds ratio (OR). Wilcoxon signed-rank test was used to test whether changes in immunological biomarker parameters between pre-, 3-month and 6-month post-ipilimumab were statistically significant. Both absolute change and relative change, i.e., post-pre and (post-pre)/pre*100, were analyzed to account for a potentially better normalization under the log scale for the immunological biomarker parameters under investigation. Confidence intervals were set at the 95% level. Univariable logistic regression models were employed to explore the effect of absolute change as well as relative change of each biomarker on disease outcome (NED vs. relapsed) and dose limiting irAE (Yes vs. No). The CI for OR based on the univariable logistic regression model results were calculated for an increment that equals one half of the interquartile range of the corresponding change variable for the biomarker. A p-value of ≤0.05 was considered statistically significant.

Results

Changes in Gene Expression Patterns of $CD4^+$ and $CD8^+$ T Cells Induced by Ipilimumab To assess the effect of ipilimumab on global gene expression in $CD4^+$ and $CD8^+$ T cells in vivo, microarray analysis was conducted on T cells purified by flow cytometry from PBMCs collected from 12 resected melanoma patients pre- and 6-month post-ipilimumab treatment (Table 6a). The genes whose expression were most significantly altered in $CD4^+$ and $CD8^+$ T cells by ipilimumab treatment are listed in Tables 2a and 2b, categorized by T cell biology and function. The genes were grouped into cell cycle, cytokine-related, chemokine-related, T cell activation and proliferation signal-related, survival and apoptotic signal-related, kinase-related and heat shock protein family-related genes. It is worthy to note that the genes most impacted by ipilimumab were cell cycle related in both $CD4^+$ and $CD8^+$ T cells. Ipilimumab appeared to release the arrested cell cycle in $CD4^+$ and $CD8^+$ T cells as evidenced by significantly up-regulated CDC2 (Tables 2a and 2b), and other cell cycle related genes. Fold change was filtered as an increase ≥1.2 or a decrease ≤0.8-fold, and was statistically significantly different with p≤0.03 by paired Student T-test. The reported genes were all consistently changed in ≥66.67% patients' pre and post ipilimumab by Affymetrix present/absent call.

TABLE 6a

Patient Demographics for the Microarray cohort (n = 12)

| Variable | Level | n (%) |
|---|---|---|
| gender | F | 4 (33.3) |
|  | M | 8 (66.7) |
| stage | III | 4 (33.3) |
|  | IV | 8 (66.7) |
| HLA A2 | A2+ | 7 (58.3) |
|  | A2− | 5 (41.7) |
| dosage | 10 mg/kg | 12 (100) |
|  | 3 mg/kg | 0 (0) |
| irAE | N | 7 (58.3) |
|  | Y | 5 (41.7) |
| Outcome | NED | 12 (100) |
|  | Relapse | 0 (0) |

TABLE 2a genes impacted by ipilimumab in CD4+ T cells

| Gene symbol Gene name | Fold change | p-value | FDR | Pre-Mean ± SD | Post-Mean ± SD |
|---|---|---|---|---|---|
| Cell cycle-related | | | | | |
| CDC2 cell division cycle 2, G1 to S and G2 to M | 1.98, 1.76, 1.51 | 0.0090, 0.0245, 0.0189 | 0.0409, 0.0723, 0.0568 | 18.61 ± 4.41, 7.05 ± 1.44, 21.16 ± 6.79 | 36.92 ± 21.36, 12.41 ± 6.42, 36.37 ± 17.62 |
| TYMS thymidylate synthetase | 2.78, 2.77 | 0.0142, 0.0075 | 0.0432, 0.0408 | 66.68 ± 59.31, 129.75 ± 58.10 | 185.59 ± 185.36, 358.99 ± 254.47 |
| CCNB2 cyclin B2 | 2.08 | 0.0142 | 0.0434 | 28.17 ± 11.75 | 58.49 ± 45.13 |
| CDK7 cyclin-dependent kinase 7 | 1.26 | 0.0074 | 0.0408 | 214.08 ± 75.01 | 270.13 ± 106.34 |
| Cytokines-related | | | | | |
| PGDS prostaglandin D2 synthase, hematopoietic | 2.2 | 0.0024 | 0.0393 | 14.20 ± 5.42 | 31.30 ± 14.57 |
| TGFBR3 transforming growth factor b RIII | 1.51, 1.39 | 0.0048, 0.0111 | 0.04044, 0.0411 | 489.68 ± 470.87, 505.71 ± 304.47 | 740.39 ± 581.83, 701.22 ± 246.45 |
| IFNg interferon, g | 1.46 | 0.0255 | 0.0751 | 138.35 ± 104.72 | 201.55 ± 120.78 |
| IL12A interleukin 12 A | 1.33 | 0.001 | 0.0375 | 11.81 ± 2.00 | 15.73 ± 4.01 |
| IL-7 interleukin 7 | 1.28 | 0.0169 | 0.0511 | 15.43 ± 10.42 | 19.73 ± 8.89 |
| STAT1 signal transducer and activator of transcription 1 | 1.28 | 0.0081 | 0.0409 | 1141.96 ± 330.11 | 1460.67 ± 577.64 |

TABLE 2a-continued genes impacted by ipilimumab in CD4+ T cells

| Gene symbol Gene name | Fold change | p-value | FDR | Pre-Mean ± SD | Post-Mean ± SD |
|---|---|---|---|---|---|
| SCYE1 small inducible cytokine subfamily E, member 1 | 1.27 | 0.0103 | 0.041 | 278.24 ± 100.74 | 352.82 ± 149.81 |
| IL-7R interleukin 7 receptor | 0.80, 0.74 | 0.0061, 0.0011 | 0.0406, 0.0375 | 5219.38 ± 1457.55, 3309.89 ± 1296.32 | 4291.38 ± 1772.32, 2467.81 ± 1094.22 |
| IL-2Ra interleukin 2 receptor, a | 0.69 | 0.01811 | 0.0544 | 113.56 ± 58.89 | 79.12 ± 39.28 |
| IL-15 interleukin 15 | 0.74 | 0.0032 | 0.0398 | 54.76 ± 39.59 | 40.63 ± 31.09 |
| TNFSF8 tumor necrosis factor superfamily, member 8 | 0.73 | 0.0202 | 0.0605 | 248.08 ± 148.25 | 181.53 ± 92.03 |
| Chemokines-related | | | | | |
| CCR3 Chemokine (C-C motif) receptor 3 | 1.52 | 0.0092 | 0.041 | 19.73 ± 5.59 | 29.92 ± 13.46 |
| ITGB1 integrin, b1 (antigen CD29) | 1.29, 1.20 | 0.0055, 0.0012 | 0.0405, 0.0375 | 1449.91 ± 772.02, 396.68 ± 336.59 | 1867.82 ± 802.10, 476.25 ± 376.51 |
| CXCR3 chemokine receptor 3 | 1.29 | 0.0286 | 0.0825 | 47.04 ± 23.35 | 60.53 ± 33.18 |
| CXCR7 chemokine receptor 7 | 0.75 | 0.0205 | 0.0614 | 83.62 ± 25.83 | 63.45 ± 25.78 |
| ITGA6 integrin, a6 | 0.72 | 0.0211 | | | |
| Activation, proliferation and differentiation-related | | | | | |
| MKI67 antigen identified by monoclonal antibody Ki-67 | 1.98, 1.69 | 0.0165, 0.0104 | 0.0498, 0.0410 | 41.58 ± 22.80, 19.37 ± 9.50 | 82.16 ± 62.67, 32.73 ± 20.37 |
| ICOS inducible T-cell costimulator | 1.49 | 0.0011 | 0.0375 | 587.76 ± 294.69 | 874.26 ± 397.84 |
| GATA3 GATA binding protein 3 | 1.43 | 0.0124 | 0.042 | 284.77 ± 189.82 | 406.03 ± 268.34 |
| CTLA-4 cytotoxic T-lymphocyte-associated protein 4 | 1.37, 1.37 | 0.0023, 0.0249 | 0.0392, 0.0734 | 163.55 ± 83.74, 511.58 ± 260.28 | 224.53 ± 114.73, 700.23 ± 359.54 |
| CD38 CD38 molecule | 1.36 | 0.0075 | 0.0408 | 32.73 ± 13.37 | 44.62 ± 20.04 |
| MICA MHC class I polypeptide-related sequence A | 0.7 | 0.0015 | 0.0379 | 120.33 ± 67.61 | 84.36 ± 51.72 |
| BCL family-related | | | | | |
| Bcl3 B-cell CLL/lymphoma 3 | 1.56 | 0.0036 | 0.0400 | 199.55 ± 112.65 | 311.36 ± 120.66 |
| BAK1 Bcl2-antagonist/killer 1 | 1.26 | 2.00E−04 | 0.0365 | 130.50 ± 27.61 | 164.92 ± 33.45 |
| Bcl2L11 Bcl2-like 11 | 1.24, 1.21 | 0.0067, 0.0369 | 0.0407, 0.1053 | 314.36 ± 77.54, 442.48 ± 299.18 | 388.54 ± 79.60, 536.88 ± 388.57 |
| BCLAF1 Bcl2-associated transcription factor 1 | 1.21 | 0.0234 | 0.0695 | 61.14 ± 14.91 | 73.89 ± 26.64 |

TABLE 2a-continued genes impacted by ipilimumab in CD4+ T cells

| Gene symbol Gene name | Fold change | p-value | FDR | Pre-Mean ± SD | Post-Mean ± SD |
|---|---|---|---|---|---|
| Bcl2 | 0.79, | 0.0246, | 0.0726, | 617.68 ± 266.67, | 492.80 ± 272.63, |
| B-cell | 0.72, | 0.0158, | 0.0479, | 189.15 ± 81.00, | 137.91 ± 40.11, |
| CLL/lymphoma 2 | 0.63 | 0.0050 | 0.0404 | 427.68 ± 327.43 | 272.97 ± 207.62 |
| Apoptosis MAP kinase and protein kinase-related | | | | | |
| ANXA5 annexin 5 | 1.32 | 0.0271 | 0.0794 | 599.68 ± 269.08 | 793.89 ± 425.06 |
| MAPK6 mitogen-activated protein kinase 6 | 1.31 | 0.0261 | 0.0768 | 209.49 ± 142.30 | 273.63 ± 202.36 |
| PPP1CC protein phosphatase 1, catalytic subunit, g isoform | 1.23 | 0.0152 | 0.0462 | 998.56 ± 432.59 | 1225.87 ± 571.01 |
| CASP7 caspase 7, apoptosis-related cysteine peptidase | 1.22 | 0.0145 | 0.0441 | 141.11 ± 41.72 | 171.83 ± 48.77 |
| MAP2K6 mitogen-activated protein kinase kinase 6 | 0.77 | 0.0105 | 0.0410 | 77.3 ± 41.24 | 59.77 ± 33.17 |
| ANXA11 annexin 11 | 0.75 | 0.0003 | 0.0368 | 93.23 ± 20.45 | 70.21 ± 31.98 |
| ATF7 activating transcription factor 7 | 0.75 | 0.0252 | 0.0743 | 170.44 ± 120.64 | 128.30 ± 107.21 |
| MAP4K4 mitogen-activated protein kinase kinase kinase 4 | 0.63 | 0.0095 | 0.041 | 137.49 ± 51.60 | 86.97 ± 29.96 |
| CASP10 caspase 10, apoptosis-related cysteine peptidase | 0.62 | 0.004 | 0.0401 | 62.63 ± 27.12 | 39.11 ± 15.88 |

TABLE 2b genes impacted by ipilimumab in CD8+ T cells

| Gene symbol Gene name | Fold change | p-value | FDR | Pre-Mean ± SD | Post-Mean ± SD |
|---|---|---|---|---|---|
| Cell cycle-related | | | | | |
| CDCA2 cell division cycle associated 2 | 1.95 | 0.0189 | 0.0647 | 12.86 ± 6.07 | 25.11 ± 16.20 |
| CDC2 cell division cycle 2, G1 to S and G2 to M | 1.81, 1.64 | 0.0300, 0.0274 | 0.0897, 0.0827 | 18.37 ± 6.09, 20.92 ± 6.16 | 33.23 ± 21.15, 34.31 ± 21.02 |
| CDCA7 Cell division cycle associated 7 | 1.67 | 0.0113 | 0.0647 | 87.63 ± 93.37 | 146.50 ± 111.23 |
| Cytokines-related | | | | | |
| TNFSF4 tumor necrosis factor superfamily, member 4 | 0.58 | 0.0082 | 0.0647 | 40.88 ± 27.10 | 23.93 ± 14.71 |
| Chemokines-related | | | | | |
| CXCR3 chemokine (C-X-C motif) receptor 3 | 1.25 | 0.0036 | 0.0647 | 54.98 ± 21.50 | 68.96 ± 21.37 |
| ITGAV integrin, aV (antigen CD51) | 0.80 | 5.00E−04 | 0.0647 | 114.65 ± 54.10 | 91.78 ± 42.91 |

TABLE 2b-continued genes impacted by ipilimumab in CD8+ T cells

| Gene symbol Gene name | Fold change | p-value | FDR | Pre-Mean ± SD | Post-Mean ± SD |
|---|---|---|---|---|---|
| CXCR7 chemokine (C-X-C motif) receptor 7 | 0.73 | 0.0268 | 0.081 | 92.65 ± 43.71 | 68.45 ± 33.28 |
| Activation Differentiation and Interaction-related | | | | | |
| HLA-DRB4 major histocompatibility complex, class II, DR b4 | 1.4 | 0.0163 | 0.0647 | 28.04 ± 26.29 | 39.18 ± 37.40 |
| GATA3 GATA binding protein 3 | 1.39, 1.35 | 0.0100, 0.0026 | 0.0647, 0.0647 | 178.84 ± 104.07, 139.84 ± 44.14 | 248.93 ± 148.36, 188.83 ± 75.51 |
| HLA-DRA major histocompatibility complex, class II, DR a | 1.38 | 0.0193 | 0.0647 | 540.53 ± 402.57 | 745.47 ± 350.32 |
| CD6 CD6 molecule (CD166 receptor) | 1.32 | 0.0248 | 0.0754 | 179.47 ± 95.79 | 236.58 ± 157.76 |
| CD5 CD5 molecule | 1.22 | 0.0181 | 0.0647 | 103.58 ± 38.21 | 126.47 ± 45.17 |
| CD209 CD209 molecule | 1.20 | 0.0288 | 0.0865 | 36.73 ± 4.88 | 44.08 ± 7.60 |
| EOMES Eomesodermin | 0.69 | 0.0292 | 0.0877 | 1063.26 ± 642.42 | 738.05 ± 445.38 |
| Apoptosis, MAP Kinases-related | | | | | |
| TIAM1 T-cell lymphoma invasion and metastasis 1 | 1.68 | 0.0105 | 0.0647 | 83.63 ± 67.00 | 140.61 ± 116.68 |
| ANXA5 annexin 5 | 1.31 | 0.0114 | 0.0647 | 576.93 ± 278.33 | 747.53 ± 316.78 |
| API5 apoptosis inhibitor 5 | 1.24 | 0.0088 | 0.0647 | 187.92 ± 118.48 | 233.04 ± 151.93 |

Pharmacodynamic Effects of Ipilimumab on T Cells

To verify changes in selected molecules from the microarray analysis and further investigate the mechanism of action of ipilimumab, a flow cytometry study was undertaken with the pre-, 3-month and 6-month post-ipilimumab PBMCs from expanded groups of 25 and 37 patients respectively (Table 6b, 6c) overlapping the microarray cohort of 12. In addition to the selected immunological biomarkers, CD4+ and CD8+ T cell effector-memory/naive phenotypes were also measured. Biomarkers with MFI and frequency both significantly changed in absolute value and fold change with p≤0.02 by Wilcoxon and also significant by paired Student T-test.

TABLE 6b

Demographics of patients with 3-month measurements (n = 25)

| Variable | Level | n (%) |
|---|---|---|
| gender | F | 9 (36.0) |
| | M | 16 (64.0) |
| stage | III | 10 (40.0) |
| | IV | 15 (60.0) |
| HLA A2 | A2+ | 18 (72.0) |
| | A2− | 7 (28.0) |
| dosage | 10 mg/kg | 16 (64.0) |
| | 3 mg/kg | 9 (36.0) |
| irAE | N | 15 (60.0) |
| | Y | 10 (40.0) |
| Outcome | NED | 17 (68.0) |
| | Relapse | 8 (32.0) |

TABLE 6c

Demographics of patients with 6-month measurements (n = 37)

| Variable | Level | n (%) |
|---|---|---|
| gender | F | 12 (32.4) |
| | M | 25 (67.6) |
| stage | III | 17 (45.9) |
| | IV | 20 (54.1) |
| HLA A2 | A2+ | 20 (54.1) |
| | A2− | 17 (45.9) |
| dosage | 10 mg/kg | 31 (83.8) |
| | 3 mg/kg | 6 (16.2) |
| irAE | N | 23 (62.2) |
| | Y | 14 (37.8) |
| Outcome | NED | 27 (73.0) |
| | Relapse | 10 (27.0) |

Increased Ki67 Expression in, and ICOS on CD4+ and CD8+ T Cells 3- and 6-Months after Ipilimumab The Ki-67 protein (also known as MKI67) is a cellular marker for proliferation (Scholzen T, et al. *J Cell Physiol.* 182:311-22 (2000)) and cell cycling (Hertoghs K M, et al. *J Clin Invest.* 120:4077-90 (2010)) and is an indicator of the growth fraction of a given cell population. As demonstrated in Table 3a and Table 3b, the MFI and frequency of Ki67 in CD4+ and CD8+ T cells was significantly increased in both 3-month (Table 3a) and 6-month (Table 3b) post-treatment PBMCs with p≤0.0032 for all by Wilcoxon.

TABLE 3a

Statistical analysis of changes in biomarkers at 3 months

| Biomarker | n | Median change* (Q1, Q3) | Wilcoxon p | Median fold change* (Q1, Q3) | Wilcoxon p |
|---|---|---|---|---|---|
| MFI-ICOS-CD4 | 25 | 2.10.00 (71.00, 273.00) | <.0001 | 1.41 (0.60, 2.14) | <.0001 |
| Frequency-ICOS-CD4 | 25 | 13.00 (1.15, 20.69) | <.0001 | 1.35 (0.22, 3.62) | <.0001 |
| MFI-ICOS-CD8 | 25 | 34.90 (4.60, 46.10) | <.0001 | 0.56 (0.09, 1.12) | <.0001 |
| Frequency-ICOS-CD8 | 25 | 4.19 (2.07, 7.75) | <.0001 | 2.90 (1.25, 6.71) | <.0001 |
| MFI-Ki67-CD4 | 24 | 779.50 (178.50, 1657.00) | <.0001 | 0.58 (0.12, 1.43) | <.0001 |
| Frequency-Ki67-CD4 | 24 | 3.62 (0.74, 6.94) | <.0001 | 1.49 (0.18, 2.63) | <.0001 |
| MFI-Ki67-CD8 | 24 | 480.00 (−6.00, −1268.00) | 0.0032 | 0.32 (−0.00, 1.23) | 0.0011 |
| Frequency-Ki67-CD8 | 24 | 1.49 (−0.10, 4.86) | 0.0009 | 0.54 (−0.03, 2.20) | 0.0003 |
| MFI-CCR7-CD8 | 21 | −279.00 (−645.00, 131.00) | 0.0003 | −0.23 (−0.30, 0.12) | 0.0004 |
| Frequency-CCR7-CD8 | 25 | −3.98 (−11.40, 1.30) | 0.0122 | −0.14 (−0.27, 0.04) | 0.018 |

TABLE 3b

Statistical analysis of changes in biomarkers at 6 months

| Biomarker | n | Median change* (Q1, Q3) | Wilcoxon p | Median fold change* (Q1, Q3) | Wilcoxon p |
|---|---|---|---|---|---|
| MFI-ICOS-CD4 | 37 | 111.00 (46.80, 166.00) | <.0001 | 0.84 (0.41, 1.06) | <.0001 |
| Frequency-ICOS-CD4 | 37 | 9.45 (3.13, 14.57) | <.0001 | 1.66 (0.70, 2.42) | <.0001 |
| MFI-ICOS-CD8 | 37 | 29.10 (11.80, 44.50) | <.0001 | 0.47 (0.21, 0.64) | <.0001 |
| Frequency-ICOS-CD8 | 37 | 3.07 (1.62, 5.36) | <.0001 | 1.34 (0.63, 3.30) | <.0001 |
| MFI-Ki67-CD4 | 36 | 535.50 (207.50, 1517.50) | <.0001 | 0.49 (0.24, 1.16) | <.0001 |
| Frequency-Ki67-CD4 | 35 | 2.33 (1.37, 6.97) | <.0001 | 0.87 (0.29, 2.12) | <.0001 |
| MFI-Ki67-CD8 | 36 | 326.00 (85.50, 770.50) | <.0001 | 0.30 (0.10, 0.70) | <.0001 |
| Frequency-Ki67-CD8 | 36 | 1.88 (0.13, 4.91) | 0.0004 | 0.55 (0.04, 1.52) | <.0001 |
| MFI-Gata3-CD4 | 28 | 78.00 (8.00, 189.50) | 0.004 | 0.21 (−0.02, 0.43) | 0.0038 |
| Frequency-Gata3-CD4 | 28 | 3.76 (0.28, 8.04) | 0.0004 | 0.94 (−0.01, 1.62) | <.0001 |
| MFI-Gata3-CD8 | 28 | 76.50 (8.00, 119.50) | 0.0045 | 0.16 (0.03, 0.35) | 0.0032 |
| Frequency-Gata3-CD8 | 28 | 2.07 (0.59, 4.02) | 0.0006 | 0.59 (0.09, 1.23) | <.0001 |
| MFI-CCR7-CD4 | 37 | −290.00 (−587.00, −113.00) | <.0001 | −0.14 (−0.21, −0.07) | <.0001 |
| Frequency-CCR7-CD4 | 37 | −2.90 (−6.80, −0.40) | 0.0017 | −0.03 (−0.09, 0.01) | 0.006 |
| MFI-IL-7R-CD4 | 37 | −23.00 (−45.00, −7.00) | 0.0001 | −0.08 (−0.17, 0.02) | <.0001 |
| Frequency-IL-7R-CD4 | 37 | −1.70 (−3.20, 0.36) | 0.0093 | −0.15 (−0.34, 0.05) | 0.0271 |

Inducible T-cell co-stimulator (ICOS) is a T cell surface molecule structurally related to CD28 and CTLA-4 (Dong C, et al. *Nature*. 409:97-101 (2001)). It is expressed at low levels on resting naïve T cells and is rapidly up-regulated following TCR ligation and CD28 costimulation (McAdam A J, et al. *J Immunol* 165:5035-40 (2000)). After ipilimumab treatment, the MFI and frequency of ICOS was increased significantly on $CD4^+$ and $CD8^+$ T cells, with higher increases on $CD4^+$ than on $CD8^+$ T cells and higher increases at 3-month than at 6-month post treatment (Table 3).

Decreased CCR7 on $CD8^+$ and IL-7R Expression on $CD4^+$ T Cells after Ipilimumab The MFI and frequency of CCR7 expression on $CD8^+$ T cells was decreased at 3- and 6-month post-ipilimumab (Table 3). The MFI of IL-7R on $CD4^+$ T cells was down-regulated at 3-month and 6-month post-ipilimumab treatment, and the frequency of IL-7R on CD4+ T cells was significantly decreased at 6-month post-ipilimumab treatment (Table 3).

Increased GATA3 Expression in $CD4^+$ and $CD8^+$ T Cells

GATA3 is a transcription factor that is a marker for Th2 polarization and is associated with the generation of Th2 cytokines IL-4, IL-5 and IL-10. After treatment with ipilimumab, GATA3 expression as MFI and frequency was increased significantly in $CD4^+$ and $CD8^+$ T cells at 6-month post-ipilimumab treatment (Table 3b).

Surrogate Biomarkers on/in T Cells Associated with Relapse or irAE

In an univariate logistic regression analysis using changes in expression by flow cytometry as a continuous variable one at a time, only absolute decrease in $Ki67^+EOMES^+CD4^+$, in MFI and frequency of $CCR7^+CD8^+$, and increase in MFI of TGFβR3 on $CD8^+$, in MFI and frequency of $EOMES^+CD8^+$ and in $GranzymeB^+EOMES^+CD8^+$ T cells, $Perforin^+ EOMES^+CD8^+$ T cells, and $CTLA-4^+CD4^+$ T cells were associated with a higher likelihood of relapse with p<0.05 (Table 4a). Only absolute decrease of $Ki67^+CD8^+$ T cells, $CD71^+CD8^+$ T cells, $ICOS^+CD8^+$ T cells, and $PD-1^+CD8^+$ T cells were associated with a development of irAE, (Table 4b) with p<0.05.

TABLE 4a

Association of changes in biomarkers at 6 months with outcome

| Variable | Slope | p-value |
| --- | --- | --- |
| Ki67 EOMES CD4 (%) | −3.5232 | 0.0285 |
| MFI CCR7 CD8 | −0.0021 | 0.0158 |
| CCR7 CD8 (%) | −0.0947 | 0.0379 |
| EOMES CD8 (%) | 0.1758 | 0.0072 |
| MFI EOMES CD8 | 0.0025 | 0.0282 |
| MFI TGFbRS CD8 | 0.0049 | 0.0337 |
| EOMES Perforin CD8 (%) | 0.2109 | 0.0278 |
| EOMES Granzyme B CD8 (%) | 0.2126 | 0.0078 |
| CTLA-4 CD4 (%) | 0.4222 | 0.0178 |

TABLE 4b

Association of changes in biomarkers with irAE (Yes vs. No)

| Variable | Slope | p-value |
| --- | --- | --- |
| Ki67 CD8 (%) | −0.3167 | 0.0217 |
| CD71 CD8 | −0.5475 | 0.0484 |
| CD71 CD8 (%) | −0.0075 | 0.0297 |
| ICOS CD8 (%) | −0.0049 | 0.0411 |
| PD-1 CD8 (%) | −0.0293 | 0.0476 |

(%) means percentage of $CD4^+$ or $CD8^+$ T cells (as indicated) that had the indicated markers.
MFI means the mean fluorescence intensity of the indicated marker in the indicated type of T cell ($CD4^+$ or $CD8^{+)}$.

Pre-Treatment Biomarkers on/in T Cells Associated with Outcome and irAE

An analysis dichotomized by the median of baseline biomarkers revealed that low $Ki67^+EOMES^+CD8^+$, high MFI of $CCR7^+CD4^+$ and low $EOMES^+CD8^+$ were significantly associated with relapse (Table 5a) with p values of 0.0008, 0.0190 and 0.0242 respectively. These pre-treatment biomarkers collected from a cohort of 55 patients were also confirmed in a univariable logistic regression analysis. Another analysis of covariate dichotomized by the median value for baseline biomarkers showed that low $Ki67^+EOMES^+CD4^+$ and high MFI of TGFβR3 on $CD8^+$ T cells were associated with occurrence of irAE (Table 5b) with p=0.0046 and p=0.0218 respectively.

TABLE 5a

Association between outcome and dichotomized baseline biomarkers

| Association | Outcome | Covariate Level | n (%) | Odds Ratio (95% CI) | Chi-Square p-value |
| --- | --- | --- | --- | --- | --- |
| Ki67EOMES CD8 Outcome | Relapse | ≤2.11 | 15 (75.0) | 11.25 (2.52, 50.27) | 0.0008 |
| | NED | ≤2.11 | 5 (25.0) | | |
| | Relapse | >2.11 | 4 (21.1) | | |
| | NED | >2.11 | 15 (78.9) | | |
| MFI CCR7 CD4 Outcome | Relapse | ≤2402 | 6 (21.4) | 0.25 (0.08, 0.82) | 0.019 |
| | NED | ≤2402 | 22 (78.6) | | |
| | Relapse | >2402 | 14 (51.9) | | |
| | NED | >2402 | 13 (48.1) | | |
| Frequency EOMES CD8 Outcome | Relapse | ≤55.6 | 14 (51.9) | 3.77 (1.16, 12.27) | 0.0242 |
| | NED | ≤55.6 | 13 (48.1) | | |
| | Relapse | >55.6 | 6 (22.2) | | |
| | NED | >55.6 | 21 (77.8) | | |
| Frequency CD109 CD8 Outcome | Relapse | ≤0.7315 | 5 (19.2) | 0.20 (0.06, 0.71) | 0.0201 |
| | NED | ≤0.7315 | 21 (80.8) | | |
| | Relapse | >0.7315 | 14 (53.8) | | |
| | NED | >0.7315 | 12 (46.2) | | |

TABLE 5b

Association between irAE (Yes/No) and baseline dichotomized biomarkers

| Association | Out-come | Covariate Level | n (%) | Odds Ratio (95% CI) | Chi-Square p-value |
|---|---|---|---|---|---|
| Ki67EOMES CD4 irAE | Y | ≤0.446 | 12 (60.0) | 8.00 (1.74, 36.70) | 0.0046 |
| | N | ≤0.446 | 8 (40.0) | | |
| | Y | >0.446 | 3 (15.8) | | |
| | N | >0.446 | 16 (84.2) | | |
| MFI TGFbR3 CD8 irAE | Y | ≤527 | 8 (28.6) | 0.28 (0.09, 0.85) | 0.0218 |
| | N | ≤527 | 20 (71.4) | | |
| | Y | >527 | 16 (59.3) | | |
| | N | >527 | 11 (40.7) | | |
| Frequency CD71 CD4 irAE | Y | ≤2.79 | 18 (69.2) | 7.50 (2.18, 25.80) | 0.0019 |
| | N | ≤2.79 | 8 (30.8) | | |
| | Y | >2.79 | 6 (23.1) | | |
| | N | >2.79 | 20 (76.9) | | |

Figure 1B:
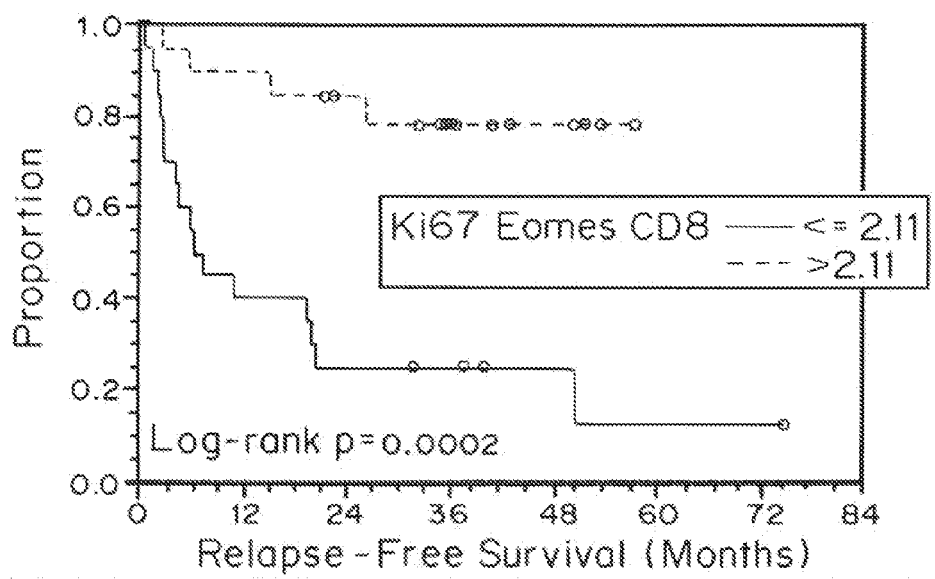
Figure 1C:
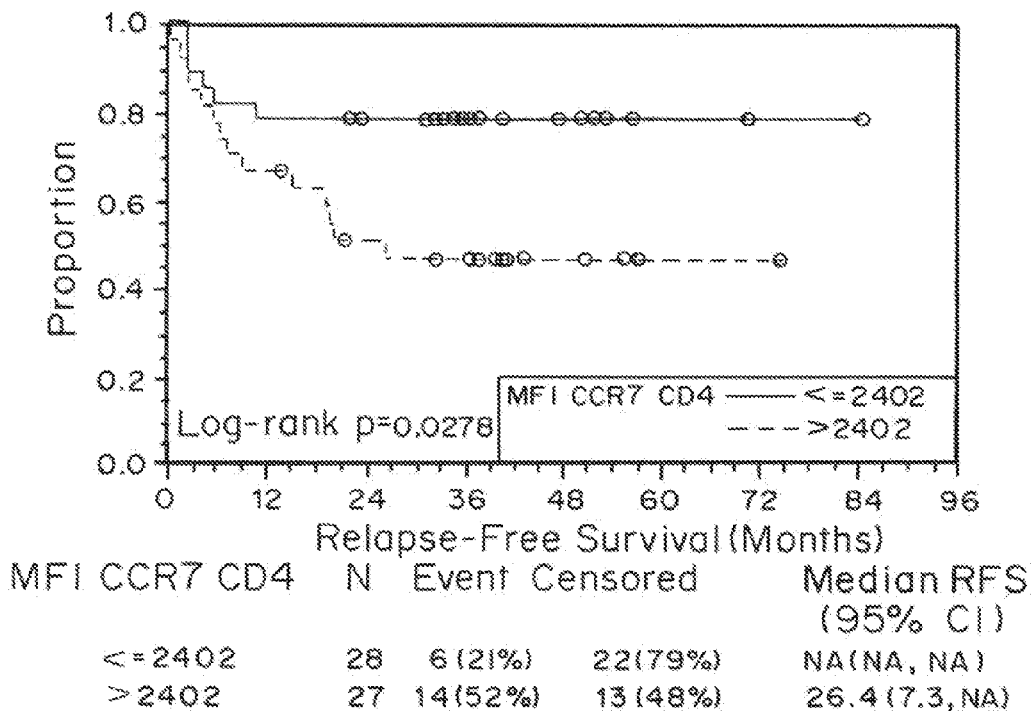

This analysis pointed out the potential importance of EOMES, a transcription factor in the T-box family and involved in the regulation of INF-γ, granzyme B and perforin production by CD8+ T cells (Pearce E L, et al. *Science*. 302:1041-3 (2003)). To better understand the potential role of EOMES+CD8+ T cells in ipilimumab treatment, pre-treatment specimens were stratified by the median frequency of EOMES+ in CD8+ T cells. High baseline frequency of EOMES+ in CD8+ T cells were significantly associated with an improved relapse free survival (RFS) compared with a lower basal level of EOMES+CD8+ T cells (P=0.0183; log-rank test) (FIG. 1A). The patients were stratified by the median frequency of Ki67+EOMES+CD8+. The patients with a higher proportion of Ki67+EOMES+CD8+ T cells had significantly improved RFS compared with those patients with lower frequency of Ki67+EOMES+CD8+ cells (FIG. 1B), p=0.0004 by the long-rank test. Patients were also stratified by the median MFI of CCR7 on CD4+ T cells. The patients with lower MFI of CCR7+ on CD4+ had a significantly better RFS than the higher expressing patients (FIG. 1C), with p value of 0.0278 by the log-rank test.

Figure 2:
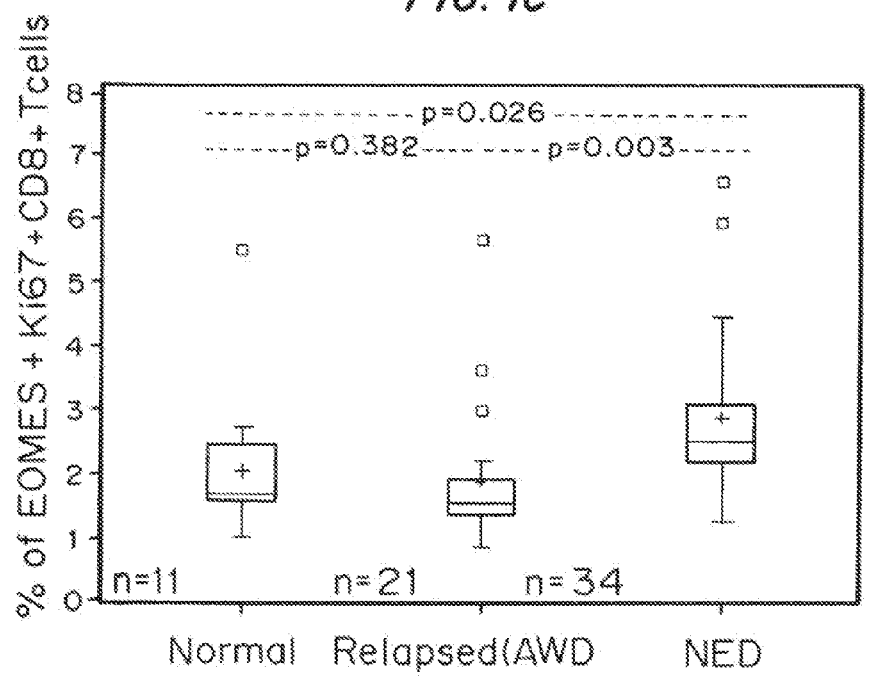
FIG. 2 is a graph of the percent of Ki67$^+$EOMES$^+$/CD8$^+$ cells in CD8$^+$ PBMCs for normal, relapsed, and NED subjects (subjects formerly diagnosed with cancer but now showing no evidence of disease). p-values in the graph are from Wilcoxon rank-sum test. Overall p-value=0.038 for comparing the three groups from Kruskal-Wallis test.
Figure 3:
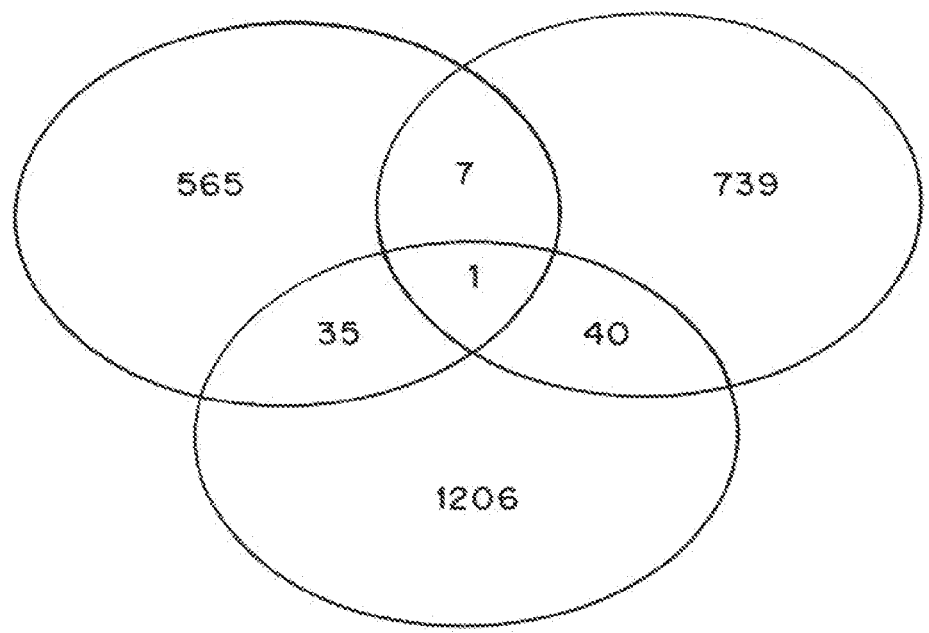
FIG. 3 is a Venn diagram of gene profiling impacted differentially by PD-1 blockade according to dose.

Some of the significant biomarkers were tested on the 11 available normal phereses. Results for the most significant biomarker (EOMES+Ki67+CD8+) on the 11 normals and the melanoma patients (relapse and NED) in this trial is shown in FIG. 2. The median of EOMES+Ki67+CD8+ T cells for the 11 normal was 1.57, very similar to the median for the relapse group patients which was 1.50. For the NED group, the median of EOMES+Ki67+CD8+ T cells was 2.49 significantly higher than median of relapsed patients (p=0.03, student T test).

Biomarker levels associated with cancer prognosis and CTLA-4 blockade treatment are shown in Table 7. The range in the last column is the range of values for that biomarker seen in the group of patients.

TABLE 7

Biomarker Levels Associated with Cancer Prognosis and CTLA-4 Blockade Treatment

| Biomarkers | Association | Unit | Cut off Value | Range for total patients |
|---|---|---|---|---|
| Ki67+EOMES+CD8+ | outcome-NED | % | >2.11 | 5.77 |
| EOMES+CD8+ | outcome-NED | % | >55.6 | 67.8 |
| MFI-CCR7-CD4+ | outcome-NED | MFI | ≤2402 | 3080 |
| Ki67+EOMES+CD4+ | irAE-No | % | >0.446 | 1.96 |
| MFI-TGFbR3-CD8+ | irAE-No | MFI | ≤527 | 1711 |

* %: Percentage
* MFI: Mean Fluorescence Intensity

Example 2: Gene Profiling of Melanoma Patients CD8+ T Cells Associated with PD-1 Blockade Treatment and Clinical Outcome PD-1 blocking antibody (BMS-936558) therapy has shown antitumor activity and clinical benefit in melanoma patients. The precise molecular basis and mechanisms of PD-1 blockade in vivo have not been documented and there are few biomarker associated with clinical benefit. The purpose of this study is to understand the mechanisms and investigate potential baseline and surrogate biomarkers associated with clinical benefit of PD-1 blockade in stage IV unresectable melanoma patients' T cells in vivo.

Materials and Methods

Microarray analysis was performed on flow sorted CD8+ T cells from PBMCs collected pre- and 12 week-post PD-1 blockade treatment at 1, 3 and 10 mg/kg. The pre-treatment sample was collected within 1 week before anti PD-1 treatment. The post-treatment sample was collected 12 weeks after the initial treatment with 6 injections of anti PD-1 antibody. Stage IIIC and stage IV melanoma patients received intravenous infusion of anti PD-1 (BMS-936558) in dose-escalating ten-patient cohorts at 1, 3, 10 mg/kg.

Results

To address the molecular mechanisms of PD-1 blockade on human CD8+ T cells, the molecular signature of PD-1 blockade treatment was characterized at 1, 3, 10 mg/kg by comparing the gene-expression profiles of CD8+ T cells from pre and post treatment T cells.

Gene signatures associated with clinical benefit were assessed by comparing 11 clinical responders to 11 non-responders at baseline, post-treatment at 12 weeks and assessed changes of post vs. pre samples.

Figure 4:
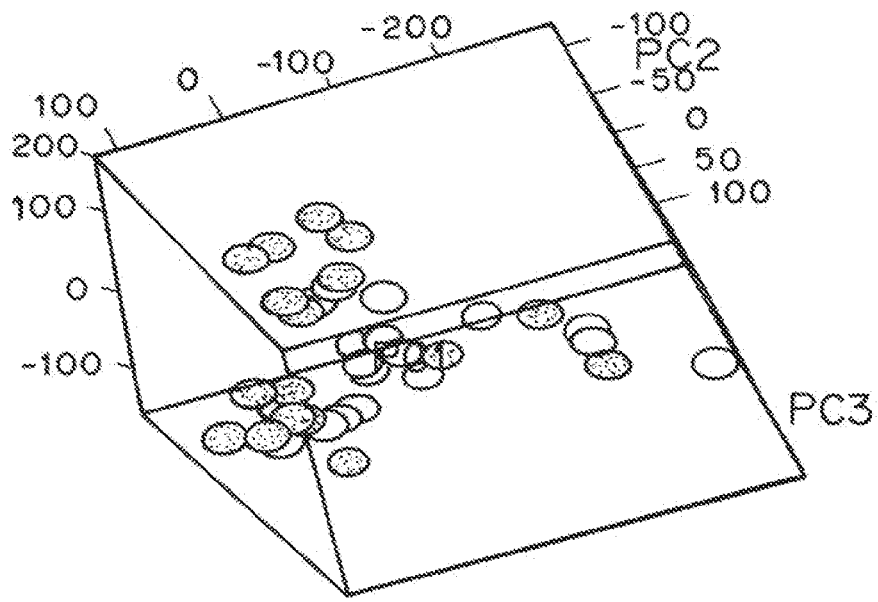
FIG. 4 is a principle component analysis (PCA) of pre and post treatment gene expression of CD8$^+$ T cells for separate clinical responders and non responders to PD-1 blockade treatment.
Figure 5:
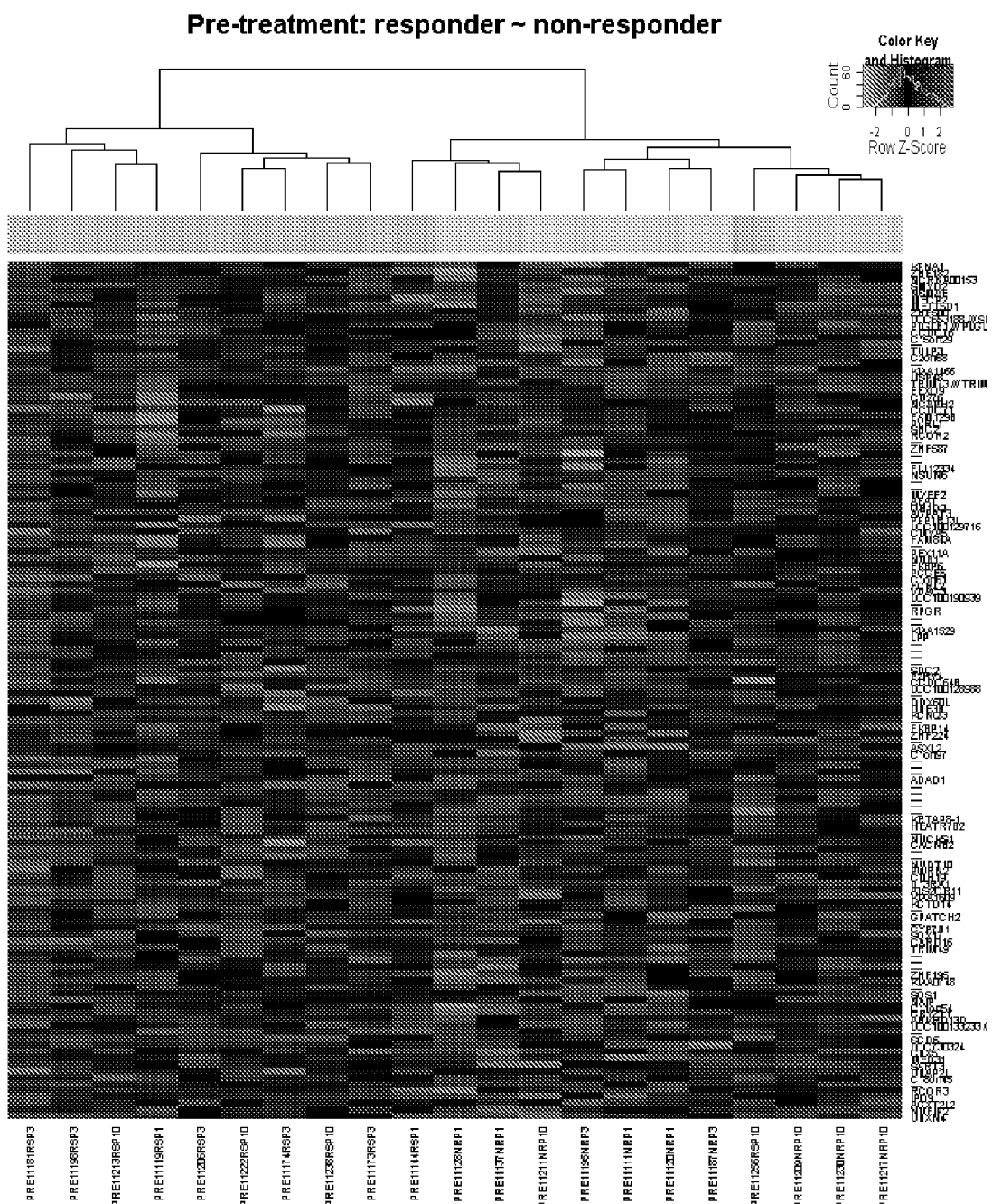
FIG. 5 is a heat map of baseline gene expression associated with clinical response by PD-1 blockade.
Figure 6:
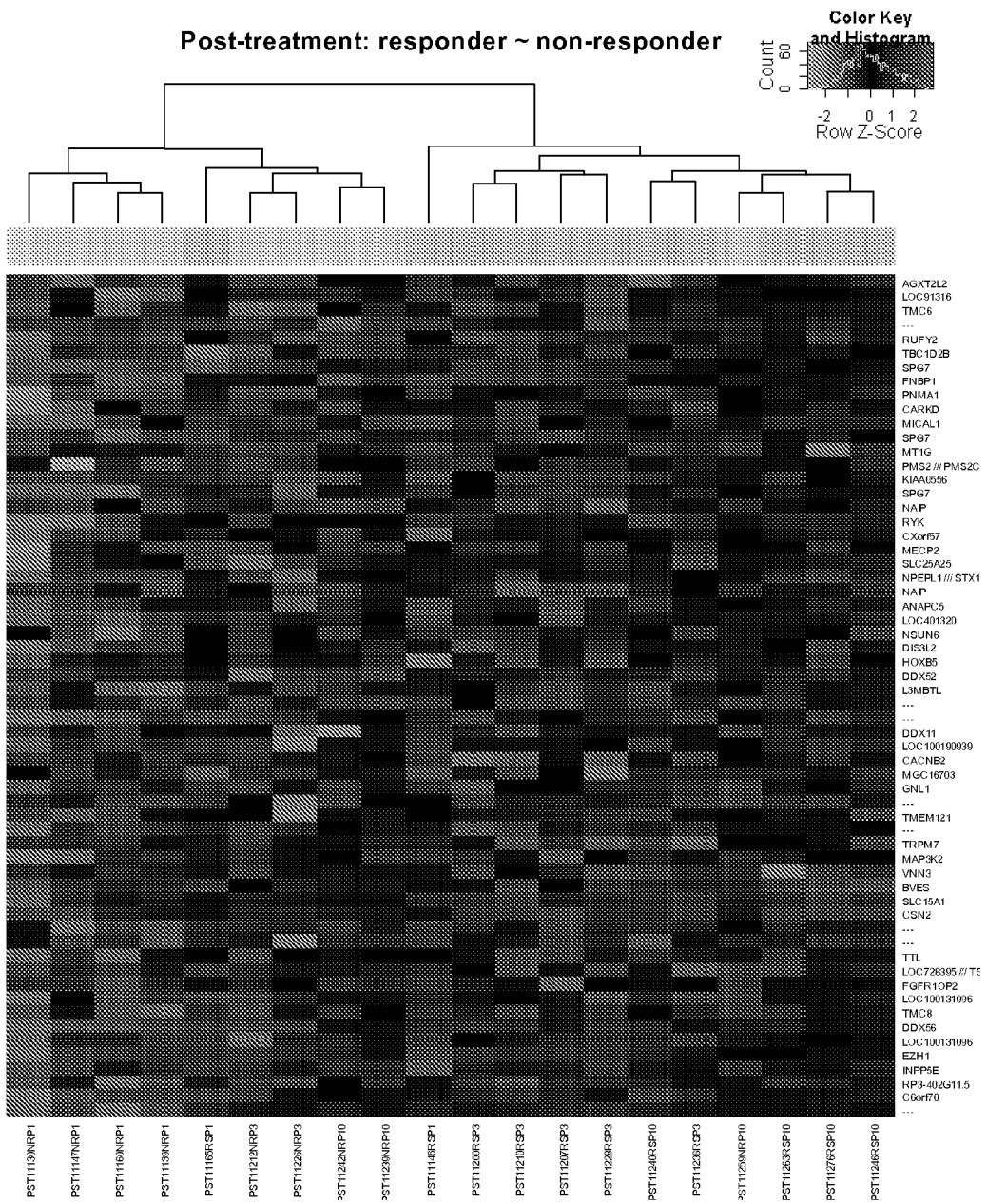
FIG. 6 is a heat map of post-treatment gene expression associated with clinical response by PD-1 blockade.
Figure 7A:
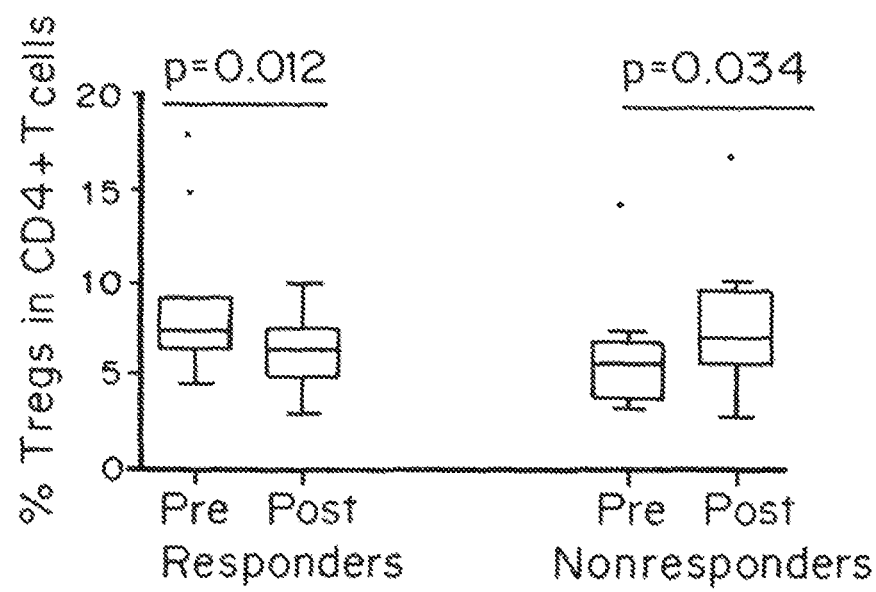
FIGS. 7A, 7B, 7C, and 7D are graphs of marker differences in responders and nonresponders to treatment with BMS-936558. There were a total 25 patients with 12 weeks measurement after BMS-936558 treatment; 13 responders and 12 non-responders.
Figure 7B:
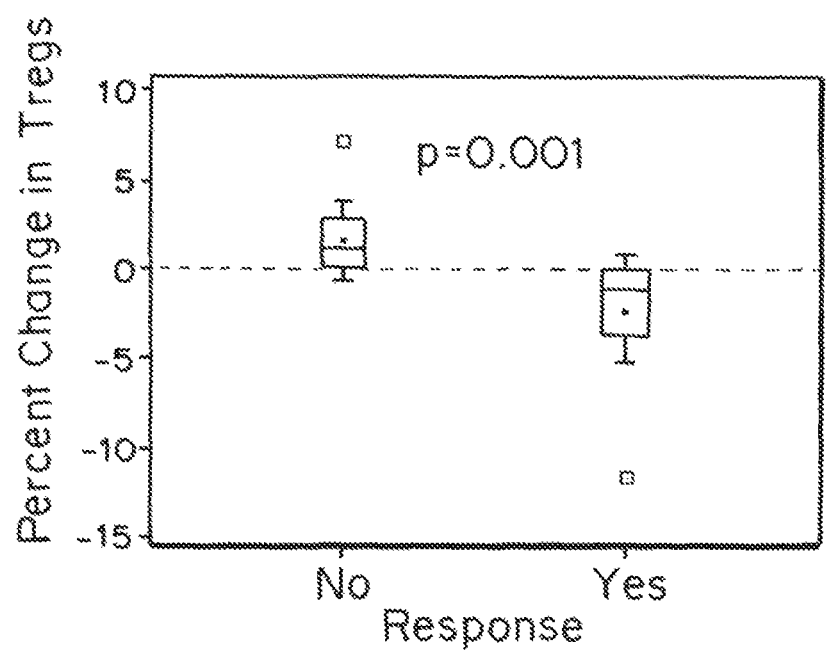
Figure 7C:
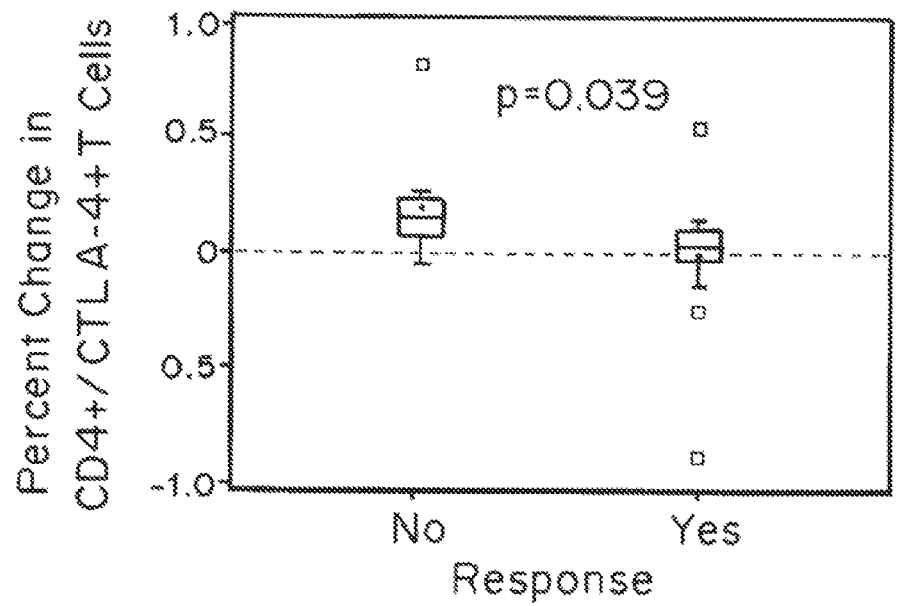
Figure 7D:
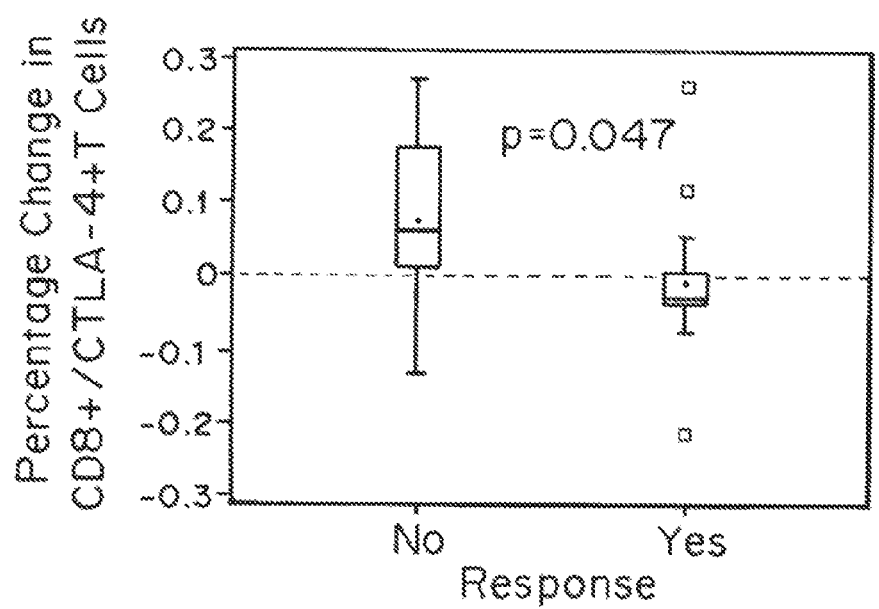

Results: PD-1 blockade differentially impacts gene expression of CD8+ T cells at 1, 3 and 10 mg/kg. Baseline and post treatment gene profiles of CD8+ T cells are significantly associated with clinical benefit (FIG. 4 (PCA), FIGS. 5 and 6 (Heat Map)). At base line: low CD276 (B7-H3), high NKTR, PTEN and GATAD1 in CD8+ T cells are associated with clinical response (Table 9). Increased LAG1, decreased GADD45B, EGR1 and EGR2 are associated with clinical benefit at week 12 post-treatment (Table 8).

Baseline, post-treatment, and changes in gene expression profiling of CD8+ T cells are significantly associated with clinical response after PD-1 blockade. This approach revealed key insights into the biology of PD-1 blockade. Breaking CD8+ T cell anergy is thus associated with clinical benefit.

TABLE 8

Post-treatment Changes in Gene Profile Associated with Response

| Symbol | Gene Title | Fold | pValue | Mean Post/ Mean Pre |
|---|---|---|---|---|
| LASS6 | LAG1 homolog, ceramide synthase 6 | 1.30 | 0.0211 | 263.9/202.6 |
| GADD45G | growth arrest, DNA-damage-inducible, g | 0.79 | 0.0414 | 90.1/114.0 |
| ING1 | inhibitor of growth family, member 1 | 0.78 | 0.016 | 100.4/128.0 |
| CKS2 | CDC28 protein kinase regulatory subunit 2 | 0.78 | 0.0101 | 345.3/445.0 |
| CDKN1C | Cyclin-dependent kinase inhibitor 1C | 0.78 | 0.0010 | 65.8/84.5 |

TABLE 8-continued

Post-treatment Changes in Gene Profile Associated with Response

| Symbol | Gene Title | Fold | pValue | Mean Post/ Mean Pre |
|---|---|---|---|---|
| IFIH1 | interferon induced with helicase C domain 1 | 0.78 | 0.0305 | 38.3/48.9 |
| GADD45B | Growth arrest DNA-damage-inducible, beta | 0.67 | 0.0003 | 1851.1/2647.7 |
| IER5 | immediate early response 5 | 0.76 | 0.0045 | 3906.4/5155.9 |
| IFNG | interferon, gamma | 0.73 | 0.0232 | 1062.9/1446.8 |
| IER5L | immediate early response 5-like | 0.67 | 0.0207 | 180.9/271.3 |
| EGR2 | early growth response 2 | 0.67 | 0.046 | 81.9/121.9 |
| EGR1 | Early growth response 1 | 0.35 | 0.0156 | 1119.0/3218.2 |

TABLE 9

Baseline Gene Expression Associated with Response

| Symbol | Gene Title | Fold | pValue | Mean Responders/ Non Responders |
|---|---|---|---|---|
| USP9Y | ubiquitin specific peptidase 9, Y-linked | 2.23 | 0.0441 | 255.2/114.3 |
| HSPD1 | heat shock 60 kDa protein 1 (chaperonin) | 1.92 | 0.0415 | 50.8/26.4 |
| NSUN6 | NOL1/NOP2/Sun domain family, member 6 | 1.72 | 3.04E−05 | 150.5/87.3 |
| CISH | cytokine inducible SH2-containing protein | 1.7 | 0.0288 | 248.1/145.5 |
| KLF12 | Kruppel-like factor 12 | 1.59 | 0.0142 | 192.5/121.3 |
| NCF4 | neutrophil cytosolic factor 4, 40 kDa | 1.51 | 0.049 | 59.8/39.5 |
| SFRS7 | splicing factor, arginine/serine-rich 7, 35 kDa | 1.49 | 0.0113 | 1000.1/670.6 |
| CDC14A | CDC14 cell division cycle 14 homolog A (S. cerevisiae) | 1.49 | 0.0412 | 144.3/97 |
| MAP2K5 | Mitogen-activated protein kinase kinase 5 | 1.48 | 0.017 | 77.4/52.4 |
| CCAR1 | Cell division cycle and apoptosis regulator 1 | 1.46 | 0.0095 | 241.3/165.2 |
| IL11RA | interleukin 11 receptor, alpha | 1.46 | 0.0232 | 604.3/414.7 |
| MLL | myeloid/lymphoid or mixed-lineage leukemia | 1.43 | 0.0391 | 36.2/25.3 |
| HSPBAP1 | HSPB (heat shock 27 kDa) associated protein 1 | 1.42 | 0.0113 | 319.2/225.2 |
| MAP4K4 | mitogen-activated protein kinase kinase kinase kinase 4 | 1.41 | 0.0242 | 223.2/158.7 |
| HELLS | helicase, lymphoid-specific | 1.41 | 0.0351 | 107.4/76.0 |
| SMYD2 | SET and MYND domain containing 2 | 1.37 | 0.0009 | 168.2/122.6 |
| C1QTNF3 | C1q and tumor necrosis factor related protein 3 | 1.36 | 0.0242 | 65.6/48.1 |
| PTEN | phosphatase and tensin homolog | 1.34 | 0.0232 | 49.9/37.3 |
| UBE2D1 | ubiquitin-conjugating enzyme E2D 1 | 1.34 | 0.0418 | 77.8/57.8 |
| FBXO9 | F-box protein 9 | 1.33 | 0.006 | 208.1/156.7 |
| FAIM3 | Fas apoptotic inhibitory molecule 3 | 1.33 | 0.0164 | 885.2/665.9 |
| IFI44 | Interferon-induced protein 44 | 1.33 | 0.043 | 91.8/68.9 |
| NCRNA00153 | Non-protein coding RNA 153 | 1.31 | 0.0031 | 146.3/111.8 |
| NSMAF | Neutral sphingomyelinase activation associated factor | 1.3 | 0.0014 | 149.4/114.8 |
| H2BFM | H2B histone family, member M | 1.3 | 0.0412 | 100.5/77.5 |
| GATAD1 | GATA zinc finger domain containing 1 | 1.29 | 0.0412 | 214.7/166.5 |
| GATAD1 | GATA zinc finger domain containing 1 | 1.27 | 0.0258 | 385.9/302.9 |
| NKTR | natural killer-tumor recognition sequence | 1.27 | 0.0263 | 2486.9/1951.9 |
| CASP8 | caspase 8, apoptosis-related cysteine peptidase | 1.27 | 0.035 | 2326.9/1839.1 |

TABLE 9-continued

Baseline Gene Expression Associated with Response

| Symbol | Gene Title | Fold | pValue | Mean Responders/ Non Responders |
|---|---|---|---|---|
| SOCS1 | suppressor of cytokine signaling 1 | 0.8 | 0.0182 | 95.7/119.9 |
| P2RY4 | pyrimidinergic receptor P2Y, G-protein coupled, 4 | 0.8 | 0.0005 | 39.4/49.1 |
| CD276 | CD276 molecule (B7-H3) | 0.79 | 0.0003 | 108.1/136.9 |
| RCOR2 | REST corepressor 2 | 0.78 | 0.0011 | 156.9/201.4 |
| PDCD6 | Programmed cell death 6 | 0.77 | 0.0151 | 921.4/1198.5 |
| NUB1 | negative regulator of ubiquitin-like proteins 1 | 0.75 | 0.0054 | 84.1/111.4 |
| FCRL2 | Fc receptor-like 2 | 0.71 | 0.0045 | 62.1/87.8 |
| NUCKS1 | Nuclear casein kinase, cyclin-dependent kinase substrate 1 | 0.69 | 0.0055 | 24.5/35.4 |
| SHC2 | SHC transforming protein 2 | 0.66 | 0.0036 | 98.1/149.1 |
| SCD5 | stearoyl-CoA desaturase 5 | 0.64 | 0.0037 | 211.6/328.3 |

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a PD-1 blockade therapy is disclosed and discussed and a number of modifications that can be made to a number of molecules including the active molecule are discussed, each and every combination and permutation of the therapy and molecule and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the subgroup of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Those skilled in the art will recognize, or be able to ascertain using no more than routine experimentation, many equivalents to the specific embodiments of the invention described herein. Such equivalents are intended to be encompassed by the following claims.

We claim:

1. A method comprising
(1) assaying peripheral blood mononuclear cells (PB-MCs) from a subject diagnosed with melanoma for expression of (a) CD8, Ki67, and eomesodermin (EOMES); (b) CD8 and EOMES; or (c) CD4, Ki67, and EOMES, wherein the frequency of Ki67+EOMES+CD8+ T cells in the PBMCs is inversely proportional with the risk of relapse after CTLA-4 blockade treatment, wherein the frequency of EOMES+CD8+ T cells in CD8+ T cells in the PBMCs is inversely proportional with the risk of relapse after CTLA-4 blockade treatment, wherein the frequency of Ki67+EOMES+CD4+ T cells in CD4+ T cells in the PBMCs is inversely proportional with the risk of an immune related adverse event (irAE) after CTLA-4 blockade treatment, (2) treating the subject with a CTLA-4 blockade treatment if (a) the frequency of Ki67+EOMES+CD8+ T cells in PBMCs of the subject is at least 2.2%, (b) the frequency of EOMES+CD8+ T cells in PBMCs of the subject is at least 56%, or (c) the frequency of Ki67+EOMES+CD4+ T cells in PBMCs of the subject is at least 0.45%.

2. A method comprising
assaying peripheral blood mononuclear cells (PBMCs) from a subject diagnosed with melanoma for expression of (a) CD8, Ki67, and eomesodermin (EOMES); (b) CD8 and EOMES; or (c) CD4, Ki67, and EOMES; and
treating the subject with a treatment other than a CTLA-4 blockade treatment if (a) the frequency of Ki67+EOMES+CD8+ T cells in PBMCs of the subject is less than 2.11%, (b) the frequency of EOMES+CD8+ T cells in PBMCs of the subject is less than 55.6%, or (c) the frequency of Ki67+EOMES+CD4+ T cells in PBMCs of the subject is less than 0.446%.

3. A method comprising
assaying peripheral blood mononuclear cells (PBMCs) from a subject diagnosed with melanoma for expression of (a) CD8, Ki67, and eomesodermin (EOMES); (b) CD8 and EOMES; or (c) CD4, Ki67, and EOMES; and
treating the subject with both a CTLA-4 blockade treatment and a different treatment if (a) the frequency of Ki67+EOMES+CD8+ T cells in PBMCs of the subject is less than 2.11%, (b) the frequency of EOMES+CD8+ T cells in PBMCs of the subject is less than 55.6%, or (c) the frequency of Ki67+EOMES+CD4+ T cells in PBMCs of the subject is less than 0.446%.

4. The method of claim 1 further comprising selecting a subject for CTLA-4 blockade treatment, after the step of assaying and prior to the step of treating, if (a) the frequency of Ki67+EOMES+CD8+ T cells in PBMCs of the subject is at least 2.2%, (b) the frequency of EOMES+CD8+ T cells in PBMCs of the subject is at least 56%, or (c) the frequency of Ki67+EOMES+CD4+ T cells in PBMCs of the subject is at least 0.45%.

5. The method of claim 2 further comprising selecting a subject for a treatment, after the step of assaying and prior to the step of treating, other than a CTLA-4 blockade treatment if (a) the frequency of Ki67+EOMES+CD8+ T cells in PBMCs of the subject is less than 2.11%, (b) the frequency of EOMES+CD8+ T cells in PBMCs of the subject is less than 55.6%, or (c) the frequency of Ki67+EOMES+CD4+ T cells in PBMCs of the subject is less than 0.446%.

6. The method of claim 3 further comprising selecting a subject for treatment, after the step of assaying and prior to the step of treating, with both a CTLA-4 blockade treatment and a different treatment if (a) the frequency of Ki67+EOMES+CD8+ T cells in PBMCs of the subject is less than 2.11%, (b) the frequency of EOMES+CD8+ T cells in PBMCs of the subject is less than 55.6%, or (c) the frequency of Ki67+EOMES+CD4+ T cells in PBMCs of the subject is less than 0.446%.

7. A method comprising
assaying peripheral blood mononuclear cells (PBMCs) from a subject diagnosed with melanoma for expression of (a) CD8, Ki67, and eomesodermin (EOMES); (b) CD8 and EOMES; or (c) CD4, Ki67, and EOMES,
wherein the subject is treated with a CTLA-4 blockade treatment if (a) the frequency of Ki67+EOMES+CD8+ T cells in PBMCs of the subject is at least 2.2%, (b) the frequency of EOMES+CD8+ T cells in PBMCs of the subject is at least 56%, or (c) the frequency of Ki67+EOMES+CD4+ T cells in PBMCs of the subject is at least 0.45%, and
wherein the subject is not treated with a CTLA-4 blockade treatment if (a) the frequency of Ki67+EOMES+CD8+ T cells in PBMCs of the subject is less than 2.11%, (b) the frequency of EOMES+CD8+ T cells in PBMCs of the subject is less than 55.6%, or (c) the frequency of Ki67+EOMES+CD4+ T cells in PBMCs of the subject is less than 0.446%.

8. A method of treating a subject diagnosed with melanoma comprising treating the subject with a CTLA-4 blockade treatment when (a) the measured frequency of Ki67+EOMES+CD8+ T cells in peripheral blood mononuclear cells (PBMCs) of the subject is at least 2.2%, (b) the measured frequency of EOMES+CD8+ T cells in PBMCs of the subject is at least 56%, or (c) the measured frequency of Ki67+EOMES+CD4+ T cells in PBMCs of the subject is at least 0.45%.

9. The method of claim 1, wherein the CTLA-4 blockade treatment is treatment with ipilimumab or tremelimumab.

10. The method of claim 1, wherein the CTLA-4 blockade treatment is treatment with ipilimumab.

11. The method of claim 1, wherein the subject is treated with a CTLA-4 blockade treatment if the measured frequency of Ki67+EOMES+CD8+ T cells in peripheral blood mononuclear cells (PBMCs) of the subject is at least 2.2%.

12. The method of claim 8, wherein the CTLA-4 blockade treatment is treatment with ipilimumab or tremelimumab.

13. The method of claim 8, wherein the subject is treated with a CTLA-4 blockade treatment if the measured frequency of Ki67+EOMES+CD8+ T cells in peripheral blood mononuclear cells (PBMCs) of the subject is at least 2.2%.

14. The method of claim 7, wherein the CTLA-4 blockade treatment is treatment with ipilimumab or tremelimumab.

* * * * *